US008962341B2

(12) United States Patent
Zacharias et al.

(10) Patent No.: US 8,962,341 B2
(45) Date of Patent: Feb. 24, 2015

(54) CELL-BASED DETECTION OF APF THROUGH ITS INTERACTION WITH CKAP4 FOR DIAGNOSIS OF INTERSTITIAL CYSTITIS

(75) Inventors: David Alan Zacharias, St. Augustine, FL (US); Sonia Lobo Planey, Scranton, PA (US)

(73) Assignees: The Commonwealth Medical College, Scranton, PA (US); University of Florida Research Foundation, Inc., Gainesville, FL (US)

( * ) Notice: Subject to any disclaimer, the term of this patent is extended or adjusted under 35 U.S.C. 154(b) by 228 days.

(21) Appl. No.: 13/133,244

(22) PCT Filed: Dec. 10, 2009

(86) PCT No.: PCT/US2009/067487
§ 371 (c)(1),
(2), (4) Date: Jun. 9, 2011

(87) PCT Pub. No.: WO2010/068747
PCT Pub. Date: Jun. 17, 2010

(65) Prior Publication Data
US 2011/0244493 A1 Oct. 6, 2011

Related U.S. Application Data

(60) Provisional application No. 61/122,157, filed on Dec. 12, 2008.

(51) Int. Cl.
| G01N 21/77 | (2006.01) |
| C12M 3/00 | (2006.01) |
| G01N 21/75 | (2006.01) |
| G01N 33/50 | (2006.01) |
| C07K 9/00 | (2006.01) |
| C07K 14/705 | (2006.01) |
| C12Q 1/68 | (2006.01) |
| G01N 33/68 | (2006.01) |

(52) U.S. Cl.
CPC ............ *G01N 33/5091* (2013.01); *C07K 9/005* (2013.01); *C07K 14/705* (2013.01); *C12Q 1/6897* (2013.01); *G01N 33/6893* (2013.01); *G01N 2333/4728* (2013.01); *G01N 2800/34* (2013.01)
USPC ............ 436/169; 435/7.1; 435/334; 435/371; 435/287.2; 435/287.7; 435/287.9; 435/288.3; 435/288.7; 436/518; 436/524; 436/528; 436/44; 436/46; 436/161; 422/402; 422/409

(58) Field of Classification Search
USPC .............. 435/7.21, 7.5, 326, 334, 371, 287.2, 435/287.9, 288.3, 7.1, 287.7, 288.7; 436/513, 514, 518, 524, 528, 548, 44, 436/46, 811, 161, 169; 422/402, 409
See application file for complete search history.

(56) References Cited

U.S. PATENT DOCUMENTS

| 4,366,241 | A | | 12/1982 | Tom et al. |
| 4,632,901 | A | | 12/1986 | Valkirs et al. |
| 4,683,195 | A | | 7/1987 | Mullis et al. |
| 4,770,853 | A | | 9/1988 | Bernstein |
| 4,786,589 | A | | 11/1988 | Rounds |
| 4,879,236 | A | | 11/1989 | Smith |
| 5,011,912 | A | | 4/1991 | Hopp et al. |
| 5,530,101 | A | | 6/1996 | Queen et al. |
| 5,625,048 | A | | 4/1997 | Tsien et al. |
| 5,656,448 | A | * | 8/1997 | Kang et al. .................. 435/7.94 |
| 5,661,035 | A | | 8/1997 | Tsien et al. |
| 5,741,657 | A | | 4/1998 | Tsien et al. |
| 5,871,986 | A | | 2/1999 | Boyce |
| 5,981,200 | A | | 11/1999 | Tsien et al. |
| 6,143,502 | A | | 11/2000 | Grentzmann et al. |
| 7,005,511 | B2 | | 2/2006 | Tsien et al. |
| 7,090,803 | B1 | | 8/2006 | Gould et al. |
| 7,157,566 | B2 | | 1/2007 | Tsien et al. |
| 7,250,298 | B2 | | 7/2007 | Glick et al. |
| 7,297,529 | B2 | | 11/2007 | Polito et al. |
| 7,329,735 | B2 | | 2/2008 | Tsien et al. |
| 7,344,893 | B2 | | 3/2008 | Kirkegaard et al. |

(Continued)

FOREIGN PATENT DOCUMENTS

| WO | 2008014484 A1 | 1/2008 |
| WO | 2008144485 A2 | 11/2008 |

OTHER PUBLICATIONS

Conrads et al. CKAP4/p63 Is a Receptor for the Frizzled-8 Protein-related Antiproliferative Factor from Interstitial Cystitis Patients, The Journal of Biological Chemistry 281 (49): 37836-37843 (Dec. 8, 2006).*
International Search Report for PCT/US2009/067487, Apr. 12, 2010.
Genbank Accession No. NM 006825, Aug. 25, 1999.
Genbank Accession No. BC082972, Sep. 28, 2004.
Genbank Accession No. BC094824, May 9, 2005.
Conrads, T.P., et al., CKAP4 . . . , Journal of Biological Chemistry, 2006, vol. 281, No. 49, pp. 37836-37843.
Gupta, N., et al, "Identification and characterization . . . " American Journal of Physiology, Lung Cellular and Molecular Physiology, 2006, vol. 291, pp. L436-L446.

(Continued)

*Primary Examiner* — Gail R Gabel
(74) *Attorney, Agent, or Firm* — Caesar, Rivise, Bernstein, Cohen & Pokotilow, Ltd.

(57) ABSTRACT

An assay system designed to detect a protein biomarker in urine that is diagnostic for interstitial cystitis (IC). The presence of a 9 amino acid glycopeptide, antiproliferative factor (APF), in urine is unique to patients with IC. Urine samples from patients who exhibit symptoms consistent with IC are added to the assay system. Binding of APF to the cytoskeletal associated protein 4 (CKAP4) is positive for the presence of APF in urine and diagnostic for IC. The diagnostic system is a significant and surprising advance in diagnosis of IC and has commercial applications relevant to women and men who suffer from symptoms consistent with IC.

4 Claims, 28 Drawing Sheets

(56) References Cited

U.S. PATENT DOCUMENTS

| | | |
|---|---|---|
| 7,393,923 B2 | 7/2008 | Tsien et al. |
| 2010/0055113 A1* | 3/2010 | Keay et al. ............... 424/172.1 |
| 2011/0244493 A1 | 10/2011 | Zacharias et al. |

OTHER PUBLICATIONS

Schweizer, A., et al., "A reversibly palmitoylated . . . ", Journal of Cell Science, 1993, vol. 104, pp. 685-694.

Planey, S.L, et al., "Palmitoylation off Cytoskeleton . . . ", Molecular Biology of the Cell, Mar. 1, 2009, vol. 20, pp. 1454-1463.

Zhang, et al. (2008) Identification of CKAP4/p63 as a Major Substrate of the Palmitoyl Acyltransferase DHHC2, a Putative tumor Suppressor, Using a Novel proteomics Method. Moll Cell Proteomics 7, 1378-1388.

Yanai, et al, (2006) Palmitoylation of huntingtin by HIP 14 is essential for its trafficking and function. Nat Neurosci 9, 824-831.

Zacharias, et al. (2012) Antiproliferative Factor-Induced Changes in Phosphorylation and Palmitoylation of cytoskeleton-Associated protein-4 Regulate Its Nuclear Translocation and DNA Binding, International Journal of Cell Biology, vol. 2012, Article id 150918, 13 pages.

Chen-Ou-Zhang, et al. APF, HB-EGF, and EGF biomarkers in patients with ulcerative vs. non-ulcerative interstitial cystitis, BMC Urology 2005.

Matika, et al, Antiproliferative factor regulates connective tissue growth factor (CTGF/CCN2) expression in T24 bladder carcinoma cells, Molecular Biology of the Cell, vol. 23, May 15, 2012.

Zacharias, et al. Partitioning of Lipid-Modified Monomeric GFPs into Membrane Microdomains of Live Cells, Science, vol. 296, May 3, 2002, pp. 913-916.

Bano, et al. (1998) Pseudo-enzymatic S-acylation of a myristoylated yes protein tyrosine kinase peptide in vitro may reflect non-enzymatic S-acylation in vivo. Biochem J 330 (Pt2), 723-731.

Bizzozero, et al. (1987) Autoacylation of myelin proteolipid protein withacyl coenzyme, A.J. Biol Chem 262, 13550-13557.

Bova, et al. (1993) Homozygous deletion and frequentallelic loss of chromosome 8p22 loci in human prostate cancer, Cancer Res 53, 3869-3873.

Conrads, et al (2006) CKAP4/p63 is a receptor for the frizzled-8 protein-related antiproliferative factor from interstitial cystitis patients, J Biol Chem 281, 37836-37843.

Emi, et al. (1993) Allelic loss at chromosome band 8p21.3-p22 is associated with progression of hepatocellular carcinoma. Genes Chromosome Cancer 7, 152-157.

Fujiwara, et al. (1993) Evidence or the presence of two tumor suppressor genes on chromosome 8p for colorectal carcinoma. Cancer Res53, 1172-1174.

Gupta, al. et al (2006) Identification and characterization of p63 (CKAP4/ERGIC-63/CLIMP-63), a surfactant protein A binding protein, on type II pneumocytes. Am J Physiol Lung Cell Mol Physiol 291, L436-446.

Ichii, et al (1993) Detailed analysis of genetic alterations in colorectal tumors from patients with and without familial adenomatous polyposis (FAP), Oncogene 8, 2399-2405.

Jones, et al (1997), Ligand-gated ion channel subunit partnerships: GABAA receptor alpha6 subunit gene inactivation inhibits delta subunit expression. J. Neurosci 17, 1350-1362.

Keay, et al. Bladder epithelial cells from patients with interstitial cystitis produce an inhibitor of heparin-binding epidermal growth factor-like growth factor production, J. Urol 164, 2112-2118, Dec. 2000.

Keay, et al, (2003) Changes in human bladder epithelial cell gene expression associated with interstitial cystitis or antiproliferative factor treatment. Physiol Genomics 14, 107-115.

Keay, et al, (2006) The frizzled 8-related antiproliferative factor from IC patients inhibits bladder and kidney carcinoma cell proliferation in vitro. European Journal of Cancer Supplements 4, 87-88.

Keay, et al, (2003) Antiproliferative factor, heparin-binding epidermal growth factor-like growth factor, and epidermal growth factor in men with interstitial cystitis versus chronic pelvic pain syndrome, Urology 63, 22-26.

Keay, et al, (1996) Decreased 3H-thymidine incorporation by human bladder epithelial cells following exposure to urine from interstitial cystitis patients. J Urol 156, 2073-2078.

Keay, et al An antiproliferative factor from interstitial cystitis patients is a frizzled 8 protein related sialoglycopeptide. proc Natl Acad Sci USA 101, 11803-11808, Aug. 10, 2004.

Kim et al, p53 mediates interstitial cystitis antiproliferative factor (APF)-induced growth inhibition of human urothelial cells, FEBS Lett 581, 3795-3799, Aug. 7, 2007.

Klopfenstein, (1998) A novel direct interaction of endoplasmic reticulum with microtubules. Embo J 17, 6168-6177.

Klopfenstein, Subdomain-specific localization of CLIMP-63 (p-63) in the endoplasmic reticulum is mediated by its luminal alpha-helical segment J Cell Biol 153, 1287-1300, Jun. 11, 2001.

Sharma, et al, (2008) Affects Palmitoylation, Stability, and Functions of Tetraspanins CD9 and CD151. ol Biol Cell.

Lobo, et al, Identification of a Ras palmitoyltransferase in Saccharomyces cerevisiae. J Biol Chem 277, 41268-41273, Oct. 25, 2002.

Moran, et al, (2001) Thiols in cellular redox signalling and control. Curr Med Chem 8, 763-772.

Mukai, (2004) Evidence that the gene encoding ZDHHC8 contributes to the risk of schizophrenia. Nat Genet 36, 725-731.

Ohata, (1993), (1993) Deletion mapping of the short arm of chromosome 8 in non-small cell lung carcinoma. Genes Chromosomes Cancer 7, 85-88.

Wedegaertner, et al Activation and depalmitoylation of Gs alpha. Cell 77, 1063-1070, Jul. 1, 1994.

Schweizer, et al, Retention of p63 in an ER-Golgi intermediate compartment depends on the presence of all three of its domains and on its ability to form oligomers, J. Cell Biol 126, 25-39, Jul. 1, 1994.

Schweizer et al. (1993) a reversibly palmitoylated resident protein (p63) of an ER-Golgi intermediate compartment is related to a circulatory shock resuscitation protein. J Cell Sci 104 (Pt3), 685-694.

Smotrys, et al (2004) Palmitoylation of intracellular signaling proteins; regulation and function. Annu Rev Biochem 73, 559-587.

Schweizer, et al (1995) Reassessment of the subcellular localization of p63. J Cell Sci 108 (Pt 6), 2477-2485.

Shaner, et al, Improved monomeric red, orange and yellow fluorescent proteins derived from *Discosoma* sp. red fluorescent protein, Nature biotechnology, vol. 22, No. 12, Dec. 2004.

Baird, et al. Biochemistry, mutagenesis, and oligomerization of DsRed, a red fluorescent protein from coral, Department of Pharmacology, vol. 97, No. 22, 11984-11989, Oct. 24, 2000.

Baird, et al. Circular permutation and receptor insertion within green fluorescent proteins, Proc. Natl, Acad. Sci. USA, vol. 96,pp. 11241-11246, Sep. 1999.

Griesbeck, et al. Reducing the Environmental Sensitivity of Yellow Fluorescent Protein, The Journal of Biological Chemistry, vol. 276, No. 31, Issue of Aug. 3, 2001, pp. 29188-29194.

Campbell, et al. A monomeric red fluorescent protein, Departments of Pharmacology and Chemistry and biochemistry, vol. 99, No. 12, Jun. 11, 2002, pp. 7877-7882.

Knowles, et al., Deletion mapping of chromosome 8 in cancers of the urinary bladder using restriction fragment length polymorphisms and microsatellite polymorphisms, Oncogene (1993) 8, 1357-1364.

Baeummer, et al A. A Universal Nucleic Acid Sequence Biosensor with Nanomolar Detection Limits, Analytical Chemistry, vol. 76, No. 4, Feb. 15, 2004.

Fernandez, J.M. & Hoeffler, J.P., Protein Expression and Purification Core Facility Cloning, Academic Press, San Diego, 1999.

* cited by examiner

Figure 1. CKAP4:YFP construct
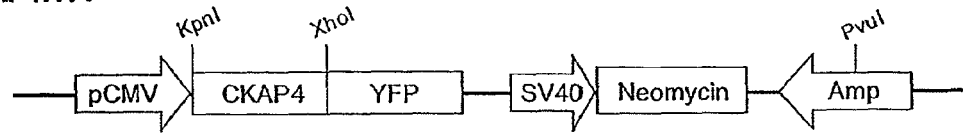

Figure 2. Transiently expressed CKAP4:YFP translocates to the nucleus after application of synthetic APF.
CKAP4:YFP Transient Expression in HeLa Cells Prior to Applying APF
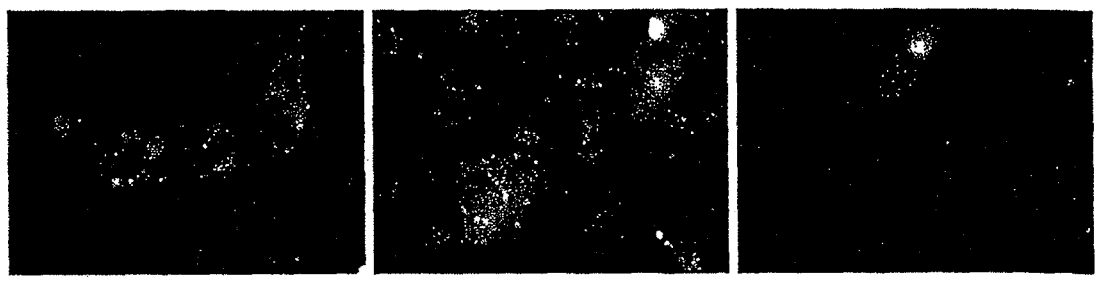
CKAP4:YFP Transient Expression in HeLa Cells After Applying APF
phase　　　　　　　　YFP　　　　　　　　overlay
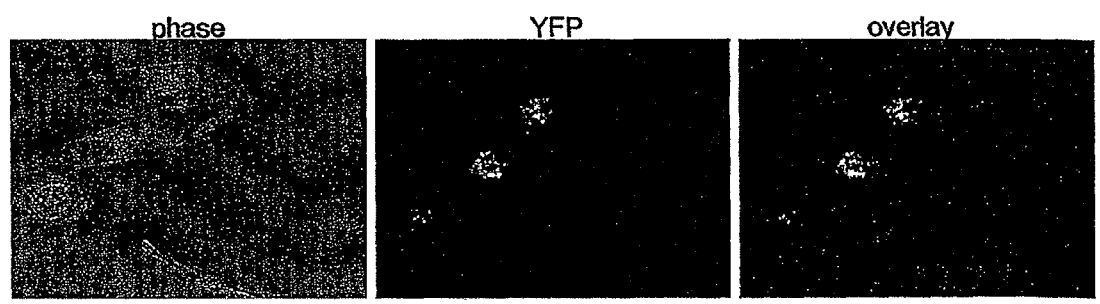

Figure 3. Localization of endogenous CKAP4 in the absence (A) or presence (B) of APF (US Provisional Patent #P03444US1, Figure 7B; International Provisional Patent#P03444W00, Figure 7B).
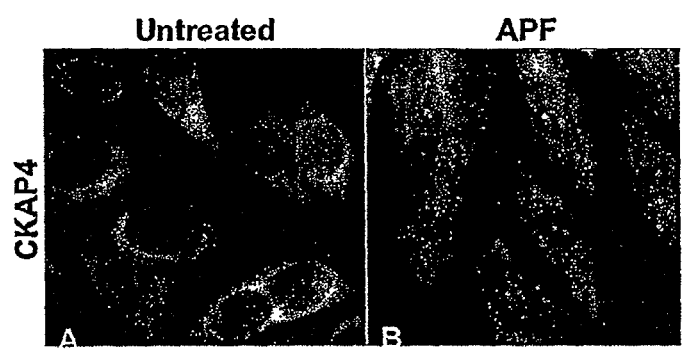

Figure 4. CKAP4 abundance is increased in nuclear fractions from APF treated HeLa cells. In HeLa cells treated with APF, we observed a 5-fold increase in the abundance of CKAP4 in the nucleus versus untreated cells as determined by Western blot.
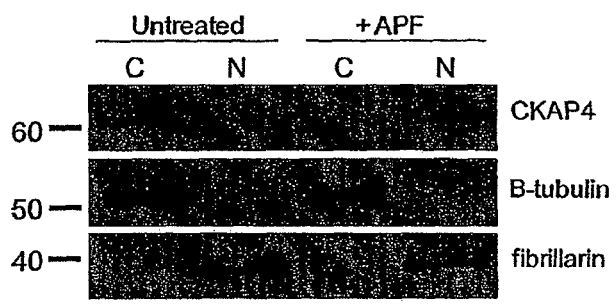
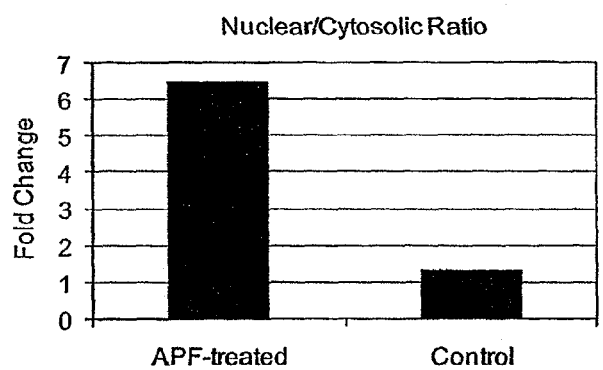

Figure 5. Schematic diagram of the APF diagnostic assay
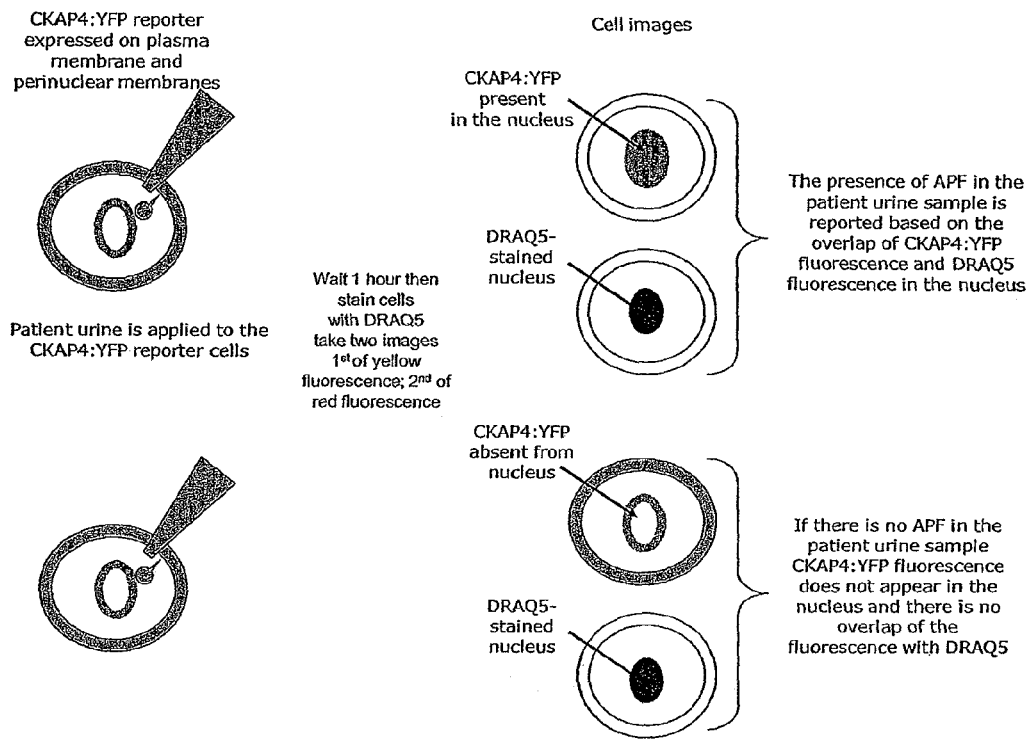

Figure 6
6A
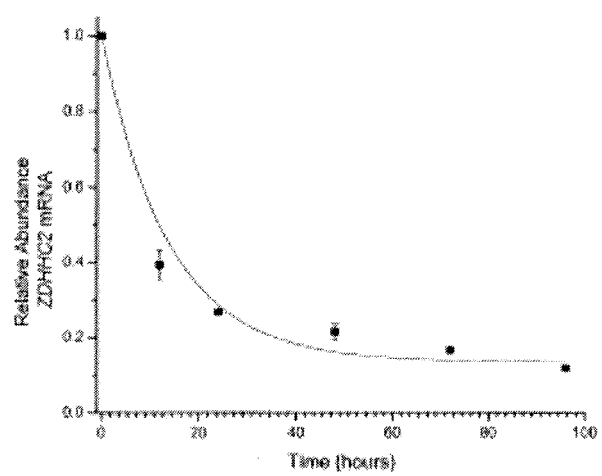
6B
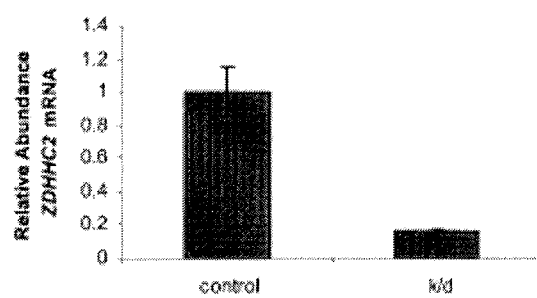
6C
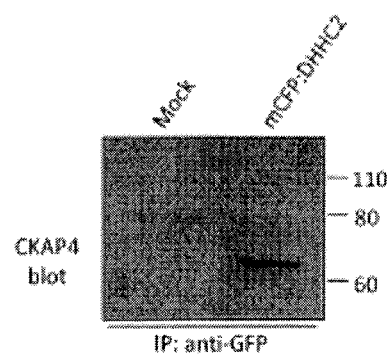

Figure 9
9A
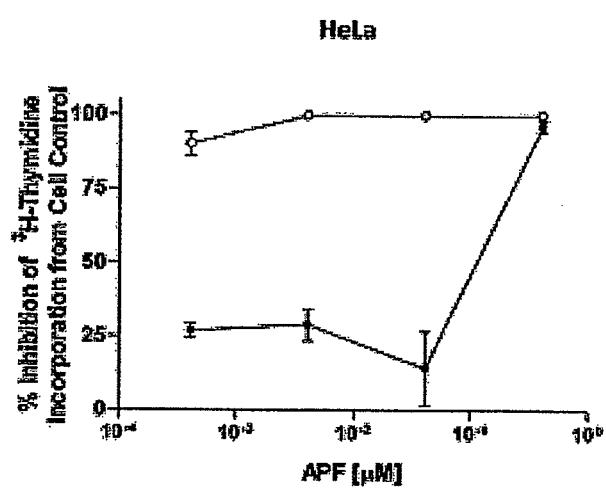
9B
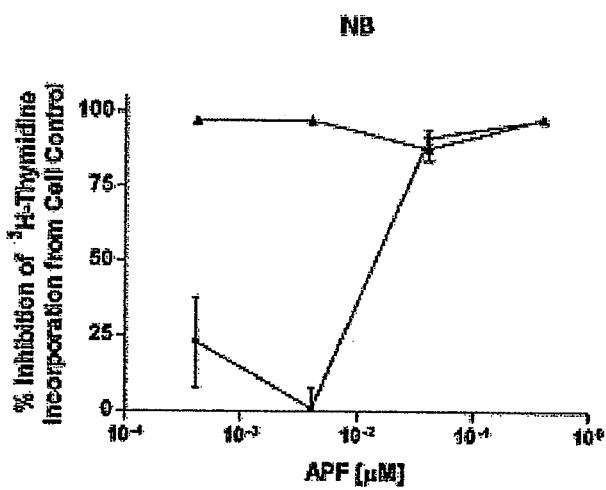

Figure 10
10A
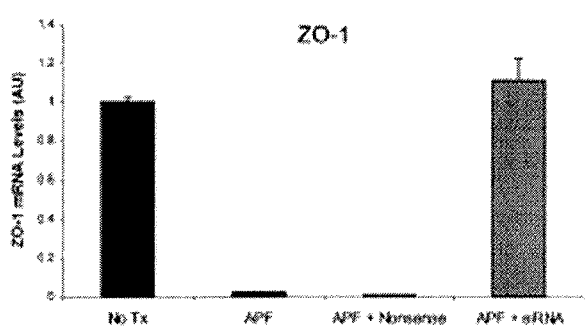
10B
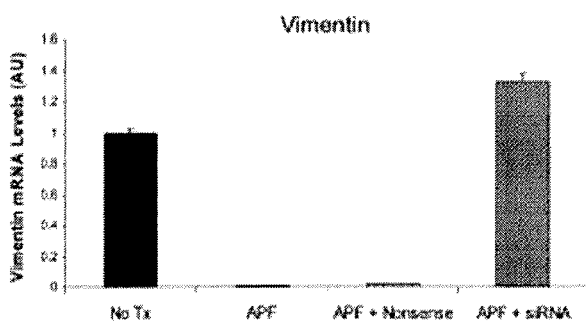
10C
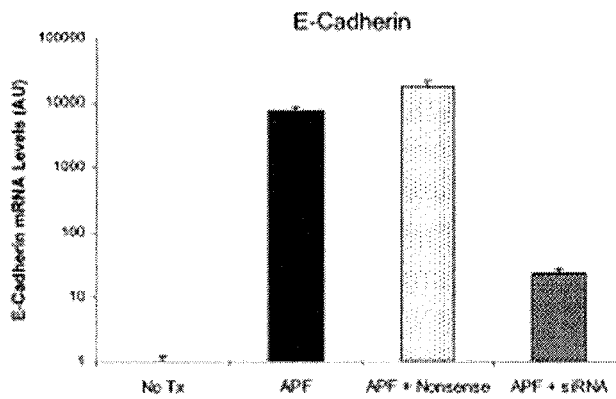

Figure 11
11A
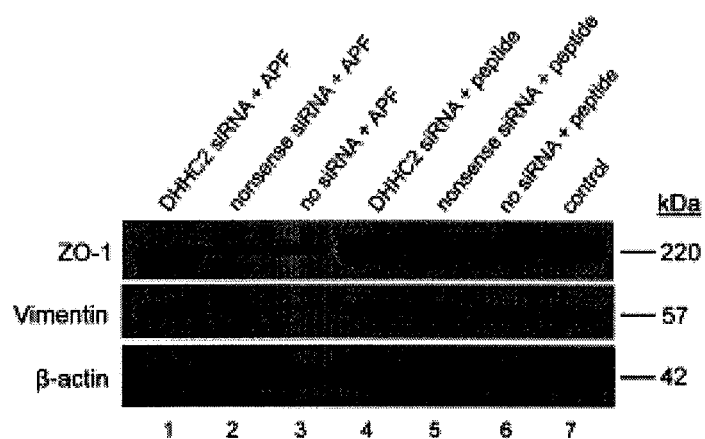
11B
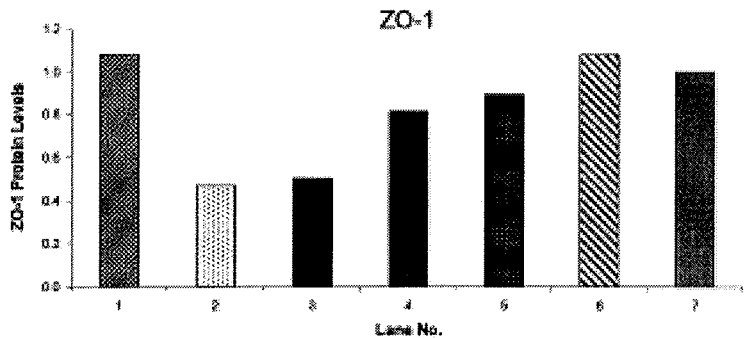
11C
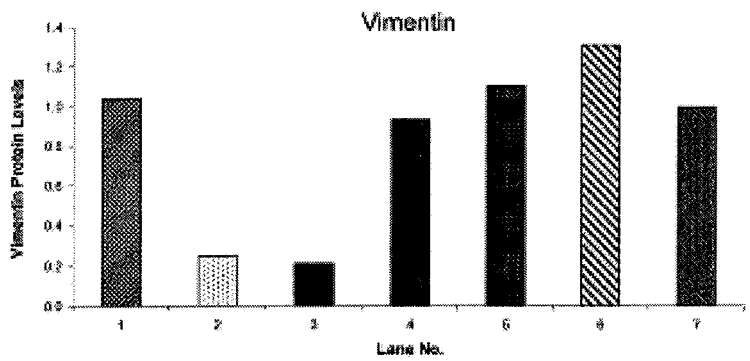

Figure 12
12A
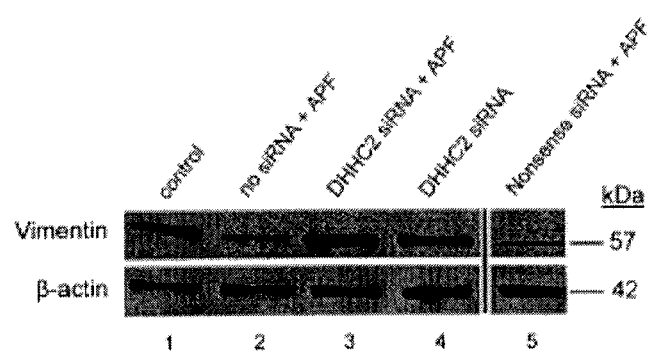
12B
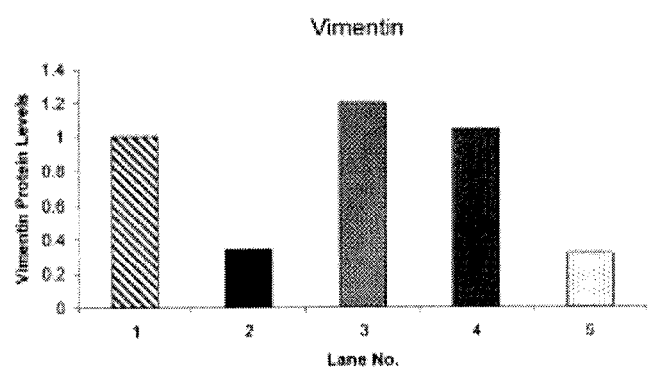

Figure 13
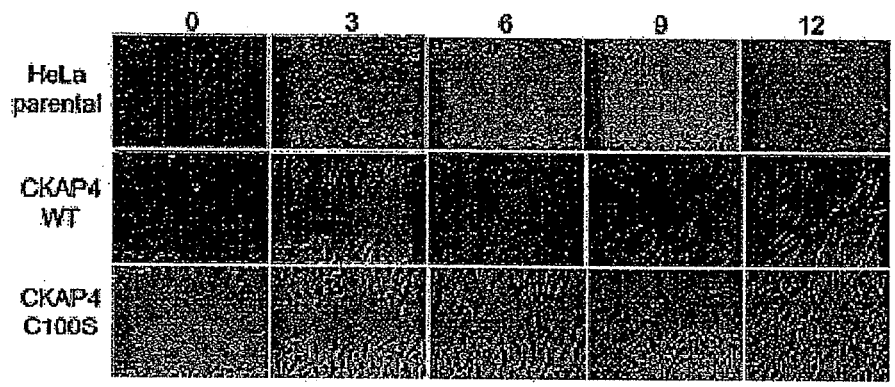
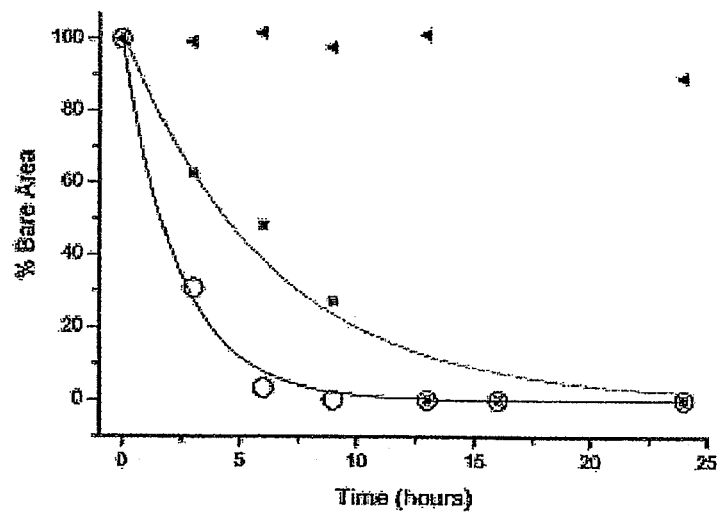

www.ebi.ac.uk/astd/geneview.html?acc=ENSG00000136026

Multiple alignment of CKAP4 proteins that result from alternative splicing

```
ENSP00000258512      -----aRsppsprpeppPrppcprPnkGApraAtaPraprRRvPtrrAarmtwrrsRrrR
ENSP00000367265      MPSAKQRGSKGGHGAASPSEKgAHPSGGADDgAq---------------------------
ENSP00000312296      MPSAKQRGSKGGHGAASPSEKgAHPSGGADDvAkkPppapQQpPpppAphpqqhpqQhpQ ENSP00000258512      rsSrrRrprR------tRSSTrSStrrtrrtArAATAAAaAaaLGRALNFLFYLAlvAAA
ENSP00000367265      --------------------------------------------------LslLprpAAA
ENSP00000312296      nqAhgKgghRgggggggKSSSsSSasaaaaaAaASSSAScSrrLGRALNFLFYLAlvAAA ENSP00000258512      AFSGWCVHHVLEEVQQVRRSHQDFSRQREELGQGLQGVEQKVQSLQATFGTFESILRSSQ
ENSP00000367265      AFSGWCVHHVLEEVQQVRRSHQDFSRQREELGQGLQGVEQKVQSLQATFGTFESILRSSQ
ENSP00000312296      AFSGWCVHHVLEEVQQVRRSHQDFSRQREELGQGLQGVEQKVQSLQATFGTFESILRSSQ ENSP00000258512      HKQDLTEKAVKQGESEVSRISEVLQKLQNEILKDLSDGIHVVKDARERDFTSLENTVEER
ENSP00000367265      HKQDLTEKAVKQGESEVSRISEVLQKLQNEILKDLSDGIHVVKDARERDFTSLENTVEER
ENSP00000312296      HKQDLTEKAVKQGESEVSRISEVLQKLQNEILKDLSDGIHVVKDARERDFTSLENTVEER ENSP00000258512      LTELTKSINDNIAIFTEVQKRSQKEINDMKAKVASLEESEGNKQDLKALKEAVKEIQTSA
ENSP00000367265      LTELTKSINDNIAIFTEVQKRSQKEINDMKAKVASLEESEGNKQDLKALKEAVKEIQTSA
ENSP00000312296      LTELTKSINDNIAIFTEVQKRSQKEINDMKAKVASLEESEGNKQDLKALKEAVKEIQTSA ENSP00000258512      KSREWDMEALRSTLQTMESDIYTEVRELVSLKQEQQAFKEAADTERLALQALTEKLLRSE
ENSP00000367265      KSREWDMEALRSTLQTMESDIYTEVRELVSLKQEQQAFKEAADTERLALQALTEKLLRSE
ENSP00000312296      KSREWDMEALRSTLQTMESDIYTEVRELVSLKQEQQAFKEAADTERLALQALTEKLLRSE ENSP00000258512      ESVSRLPEEIRRLEEELRQLKSDSHGPKEDGGFRHSEAFEALQQKSQGLDSRLQHVEDGV
ENSP00000367265      ESVSRLPEEIRRLEEELRQLKSDSHGPKEDGGFRHSEAFEALQQKSQGLDSRLQHVEDGV
ENSP00000312296      ESVSRLPEEIRRLEEELRQLKSDSHGPKEDGGFRHSEAFEALQQKSQGLDSRLQHVEDGV ENSP00000258512      LSMQVASARQTESLESLLSKSQEHEQRLAALQGRLEGLGSSEADQDGLASTVRSLGETQL
ENSP00000367265      LSMQVASARQTESLESLLSKSQEHEQRLAALQGRLEGLGSSEADQDGLASTVRSLGETQL
ENSP00000312296      LSMQVASARQTESLESLLSKSQEHEQRLAALQGRLEGLGSSEADQDGLASTVRSLGETQL ENSP00000258512      VLYGDVEELKRSVGELPSTVESLQKVQEQVHTLLSQDQAQAARLPPQDFLDRLSSLDNLK
ENSP00000367265      VLYGDVEELKRSVGELPSTVESLQKVQEQVHTLLSQDQAQAARLPPQDFLDRLSSLDNLK
ENSP00000312296      VLYGDVEELKRSVGELPSTVESLQKVQEQVHTLLSQDQAQAARLPPQDFLDRLSSLDNLK ENSP00000258512      ASVSQVEADLKMLRTAVDSLVAYSVKIETNENNLESAKGLLDDLRNDLDRLFVKVEKIHE
ENSP00000367265      ASVSQVEADLKMLRTAVDSLVAYSVKIETNENNLESAKGLLDDLRNDLDRLFVKVEKIHE
ENSP00000312296      ASVSQVEADLKMLRTAVDSLVAYSVKIETNENNLESAKGLLDDLRNDLDRLFVKVEKIHE

ENSP00000258512      KV
ENSP00000367265      KV
ENSP00000312296      KV

Sequence alignments of CKAP4 cDNAs that are alternatively spliced
ENST00000308387      ----------------------------------------------ATGCCCTCGGCCA
ENST00000378026      ----------------------------------------------ATGCCCTCGGCCA
ENST00000258512      gctcgctcgcctcccagcccgcggcccgagccgccgccgcgcccgccATGCCCTCGGCCA ENST00000308387      AACAAAGGGGCTCCAAGGGCGGCCACGGCGCCGCGAGCCCCTCGGAGAAGGGTGCCCACC
ENST00000378026      AACAAAGGGGCTCCAAGGGCGGCCACGGCGCCGCGAGCCCCTCGGAGAAGGGTGCCCACC
ENST00000258512      AACAAAGGGGCTCCAAGGGCGGCCACGGCGCCGCGAGCCCCTCGGAGAAGGGTGCCCACC ENST00000308387      CGTCGGGCGGCGCGGATGACGTGGCGAAGAAGCCGCCGCCGGCGCCGCAGCAGCCGCCGC
ENST00000378026      CGTCGGGCGGCGCGGATGAC-----------------------------------------
ENST00000258512      CGTCGGGCGGCGCGGATGACGTGGCGAAGAAGCCGCCGCCGGCGCCGCAGCAGCCGCCGC ENST00000308387      CGCCGCCCGCGCCGCACCCGCAGCAGCACCCGCAGCAGCACCCGCAGAACCAGGCGCACG
ENST00000378026      ------------------------------------------------------------
ENST00000258512      CGCCGCCCGCGCCGCACCCGCAGCAGCACCCGCAGCAGCACCCGCAGAACCAGGCGCACG
```

Figure 15(B) (continued)

```
ENST00000308387    GCAAGGGCGGCCACCGCGGCGGCGGCGGCGGCGGCggcaagtcctcctcctcctcctccg
ENST00000378026    ------------------------------------------------------------
ENST00000258512    GCAAGGGCGGCCACCGCGGCGGCGGCGGCGGCGGC--------------------------

ENST00000308387    cctccgccgccgctgccgccgccgccgcctcgtcctcggcgtcctgctcgcgcagGCTCG
ENST00000378026    ------------------------------------------------------------
ENST00000258512    -------------------------------------------------------GCTCG ENST00000308387    GCAGGGCGCTCAACTTTCTCTTCTACCTCGCCCTGGTGGCGGCGGCCGCTTTCTCGGGCT
ENST00000378026    ----GGCGCTCAACTTTCTCTTCTACCTCGCCCT----GCGGCGGCCGCTTTCTCGGGCT
ENST00000258512    GCAGGGCGCTCAACTTTCTCTTCTACCTCGCCCTGGTGGCGGCGGCCGCTTTCTCGGGCT ENST00000308387    GGTGCGTCCACCACGTCCTGGAGGAGGTCCAGCAGGTCCGGCGCAGCCACCAGGACTTCT
ENST00000378026    GGTGCGTCCACCACGTCCTGGAGGAGGTCCAGCAGGTCCGGCGCAGCCACCAGGACTTCT
ENST00000258512    GGTGCGTCCACCACGTCCTGGAGGAGGTCCAGCAGGTCCGGCGCAGCCACCAGGACTTCT ENST00000308387    CCCGGCAGAGGGAGGAGCTGGGCCAGGGCTTGCAGGGCGTCGAGCAGAAGGTGCAGTCTT
ENST00000378026    CCCGGCAGAGGGAGGAGCTGGGCCAGGGCTTGCAGGGCGTCGAGCAGAAGGTGCAGTCTT
ENST00000258512    CCCGGCAGAGGGAGGAGCTGGGCCAGGGCTTGCAGGGCGTCGAGCAGAAGGTGCAGTCTT ENST00000308387    TGCAAGCCACATTTGGAACTTTTGAGTCCATCTTGAGAAGCTCCCAACATAAACAAGACC
ENST00000378026    TGCAAGCCACATTTGGAACTTTTGAGTCCATCTTGAGAAGCTCCCAACATAAACAAGACC
ENST00000258512    TGCAAGCCACATTTGGAACTTTTGAGTCCATCTTGAGAAGCTCCCAACATAAACAAGACC ENST00000308387    TCACAGAGAAAGCTGTGAAGCAAGGGGAGAGTGAGGTCAGCCGGATCAGCGAAGTGCTGC
ENST00000378026    TCACAGAGAAAGCTGTGAAGCAAGGGGAGAGTGAGGTCAGCCGGATCAGCGAAGTGCTGC
ENST00000258512    TCACAGAGAAAGCTGTGAAGCAAGGGGAGAGTGAGGTCAGCCGGATCAGCGAAGTGCTGC ENST00000308387    AGAAACTCCAGAATGAGATTCTCAAAGACCTCTCGGATGGGATCCATGTGGTGAAGGACG
ENST00000378026    AGAAACTCCAGAATGAGATTCTCAAAGACCTCTCGGATGGGATCCATGTGGTGAAGGACG
ENST00000258512    AGAAACTCCAGAATGAGATTCTCAAAGACCTCTCGGATGGGATCCATGTGGTGAAGGACG ENST00000308387    CCCGGGAGCGGGACTTCACGTCCCTGGAGAACACGGTGGAGGAGCGGCTGACGGAGCTCA
ENST00000378026    CCCGGGAGCGGGACTTCACGTCCCTGGAGAACACGGTGGAGGAGCGGCTGACGGAGCTCA
ENST00000258512    CCCGGGAGCGGGACTTCACGTCCCTGGAGAACACGGTGGAGGAGCGGCTGACGGAGCTCA ENST00000308387    CCAAATCCATCAACGACAACATCGCCATCTTCACAGAAGTCCAGAAGAGGAGCCAGAAGG
ENST00000378026    CCAAATCCATCAACGACAACATCGCCATCTTCACAGAAGTCCAGAAGAGGAGCCAGAAGG
ENST00000258512    CCAAATCCATCAACGACAACATCGCCATCTTCACAGAAGTCCAGAAGAGGAGCCAGAAGG ENST00000308387    AGATCAATGACATGAAGGCAAAGGTTGCCTCCCTGGAAGAATCTGAGGGGAACAAGCAGG
ENST00000378026    AGATCAATGACATGAAGGCAAAGGTTGCCTCCCTGGAAGAATCTGAGGGGAACAAGCAGG
ENST00000258512    AGATCAATGACATGAAGGCAAAGGTTGCCTCCCTGGAAGAATCTGAGGGGAACAAGCAGG ENST00000308387    ATTTGAAAGCCTTAAAGGAAGCTGTGAAGGAGATACAGACCTCAGCCAAGTCCAGAGAGT
ENST00000378026    ATTTGAAAGCCTTAAAGGAAGCTGTGAAGGAGATACAGACCTCAGCCAAGTCCAGAGAGT
ENST00000258512    ATTTGAAAGCCTTAAAGGAAGCTGTGAAGGAGATACAGACCTCAGCCAAGTCCAGAGAGT ENST00000308387    GGGACATGGAGGCCCTGAGAAGTACCCTTCAGACTATGGAGTCTGACATCTACACCGAGG
ENST00000378026    GGGACATGGAGGCCCTGAGAAGTACCCTTCAGACTATGGAGTCTGACATCTACACCGAGG
ENST00000258512    GGGACATGGAGGCCCTGAGAAGTACCCTTCAGACTATGGAGTCTGACATCTACACCGAGG ENST00000308387    TCCGCGAGCTGGTGAGCCTCAAGCAGGAGCAGCAGGCTTTCAAGGAGGCGGCCGACACGG
ENST00000378026    TCCGCGAGCTGGTGAGCCTCAAGCAGGAGCAGCAGGCTTTCAAGGAGGCGGCCGACACGG
ENST00000258512    TCCGCGAGCTGGTGAGCCTCAAGCAGGAGCAGCAGGCTTTCAAGGAGGCGGCCGACACGG ENST00000308387    AGCGGCTCGCCCTGCAGGCCCTCACGGAGAAGCTTCTCAGGTCTGAGGAGTCCGTCTCCC
ENST00000378026    AGCGGCTCGCCCTGCAGGCCCTCACGGAGAAGCTTCTCAGGTCTGAGGAGTCCGTCTCCC
ENST00000258512    AGCGGCTCGCCCTGCAGGCCCTCACGGAGAAGCTTCTCAGGTCTGAGGAGTCCGTCTCCC ENST00000308387    GCCTCCCGGAGGAGATCCGGAGACTGGAGGAAGAGCTCCGCCAGCTGAAGTCCGATTCCC
ENST00000378026    GCCTCCCGGAGGAGATCCGGAGACTGGAGGAAGAGCTCCGCCAGCTGAAGTCCGATTCCC
ENST00000258512    GCCTCCCGGAGGAGATCCGGAGACTGGAGGAAGAGCTCCGCCAGCTGAAGTCCGATTCCC ENST00000308387    ACGGGCCGAAGGAGGACGGAGGCTTCAGACACTCGGAAGCCTTTGAGGCACTCCAGCAAA
ENST00000378026    ACGGGCCGAAGGAGGACGGAGGCTTCAGACACTCGGAAGCCTTTGAGGCACTCCAGCAAA
ENST00000258512    ACGGGCCGAAGGAGGACGGAGGCTTCAGACACTCGGAAGCCTTTGAGGCACTCCAGCAAA
```

Figure 15(C) (continued)

| | |
|---|---|
| ENST00000308387 | AGAGTCAGGGACTGGACTCCAGGCTCCAGCACGTGGAGGATGGGGTGCTCTCCATGCAGG |
| ENST00000378026 | AGAGTCAGGGACTGGACTCCAGGCTCCAGCACGTGGAGGATGGGGTGCTCTCCATGCAGG |
| ENST00000258512 | AGAGTCAGGGACTGGACTCCAGGCTCCAGCACGTGGAGGATGGGGTGCTCTCCATGCAGG |
| | |
| ENST00000308387 | TGGCTTCTGCGCGCCAGACCGAGAGCCTGGAGTCCCTCCTGTCCAAGAGCCAGGAGCACG |
| ENST00000378026 | TGGCTTCTGCGCGCCAGACCGAGAGCCTGGAGTCCCTCCTGTCCAAGAGCCAGGAGCACG |
| ENST00000258512 | TGGCTTCTGCGCGCCAGACCGAGAGCCTGGAGTCCCTCCTGTCCAAGAGCCAGGAGCACG |
| | |
| ENST00000308387 | AGCAGCGCCTGGCCGCCCTGCAGGGGCGCCTGGAAGGCCTCGGGTCCTCAGAGGCAGACC |
| ENST00000378026 | AGCAGCGCCTGGCCGCCCTGCAGGGGCGCCTGGAAGGCCTCGGGTCCTCAGAGGCAGACC |
| ENST00000258512 | AGCAGCGCCTGGCCGCCCTGCAGGGGCGCCTGGAAGGCCTCGGGTCCTCAGAGGCAGACC |
| | |
| ENST00000308387 | AGGATGGCCTGGCCAGCACGGTGAGGAGCCTGGGCGAGACCCAGCTGGTGCTCTACGGTG |
| ENST00000378026 | AGGATGGCCTGGCCAGCACGGTGAGGAGCCTGGGCGAGACCCAGCTGGTGCTCTACGGTG |
| ENST00000258512 | AGGATGGCCTGGCCAGCACGGTGAGGAGCCTGGGCGAGACCCAGCTGGTGCTCTACGGTG |
| | |
| ENST00000308387 | ACGTGGAGGAGCTGAAGAGGAGTGTGGGCGAGCTCCCCAGCACCGTGGAATCACTCCAGA |
| ENST00000378026 | ACGTGGAGGAGCTGAAGAGGAGTGTGGGCGAGCTCCCCAGCACCGTGGAATCACTCCAGA |
| ENST00000258512 | ACGTGGAGGAGCTGAAGAGGAGTGTGGGCGAGCTCCCCAGCACCGTGGAATCACTCCAGA |
| | |
| ENST00000308387 | AGGTGCAGGAGCAGGTGCACACGCTGCTCAGTCAGGACCAAGCCCAGGCCGCCCGTCTGC |
| ENST00000378026 | AGGTGCAGGAGCAGGTGCACACGCTGCTCAGTCAGGACCAAGCCCAGGCCGCCCGTCTGC |
| ENST00000258512 | AGGTGCAGGAGCAGGTGCACACGCTGCTCAGTCAGGACCAAGCCCAGGCCGCCCGTCTGC |
| | |
| ENST00000308387 | CTCCTCAGGACTTCCTGGACAGACTTTCTTCTCTAGACAACCTGAAAGCCTCAGTCAGCC |
| ENST00000378026 | CTCCTCAGGACTTCCTGGACAGACTTTCTTCTCTAGACAACCTGAAAGCCTCAGTCAGCC |
| ENST00000258512 | CTCCTCAGGACTTCCTGGACAGACTTTCTTCTCTAGACAACCTGAAAGCCTCAGTCAGCC |
| | |
| ENST00000308387 | AAGTGGAGGCGGACTTGAAAATGCTCAGGACTGCTGTGGACAGTTTGGTTGCATACTCGG |
| ENST00000378026 | AAGTGGAGGCGGACTTGAAAATGCTCAGGACTGCTGTGGACAGTTTGGTTGCATACTCGG |
| ENST00000258512 | AAGTGGAGGCGGACTTGAAAATGCTCAGGACTGCTGTGGACAGTTTGGTTGCATACTCGG |
| | |
| ENST00000308387 | TCAAAATAGAAACCAACGAGAACAATCTGGAATCAGCCAAGGGTTTACTAGATGACCTGA |
| ENST00000378026 | TCAAAATAGAAACCAACGAGAACAATCTGGAATCAGCCAAGGGTTTACTAGATGACCTGA |
| ENST00000258512 | TCAAAATAGAAACCAACGAGAACAATCTGGAATCAGCCAAGGGTTTACTAGATGACCTGA |
| | |
| ENST00000308387 | GGAATGATCTGGATAGGTTGTTTGTGAAAGTGGAGAAGATTCACGAAAAGGTCTAA |
| ENST00000378026 | GGAATGATCTGGATAGGTTGTTTGTGAAAGTGGAGAAGATTCACGAAAAGGTCTAA |
| ENST00000258512 | GGAATGATCTGGATAGGTTGTTTGTGAAAGTGGAGAAGATTCACGAAAAGGTCTAA |

Figure 16(A)

A: 97770      Reports     BLink, Links
cytoskeleton-associated protein 4, isoform CRA_a [Homo sapiens]
gi|119618176|gb|EAW97770.1|[119618176]

B: BAD97283      Reports     BLink, Conserved Domains, Links
cytoskeleton-associated protein 4 variant [Homo sapiens]
gi|62898858|dbj|BAD97283.1|[62898858]

C: NP_006816      Reports     BLink, Conserved Domains, Links
cytoskeleton-associated protein 4 [Homo sapiens]
gi|19920317|ref|NP_006816.2|[19920317]

CLUSTAL W (1.82) multiple sequence alignment

```
seqA        MPSAKQRGSKGGHGAASPSEKGAHPSGGADDVAKKPPPAPQQPPPPPAPHPQQHPQQHPQ
seqB        MPSAKQRGSKGGHGAASPSEKGAHPSGGADDVAKKPPPAPQQPPPPPAPHPQQHPQQHPR
seqC        MPSAKQRGSKGGHGAASPSEKGAHPSGGADDVAKKPPPAPQQPPPPPAPHPQQHPQQHPQ
            ************************************************************:

seqA        NQAHGKGGHRGGGGGGGKSSSSSSASAAAAAAAASSSASCSRRLGRALNFLFYLALVAAA
seqB        NQAHGKGGHRGGGGGGGKSSSSSSASAAAAAAAASSSASCSRRLGRALNFLFYLALVAAA
seqC        NQAHGKGGHRGGGGGGGKSSSSSSASAAAAAAAASSSASCSRRLGRALNFLFYLALVAAA
            ************************************************************ seqA        AFSGWCVHHVLEEVQQVRRSHQDFSRQREELGQGLQGVEQKVQSLQATFGTFESILRSSQ
seqB        AFSGWCVHHVLEEVQQVRRSHQDFSRQREELGQGLQGVEQKVQSLQATFGTFESILRSSQ
seqC        AFSGWCVHHVLEEVQQVRRSHQDFSRQREELGQGLQGVEQKVQSLQATFGTFESILRSSQ
            ************************************************************ seqA        HKQDLTEKAVKQGESEVSRISEVLQKLQNEILKDLSDGIHVVKDARERDFTSLENTVEER
seqB        HKQDLTEKAVKQGESEVSRISEVLQKLQNEILKDLSDGIHVVKDARERDFTSLENTVEER
seqC        HKQDLTEKAVKQGESEVSRISEVLQKLQNEILKDLSDGIHVVKDARERDFTSLENTVEER
            ************************************************************ seqA        LTELTKSINDNIAIFTES------------------------------------------
seqB        LTELTKSINDNIAIFTEVQKRSQKEINDMKAKVASLEESEGNKQDLKALKEAVKEIQTSA
seqC        LTELTKSINDNIAIFTEVQKRSQKEINDMKAKVASLEESEGNKQDLKALKEAVKEIQTSA
            ***************** seqA        ------------------------------------------------------------
seqB        KSREWDMEALRSTLQTMESDIYTEVRELVSLKQEQQAFKEAADTERLALQALTEKLLRSE
seqC        KSREWDMEALRSTLQTMESDIYTEVRELVSLKQEQQAFKEAADTERLALQALTEKLLRSE seqA        ------------------------------------------------------------
seqB        ESVSRLPEEIRRLEEELRQLKSDSHGPKEDGGFRHSEAFEALQQKSQGLDSRLQHVEDGV
seqC        ESVSRLPEEIRRLEEELRQLKSDSHGPKEDGGFRHSEAFEALQQKSQGLDSRLQHVEDGV seqA        -----------------LLSKSQEHEQRLAALQGRLEGLGSSEADQDGLASTVRSLGETQL
seqB        LSMQVASARQTESLESLLSKSQEHEQRLAALQGRLEGLGSSEADQDGLASTVRSLGETQL
seqC        LSMQVASARQTESLESLLSKSQEHEQRLAALQGRLEGLGSSEADQDGLASTVRSLGETQL
                             ******************************************* seqA        VLYGDVEELKRSVGELPSTVESLQKVQEQVHTLLSQDQAQAARLPPQDFLDRLSSLDNLK
seqB        VLYGDVEELKRSVGELPSTVESLQKVQEQVHTLLSQDQAQAARLPPQDFLDRLSSLDNLK
seqC        VLYGDVEELKRSVGELPSTVESLQKVQEQVHTLLSQDQAQAARLPPQDFLDRLSSLDNLK
            ************************************************************ seqA        ASVSQVEADLKMLRTAVDSLVAYSVKIETNENNLESAKGLLDDLRNDLDRLFVKVEKIHE
seqB        ASVSQVEADLKMLRTAVDSLVAYSVKIETNENNLESAKGLLDDLRNDLDRLFVKVEKIHE
seqC        ASVSQVEADLKMLRTAVDSLVAYSVKIETNENNLESAKGLLDDLRNDLDRLFVKVEKIHE
            ************************************************************ seqA        KV (SEQ ID NO: 14)
seqB        KV (SEQ ID NO: 15)
seqC        KV (SEQ ID NO: 16)
```

Figure 16(B)

DNA sequence alignment

A: NM_006825    Reports    Links
Homo sapiens cytoskeleton-associated protein 4 (CKAP4), mRNA
gi|19920316|ref|NM_006825.2|[19920316]

B: BC082972    Reports    Order cDNA clone, Links
Homo sapiens cytoskeleton-associated protein 4, mRNA (cDNA clone MGC:99554 IMAGE:6084968), complete cds
gi|52789252|gb|BC082972.1|[52789252]

C: BC094824    Reports    Order cDNA clone, Links
Homo sapiens cytoskeleton-associated protein 4, mRNA (cDNA clone MGC:104815 IMAGE:6374931), complete cds
gi|63102282|gb|BC094824.1|[63102282]

```
CLUSTAL W (1.82) multiple sequence alignment seqA            ------------------------GGGGGAGCCCCTGCAAGTTTCCCGGGCCGCGCGCCGCGC
seqB            ---------------------------AGCC-----AA------TGGG----------GC
seqC            GCGTGCCGCTCGCCCAGTCCCGGGGGAGCCCCTGCAAGTTTCCCGGGCCGCGCGCCGCGC
                                           ****      **       ***           **
                                                                       start
seqA            TCGCTCGCCTCCCAGCCCGCGGCCCGAGCCGCCGCCGCGCCCGCC   CCCTCGGCCAAA
seqB            TCGCTCGCCTCCCAGCCCGCGGCCCGAGCCGCCGCCGCGCCCGCC   CCCTCGGCCAAA
seqC            TCGCTCGCCTCCCAGCCCGCGGCCCGAGCCGCCGCCGCGCCCGCC   CCCTCGGCCAAA
                *******************************************  ********** seqA            CAAAGGGGCTCCAAGGGCGGCCACGGCGCCGCGAGCCCCTCGGAGAAGGGTGCCCACCCG
seqB            CAAAGGGGCTCCAAGGGCGGCCACGGCGCCGCGAGCCCCTCGGAGAAGGGTGCCCACCCG
seqC            CAAAGGGGCTCCAAGGGCGGCCACGGCGCCGCGAGCCCCTCGGAGAAGGGTGCCCACCCG
                ************************************************************ seqA            TCGGGCGGCGCGGATGACGTGGCGAAGAAGCCGCCGCCGGCGCCGCAGCAGCCGCCGCCG
seqB            TCGGGCGGCGCGGATGACGTGGCGAAGAAGCCGCCGCCGGCGCCGCAGCAGCCGCCGCCG
seqC            TCGGGCGGCGCGGATGACGTGGCGAAGAAGCCGCCGCCGGCG------------------
                ****************************************** seqA            CCGCCCGCGCCGCACCCGCAGCAGCACCCGCAGCAGCACCCGCAGAACCAGGCGCACGGC
seqB            CCGCCCGCGCCGCACCCGCAGCAGCACCCGCAGCAGCACCCGCAGAACCAGGCGCACGGC
seqC            ------------------------------------------------------------ seqA            AAGGGCGGCCACCGCGGCGGCGGCGGCGGCGGCGGCAAGTCCTCCTCCTCCTCCTCCGCC
seqB            AAGGGCGGCCACCGCGGCGGCGGCGGCGGCGGCGGCAAGTCCTCCTCCTCCTCCTCCGCC
seqC            ------------------------------------------------------------ seqA            TCCGCCGCCGCTGCCGCCGCCGCCGCCTCGTCCTCGGCGTCCTGCTCGCGCAGGCTCGGC
seqB            TCCGCCGCCGCTGCCGCCGCCGCCGCCTCGTCCTCGGCGTCCTGCTCGCGCAGGCTCGGC
seqC            ------------------------------------------------------------ seqA            AGGGCGCTCAACTTTCTCTTCTACCTCGCCCTGGTGGCGGCGGCCGCTTTCTCGGGCTGG
seqB            AGGGCGCTCAACTTTCTCTTCTACCTCGCCCTGGTGGCGGCGGCCGCTTTCTCGGGCTGG
seqC            ------------------------------------GCCGCTTTCTCGGGCTGG
                                                    ****************** seqA            TGCGTCCACCACGTCCTGGAGGAGGTCCAGCAGGTCCGGCGCAGCCACCAGGACTTCTCC
seqB            TGCGTCCACCACGTCCTGGAGGAGGTCCAGCAGGTCCGGCGCAGCCACCAGGACTTCTCC
seqC            TGCGTCCACCACGTCCTGGAGGAGGTCCAGCAGGTCCGGCGCAGCCACCAGGACTTCTCC
                ************************************************************ seqA            CGGCAGAGGGAGGAGCTGGGCCAGGGCTTGCAGGGCGTCGAGCAGAAGGTGCAGTCTTTG
seqB            CGGCAGAGGGAGGAGCTGGGCCAGGGCTTGCAGGGCGTCGAGCAGAAGGTGCAGTCTTTG
seqC            CGGCAGAGGGAGGAGCTGGGCCAGGGCTTGCAGGGCGTCGAGCAGAAGGTGCAGTCTTTG
                ************************************************************
```

Figure 16(C)

```
seqA    CAAGCCACATTTGGAACTTTTGAGTCCATCTTGAGAAGCTCCCAACATAAACAAGACCTC
seqB    CAAGCCACATTTGGAACTTTTGAGTCCATCTTGAGAAGCTCCCAACATAAACAAGACCTC
seqC    CAAGCCACATTTGGAACTTTTGAGTCCATCTTGAGAAGCTCCCAACATAAACAAGACCTC
        ************************************************************ seqA    ACAGAGAAAGCTGTGAAGCAAGGGGAGAGTGAGGTCAGCCGGATCAGCGAAGTGCTGCAG
seqB    ACAGAGAAAGCTGTGAAGCAAGGGGAGAGTGAGGTCAGCCGGATCAGCGAAGTGCTGCAG
seqC    ACAGAGAAAGCTGTGAAGCAAGGGGAGAGTGAGGTCAGCCGGATCAGCGAAGTGCTGCAG
        ************************************************************ seqA    AAACTCCAGAATGAGATTCTCAAAGACCTCTCGGATGGGATCCATGTGGTGAAGGACGCC
seqB    AAACTCCAGAATGAGATTCTCAAAGACCTCTCGGATGGGATCCATGTGGTGAAGGACGCC
seqC    AAACTCCAGAATGAGATTCTCAAAGACCTCTCGGATGGGATCCATGTGGTGAAGGACGCC
        ************************************************************ seqA    CGGGAGCGGGACTTCACGTCCCTGGAGAACACGGTGGAGGAGCGGCTGACGGAGCTCACC
seqB    CGGGAGCGGGACTTCACGTCCCTGGAGAACACGGTGGAGGAGCGGCTGACGGAGCTCACC
seqC    CGGGAGCGGGACTTCACGTCCCTGGAGAACACGGTGGAGGAGCGGCTGACGGAGCTCACC
        ************************************************************ seqA    AAATCCATCAACGACAACATCGCCATCTTCACAGAAGTCCAGAAGAGGAGCCAGAAGGAG
seqB    AAATCCATCAACGACAACATCGCCATCTTCACAGAAGTCCAGAAGAGGAGCCAGAAGGAG
seqC    AAATCCATCAACGACAACATCGCCATCTTCACAGAAGTCCAGAAGAGGAGCCAGAAGGAG
        ************************************************************ seqA    ATCAATGACATGAAGGCAAAGGTTGCCTCCCTGGAAGAATCTGAGGGGAACAAGCAGGAT
seqB    ATCAATGACATGAAGGCAAAGGTTGCCTCCCTGGAAGAATCTGAGGGGAACAAGCAGGAT
seqC    ATCAATGACATGAAGGCAAAGGTTGCCTCCCTGGAAGAATCTGAGGGGAACAAGCAGGAT
        ************************************************************ seqA    TTGAAAGCCTTAAAGGAAGCTGTGAAGGAGATACAGACCTCAGCCAAGTCCAGAGAGTGG
seqB    TTGAAAGCCTTAAAGGAAGCTGTGAAGGAGATACAGACCTCAGCCAAGTCCAGAGAGTGG
seqC    TTGAAAGCCTTAAAGGAAGCTGTGAAGGAGATACAGACCTCAGCCAAGTCCAGAGAGTGG
        ************************************************************ seqA    GACATGGAGGCCCTGAGAAGTACCCTTCAGACTATGGAGTCTGACATCTACACCGAGGTT
seqB    GACATGGAGGCCCTGAGAAGTACCCTTCAGACTATGGAGTCTGACATCTACACCGAGGTC
seqC    GACATGGAGGCCCTGAGAAGTACCCTTCAGACTATGGAGTCTGACATCTACACCGAGGTC
        ********************************************************* seqA    CGCGAGCTGGTGAGCCTCAAGCAGGAGCAGCAGGCTTTCAAGGAGGCGGCCGACACGGAG
seqB    CGCGAGCTGGTGAGCCTCAAGCAGGAGCAGCAGGCTTTCAAGGAGGCGGCCGACACGGAG
seqC    CGCGAGCTGGTGAGCCTCAAGCAGGAGCAGCAGGCTTTCAAGGAGGCGGCCGACACGGAG
        ************************************************************ seqA    CGGCTCGCCCTGCAGGCCCTCACGGAGAAGCTTCTCAGGTCTGAGGAGTCCGTCTCCCGC
seqB    CGGCTCGCCCTGCAGGCCCTCACGGAGAAGCTTCTCAGGTCTGAGGAGTCCGTCTCCCGC
seqC    CGGCTCGCCCTGCAGGCCCTCACGGAGAAGCTTCTCAGGTCTGAGGAGCCCGTCTCCCGC
        *************************************** ******** seqA    CTCCCGGAGGAGATCCGGAGACTGGAGGAAGAGCTCCGCCAGCTGAAGTCCGATTCCCAC
seqB    CTCCCGGAGGAGATCCGGAGACTGGAGGAAGAGCTCCGCCAGCTGAAGTCCGATTCCCAC
seqC    CTCCCGGAGGAGATCCGGAGACTGGAGGAAGAGCTCCGCCAGCTGAAGTCCGATTCCCAC
        ************************************************************ seqA    GGGCCGAAGGAGGACGGAGGCTTCAGACACTCGGAAGCCTTTGAGGCACTCCAGCAAAAG
seqB    GGGCCGAAGGAGGACGGAGGCTTCAGACACTCGGAAGCCTTTGAGGCACTCCAGCAAAAG
seqC    GGGCCGAAGGAGGACGGAGGCTTCAGACACTCGGAAGCCTTTGAGGCACTCCAGCAAAAG
        ************************************************************ seqA    AGTCAGGGACTGGACTCCAGGCTCCAGCACGTGGAGGATGGGGTGCTCTCCATGCAGGTG
seqB    AGTCAGGGACTGGACTCCAGGCTCCAGCACGTGGAGGATGGGGTGCTCTCCATGCAGGTG
seqC    AGTCAGGGACTGGACTCCAGGCTCCAGCACGTGGAGGATGGGGTGCTCTCCATGCAGGTG
        ************************************************************ seqA    GCTTCTGCGCGCCAGACCGAGAGCCTGGAGTCCCTCCTGTCCAAGAGCCAGGAGCACGAG
seqB    GCTTCTGCGCGCCAGACCGAGAGCCTGGAGTCCCTCCTGTCCAAGAGCCAGGAGCACGAG
seqC    GCTTCTGCGCGCCAGACCGAGAGCCTGGAGTCCCTCCTGTCCAAGAGCCAGGAGCACGAG
        ***********************************************************
```

Figure 16(D)

```
seqA    CAGCGCCTGGCCGCCCTGCAGGGGCGCCTGGAAGGCCTCGGGTCCTCAGAGGCAGACCAG
seqB    CAGCGCCTGGCCGCCCTGCAGGGGCGCCTGGAAGGCCTCGGGTCCTCAGAGGCAGACCAG
seqC    CAGCGCCTGGCCGCCCTGCAGGGGCGCCTGGAAGGCCTCGGGTCCTCAGAGGCAGACCAG
        ************************************************************ seqA    GATGGCCTGGCCAGCACGGTGAGGAGCCTGGGCGAGACCCAGCTGGTGCTCTACGGTGAC
seqB    GATGGCCTGGCCAGCACGGTGAGGAGCCTGGGCGAGACCCAGCTGGTGCTCTACGGTGAC
seqC    GATGGCCTGGCCAGCACGGTGAGGAGCCTGGGCGAGACCCAGCTGGTGCTCTACGGTGAC
        ************************************************************ seqA    GTGGAGGAGCTGAAGAGGAGTGTGGGCGAGCTCCCCAGCACCGTGGAATCACTCCAGAAG
seqB    GTGGAGGAGCTGAAGAGGAGTGTGGGCGAGCTCCCCAGCACCGTGGAATCACTCCAGAAG
seqC    GTGGAGGAGCTGAAGAGGAGTGTGGGCGAGCTCCCCAGCACCGTGGAATCACTCCAGAAG
        ************************************************************ seqA    GTGCAGGAGCAGGTGCACACGCTGCTCAGTCAGGACCAAGCCCAGGCCGCCCGTCTGCCT
seqB    GTGCAGGAGCAGGTGCACACGCTGCTCAGTCAGGACCAAGCCCAGGCCGCCCGTCTGCCT
seqC    GTGCAGGAGCAGGTGCACACGCTGCTCAGTCAGGACCAAGCCCAGGCCGCCCGTCTGCCT
        ************************************************************ seqA    CCTCAGGACTTCCTGGACAGACTTTCTTCTCTAGACAACCTGAAAGCCTCAGTCAGCCAA
seqB    CCTCAGGACTTCCTGGACAGACTTTCTTCTCTAGACAACCTGAAAGCCTCAGTCAGCCAA
seqC    CCTCAGGACTTCCTGGACAGACTTTCTTCTCTAGACAACCTGAAAGCCTCAGTCAGCCAA
        ************************************************************ seqA    GTGGAGGCGGACTTGAAAATGCTCAGGACTGCTGTGGACAGTTTGGTTGCATACTCGGTC
seqB    GTGGAGGCGGACTTGAAAATGCTCAGGACTGCTGTGGACAGTTTGGTTGCATACTCGGTC
seqC    GTGGAGGCGGACTTGAAAATGCTCAGGACTGCTGTGGACAGTTTGGTTGCATACTCGGTC
        ************************************************************ seqA    AAAATAGAAACCAACGAGAACAATCTGGAATCAGCCAAGGGTTTACTAGATGACCTGAGG
seqB    AAAATAGAAACCAACGAGAACAATCTGGAATCAGCCAAGGGTTTACTAGATGACCTGAGG
seqC    AAAATAGAAACCAACGAGAACAATCTGGAATCAGCCAAGGGTTTACTAGATGACCTGAGG
        ************************************************************ seqA    AATGATCTGGATAGGTTGTTTGTGAAAGTGGAGAAGATTCACGAAAAGGTCTAAATGAAT
seqB    AATGATCTGGATAGGTTGTTTGTGAAAGTGGAGAAGATTCACGAAAAGGTCTAAATGAAT
seqC    AATGATCTGGATAGGTTGTTTGTGAAAGTGGAGAAGATTCACGAAAAGGTCTAAATGAAT
        ************************************************************ seqA    TGCGTGTGCAGGGCGCGGATTTAAAGTCCAATTTCTCATGACCAAAAAATGTGTGGTTTT
seqB    TGCGTGTGCAGGGCGCGGATTTAAAGTCCAATTTCTCATGACCAAAAAATGTGTGGTTTT
seqC    TGCGTGTGCAGGGCGCGGATTTAAAGTCCAATTTCTCATGACCAAAAAATGTGTGGTTTT
        ************************************************************ seqA    TTCCCATGTGTCCCCTACCCCCCAATTTCTTGTCCCCTCTTAAAGAGCAGTTGTCACCAC
seqB    TTCCCATGTGTCCCCTACCCCCCAATTTCTTGTCCCCTCTTAAAGAGCAGTTGTCACCAC
seqC    TTCCCATGTGTCCCCTACCCCCCAATTTCTTGTCCCCTCTTAAAGAGCAGTTGTCACCAC
        ************************************************************ seqA    CTGAACACCAAGGCATTGTATTTTCATGCCCAGTTAACTTATTTACAATATTTAAGTTCT
seqB    CTGAACACCAAGGCATTGTATTTTCATGCCCAGTTAACTTATTTACAATATTTAAGTTCT
seqC    CTGAACACCAAGGCATTGTATTTTCATGCCCAGTTAACTTATTTACAATATTTAAGTTCT
        ************************************************************ seqA    CTGCTTCTGCATTTGGTTGGTTTCCTGAAGCGCAGCCCCTGTGAATAACAGGTGGCTTTT
seqB    CTGCTTCTGCATTTGGTTGGTTTCCTGAAGCGCAGCCCCTGTGAATAACAGGTGGCTTTT
seqC    CTGCTTCTGCATTTGGTTGGTTTCCTGAAGCGCAGCCCCTGTGAATAACAGGTGGCTTTT
        ************************************************************ seqA    CATGGATGTCTCTAGTCAGAGAAAAATGATAAAGGCTTAAATTGAGGATTAACAGAAGCA
seqB    CATGGATGTCTCTAGTCAGAGAAAAATGATAAAGGCTTAAATTGAGGATTAACAGAAGCA
seqC    CATGGATGTCTCTAGTCAGAGAAAAATGATAAAGGCTTAAATTGAGGATTAACAGAAGCA
        ************************************************************ seqA    GATTAACCTCAGAAATCCTGTCTGGCTGGCAGATTTCAAGTAAAAAAAAAAAAAGGTGG
seqB    GATTAACCTCAGAAATCCTGTCTGGCTGGCAGATTTCAAGTAAAAAAAAAAAAAA-----
seqC    GATTAACCTCAGAAATCCTGTCTGGCTGGCAGATTTCAAGTAAAAAAAAAAAAAA-----
        ******************************************************
```

Figure 16(E)

```
seqA    GTTGGGGGGACCCTTTTCTTTCTAGTTGTCTTTAAGGAAAATTAATTTTACTTTTTTTTT
seqB    ---------------------------------------AAAA-----------------
seqC    ---------------------------------------AAAA-----------------
                                               **** seqA    TGTTCTGGCCGAAATTTTTATGAGATATCTCTCACTTGTCTTCCACTTTGAACCGGTTAA
seqB    ------------------------------------------------------------
seqC    ------------------------------------------------------------ seqA    AGCTCATAGCTGTCAGCTCTGAATGAGGAGGGGAGAAGCCCCTGGGTCTTTCTTTGAAAG
seqB    ------------------------------------------------------------
seqC    ------------------------------------------------------------ seqA    GAATCCGCTGCTTGAGGGCTGCCTCCCTCATGGTGTGCGTGTCGTTCTCTTCCTGACGCA
seqB    ------------------------------------------------------------
seqC    ------------------------------------------------------------ seqA    TCTGTGATATCAGAGGTAACTATGCAAAGCATCCAGGCGGTTCTGAATGTGAAGCACTAC
seqB    ------------------------------------------------------------
seqC    ------------------------------------------------------------ seqA    ACCCAGCAGAGTCCCGGTGCCCTCTGTCCCCACTGCCGGCCCATGTCCTCTCTCCGGAGG
seqB    ------------------------------------------------------------
seqC    ------------------------------------------------------------ seqA    TCACCAAGGAATGCACAGGTTTCGACTACCAGAAAGGGGAGTCCTTGGGTTCTTTCAAAA
seqB    ------------------------------------------------------------
seqC    ------------------------------------------------------------ seqA    AATTCGTGAGGAGAGCTGTCTACAGTGGAATAGGGGGTCTCCCTGGGGAATGCAGGCCAA
seqB    ------------------------------------------------------------
seqC    ------------------------------------------------------------ seqA    GTCCTTTTATTTTAACATGATGTCCATGAAGAGGTTTGCCGTCTGGGCAGCCCTGTCGGC
seqB    ------------------------------------------------------------
seqC    ------------------------------------------------------------ seqA    AAGGAGCGTGCATACTGCGTTTGTGTAATTGTTTGCTGTATCTCCCTTCCCTCTGAGCTG
seqB    ------------------------------------------------------------
seqC    ------------------------------------------------------------ seqA    TATTGTTCTTTAATGGCTGTCTTGCCCTTCCAAAAAAAATTGAAAAAAAAAAAA  (SEQ ID NO: 20)
seqB    -----------------------------------------------------  (SEQ ID NO: 21)
seqC    -----------------------------------------------------  (SEQ ID NO: 22)
```

Figure 17

17(A).
Homo sapiens chromosome 12, reference assembly, complete sequence
gi|89161190|ref|NC_000012.10|NC_000012

(Source) www.ncbi.nlm.nih.gov

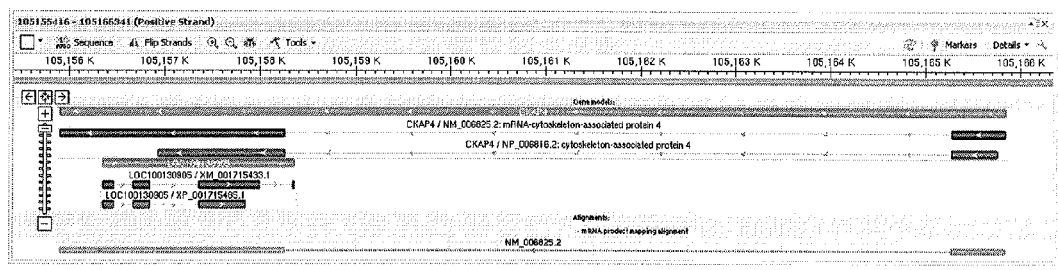

17B. (Source) genome.ewha.ac.kr/ECgene/

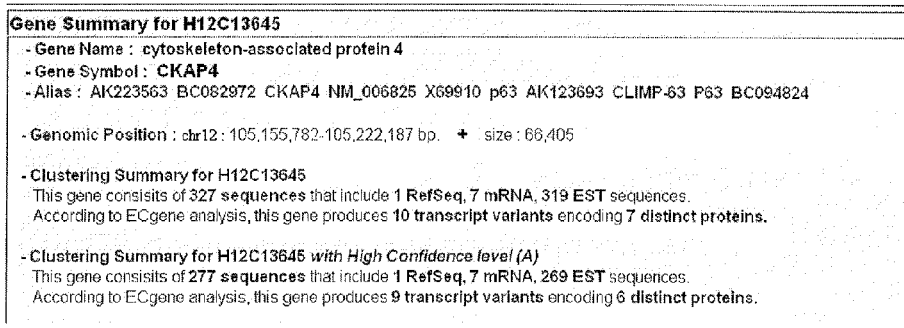

| Transcript ID | Transcript Type | Confidence level | Min. Clones | # mRNAs | # ESTs | # Spliced ESTs | # Exons | # polyA seq. | mRNA | CDS | 5'UTR | 3'UTR |
|---|---|---|---|---|---|---|---|---|---|---|---|---|
| H12C13645.1 R | Coding | A | 1 | 3 | 179 | 1 | 2 | 0 | 3,095 bp | 796 bp (265aa) | 2,298 bp | 1 bp |
| H12C13645.2 | NMD | A | 1 | 1 | 190 | 17 | 4 | 0 | 2,683 bp | 582 bp (193aa) | 1,930 bp | 171 bp |
| H12C13645.3 # | Coding | A | 1 | 2 | 218 | 45 | 3 | 0 | 2,615 bp | 684 bp (228aa) | 1,930 bp | 1 bp |
| H12C13645.4 | NMD | A | 1 | 1 | 192 | 19 | 3 | 0 | 2,726 bp | 582 bp (194aa) | 1,930 bp | 214 bp |
| H12C13645.5 | Coding | A | 1 | 0 | 70 | 1 | 2 | 0 | 1,578 bp | 428 bp (142aa) | 1,149 bp | 1 bp |
| H12C13645.6 | Coding | A | 1 | 0 | 80 | 2 | 2 | 0 | 1,792 bp | 428 bp (142aa) | 1,363 bp | 1 bp |
| H12C13645.7 | NMD | A | 1 | 0 | 31 | 4 | 4 | 0 | 1,196 bp | 582 bp (194aa) | 457 bp | 157 bp |
| H12C13645.8 | NMD | A | 1 | 0 | 27 | 1 | 3 | 0 | 1,269 bp | 462 bp (154aa) | 457 bp | 350 bp |
| H12C13645.9 | NMD | A | 1 | 0 | 10 | 1 | 4 | 0 | 1,120 bp | 582 bp (194aa) | 138 bp | 400 bp |

Figure 18
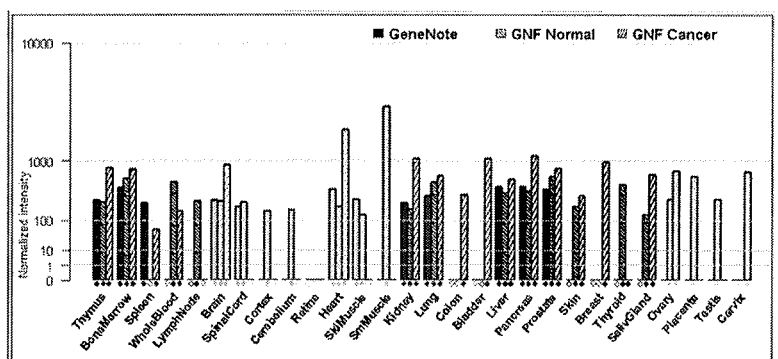
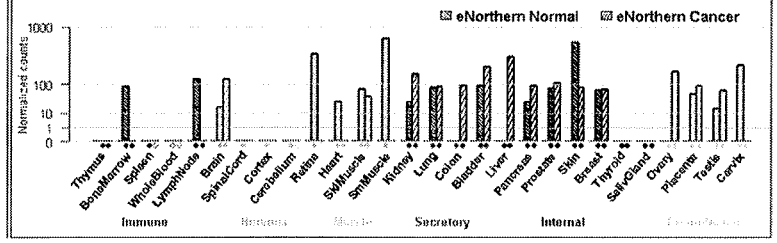
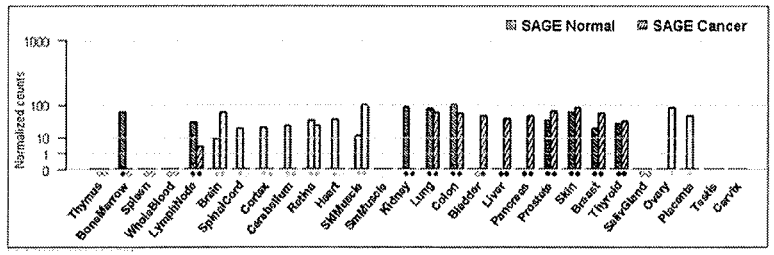

Figure 19

Orthologs for CKAP4 gene from 10 species (see top 5)

| Organism | Gene | Locus | Description | Human Similarity | NCBI accessions |
|---|---|---|---|---|---|
| dog (Canis familiaris) | CKAP4[1] | -- | cytoskeleton-associated protein 4 | 87.04(n) 84.34(a) | 481295 XM_538416.2 XP_538416.2 |
| chimpanzee (Pan troglodytes) | CKAP4[1] | -- | cytoskeleton-associated protein 4 | 98.05(n) 97.26(a) | 742720 XM_001161127.1 XP_001161127.1 |
| cow (Bos taurus) | CKAP4[1] | -- | cytoskeleton-associated protein 4 | 84.92(n) 84.69(a) | 515784 XM_868540.2 XP_873633.2 |
| rat (Rattus norvegicus) | Ckap4[1] | -- | cytoskeleton-associated protein 4 | 84.79(n) 83.97(a) | 362859 XM_343189.3 XP_343190.1 |
| mouse (Mus musculus) | Ckap4[2] Ckap4[1] | 10[4] | cytoskeleton-associated protein 4[1,4] | 85.19(n)[1] 83.97(a)[1] | 216197[1] NM_175451.1[1] NP_780660.1[1] AC140333[4] AI152085[4] (see all 24) |
| chicken (Gallus gallus) | CKAP4[1] | -- | cytoskeleton-associated protein 4 | 61.5(n) 55.47(a) | 418073 XM_416309.2 XP_416309.2 |
| zebrafish (Danio rerio) | zgc:85975[1] | -- | zgc:85975 | 46.62(n) 25.89(a) | 406549 NM_213265.1 NP_998430.1 |
| African clawed frog (Xenopus laevis) | BG554644.1[1-] | -- | -- | 81.25(n) | BG554644.1 |
| tropical clawed frog (Silurana tropicalis) | BX707940.1[1-] | -- | -- | 72.06(n) | BX707940.1 |
| wheat (Triticum aestivum) | BQ484045.1[1-] | -- | -- | 70.93(n) | BQ484045.1 |

About this table   Species with no ortholog

SEQUENCE LISTING

```
<160> NUMBER OF SEQ ID NOS: 22

<210> SEQ ID NO 1
<211> LENGTH: 31
<212> TYPE: DNA
<213> ORGANISM: Artificial
<220> FEATURE:
<223> OTHER INFORMATION: Primer

<400> SEQUENCE: 1
caccggtacc atgccctcgg ccaaacaaag g                              31

<210> SEQ ID NO 2
<211> LENGTH: 40
<212> TYPE: DNA
<213> ORGANISM: Artificial
<220> FEATURE:
<223> OTHER INFORMATION: Primer

<400> SEQUENCE: 2
aattctcgag gaccttttcg tgaatcttct ccactttcac                     40

<210> SEQ ID NO 3
<211> LENGTH: 30
<212> TYPE: DNA
<213> ORGANISM: Artificial
<220> FEATURE:
<223> OTHER INFORMATION: Primer

<400> SEQUENCE: 3
tattctcgag atggtgagca agggcgagga                                30

<210> SEQ ID NO 4
<211> LENGTH: 30
<212> TYPE: DNA
<213> ORGANISM: Artificial
<220> FEATURE:
<223> OTHER INFORMATION: Primer

<400> SEQUENCE: 4
ctcggaattc ttacttgtac agctcgtcca                                30

<210> SEQ ID NO 5
<211> LENGTH: 2913
<212> TYPE: DNA
<213> ORGANISM: Homo sapiens
```

<400> SEQUENCE: 5

```
gggggagccc ctgcaagttt cccgggccgc gcgccgcgct cgctcgcctc ccagcccgcg      60
gcccgagccg ccgccgcgcc cgccatgccc tcggccaaac aaagggggctc caagggcggc    120
cacgcgccg cgagcccctc ggagaagggt gcccacccgt cgggcggcgc ggatgacgtg     180
gcgaagaagc cgccgccggc gccgcagcag ccgccgccgc cgcccgcgcc gcacccgcag    240
cagcacccgc agcagcaccc gcagaaccag gcgcacggca agggcggcca ccgcggcggc    300
ggcggcggcg gcggcaagtc ctcctcctcc tcctccgcct ccgccgccgc tgccgccgcc    360
gccgcctcgt cctcggcgtc ctgctcgcgc aggctcggca gggcgctcaa ctttctcttc    420
tacctcgccc tggtggcggc ggccgctttc tcgggctggt gcgtccacca cgtcctggag    480
gaggtccagc aggtccggcg cagccaccag gacttctccc ggcagaggga ggagctgggc    540
cagggcttgc agggcgtcga gcagaaggtg cagtctttgc aagccacatt tggaactttt    600
gagtccatct tgagaagctc ccaacataaa caagacctca cagagaaagc tgtgaagcaa    660
ggggagagtg aggtcagccg gatcagcgaa gtgctgcaga aactccagaa tgagattctc    720
aaagacctct cggatgggat ccatgtggtg aaggacgccc gggagcggga cttcacgtcc    780
ctggagaaca cggtggagga gcggctgacg gagctcacca aatccatcaa cgacaacatc    840
gccatcttca cagaagtcca gaagaggagc cagaaggaga tcaatgacat gaaggcaaag    900
gttgcctccc tggaagaatc tgaggggaac aagcaggatt gaaagccttt aaaggaagct    960
gtgaaggaga tacagacctc agccaagtcc agagagtggg acatggaggc cctgagaagt   1020
accctttcaga ctatggagtc tgacatctac accgaggttc gcgagctggt gagcctcaag   1080
caggagcagc aggctttcaa ggaggcggcc gacacggagc ggctcgccct gcaggccctc   1140
acggagaagc ttctcaggtc tgaggagtcc gtctcccgcc tcccggagga gatccggaga   1200
ctggaggaag agctccgcca gctgaagtcc gattcccacg ggccgaagga ggacggaggc   1260
ttcagacact cggaagcctt tgaggcactc cagcaaaaga gtcagggact ggactccagg   1320
ctccagcacg tggaggatgg ggtgctctcc atgcaggtgg cttctgcgcg ccagaccgag   1380
agcctggagt ccctcctgtc caagagccag gagcacgagc agcgcctggc cgccctgcag   1440
gggcgcctgg aaggcctcgg gtcctcagag gcagaccagg atggcctggc cagcacggtg   1500
aggagcctgg gcgagaccca gctggtgctc tacggtgacg tggaggagct gaagaggagt   1560
gtgggcgagc tccccagcac cgtggaatca ctccagaagg tgcaggagca ggtgcacacg   1620
ctgctcagtc aggaccaagc ccaggccgcc cgtctgcctc ctcaggactt cctgacagaa   1680
ctttcttctc tagacaacct gaaagcctca gtcagccaag tggaggcgga cttgaaaatg   1740
ctcaggactg ctgtgacag tttgttgca tactcggtca aaatagaaac caacgagaac     1800
aatctggaat cagccaaggg tttactagat gacctgagga atgatctgga taggttgttt   1860
gtgaaagtgg agaagattca cgaaaaggtc taaatgaatt gcgtgtgcag ggcgcggatt   1920
taaagtccaa tttctcatga ccaaaaaatg tgtggttttt tcccatgtgt cccctacccc   1980
ccaatttctt gtcccctctt aaagagcagt tgtcaccacc tgaacaccaa ggcattgtat   2040
tttcatgccc agttaactta tttacaatat ttaagttctc tgcttctgca tttgttggt    2100
ttcctgaagc gcagcccctg tgaataacag gtggcttttc atggatgtct ctagtcagag   2160
aaaaatgata aaggcttaaa ttgaggatta acagaagcag attaacctca gaaatcctgt   2220
ctggctggca gatttcaagt aaaaaaaaaa aaaggtgggg ttgggggggac ccttttctttt  2280
ctagttgtct ttaaggaaaa ttaattttac tttttttttt gttctggccg aaattttttat  2340
```

-continued

```
gagatatctc tcacttgtct tccactttga accggttaaa gctcatagct gtcagctctg    2400
aatgaggagg ggagaagccc ctgggtcttt ctttgaaagg aatccgctgc ttgagggctg    2460
cctccctcat ggtgtgcgtg tcgttctctt cctgacgcat ctgtgatatc agaggtaact    2520
atgcaaagca tccaggcggt tctgaatgtg aagcactaca cccagcagag tcccggtgcc    2580
ctctgtcccc actgccggcc catgtcctct ctccggaggt caccaaggaa tgcacaggtt    2640
tcgactacca gaaaggggag tccttgggtt ctttcaaaaa attcgtgagg agagctgtct    2700
acagtggaat aggggggtctc cctggggaat gcaggccaag tccttttatt ttaacatgat    2760
gtccatgaag aggtttgccg tctgggcagc cctgtcggca aggagcgtgc atactgcgtt    2820
tgtgtaattg tttgctgtat ctcccttccc tctgagctgt attgttcttt aatggctgtc    2880
ttgcccttcc aaaaaaaatt gaaaaaaaaa aaa                                 2913
```

<210> SEQ ID NO 6
<211> LENGTH: 602
<212> TYPE: PRT
<213> ORGANISM: Homo sapiens

<400> SEQUENCE: 6

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
            20                  25                  30

Ala Lys Lys Pro Pro Pro Ala Pro Gln Gln Pro Pro Pro Pro Pro Ala
        35                  40                  45

Pro His Pro Gln Gln His Pro Gln Gln His Pro Gln Asn Gln Ala His
    50                  55                  60

Gly Lys Gly Gly His Arg Gly Gly Gly Gly Gly Gly Lys Ser Ser
65                  70                  75                  80

Ser Ser Ser Ser Ala Ser Ala Ala Ala Ala Ala Ala Ser Ser
                85                  90                  95

Ser Ala Ser Cys Ser Arg Arg Leu Gly Arg Ala Leu Asn Phe Leu Phe
            100                 105                 110

Tyr Leu Ala Leu Val Ala Ala Ala Phe Ser Gly Trp Cys Val His
        115                 120                 125

His Val Leu Glu Glu Val Gln Gln Val Arg Arg Ser His Gln Asp Phe
    130                 135                 140

Ser Arg Gln Arg Glu Glu Leu Gly Gln Gly Leu Gln Gly Val Glu Gln
145                 150                 155                 160

Lys Val Gln Ser Leu Gln Ala Thr Phe Gly Thr Phe Glu Ser Ile Leu
                165                 170                 175

Arg Ser Ser Gln His Lys Gln Asp Leu Thr Glu Lys Ala Val Lys Gln
            180                 185                 190

Gly Glu Ser Glu Val Ser Arg Ile Ser Glu Val Leu Gln Lys Leu Gln
        195                 200                 205

Asn Glu Ile Leu Lys Asp Leu Ser Asp Gly Ile His Val Val Lys Asp
    210                 215                 220

Ala Arg Glu Arg Asp Phe Thr Ser Leu Glu Asn Thr Val Glu Glu Arg
225                 230                 235                 240

Leu Thr Glu Leu Thr Lys Ser Ile Asn Asp Asn Ile Ala Ile Phe Thr
                245                 250                 255

Glu Val Gln Lys Arg Ser Gln Lys Glu Ile Asn Asp Met Lys Ala Lys
            260                 265                 270

Val Ala Ser Leu Glu Glu Ser Glu Gly Asn Lys Gln Asp Leu Lys Ala
         275                 280                 285

Leu Lys Glu Ala Val Lys Glu Ile Gln Thr Ser Ala Lys Ser Arg Glu
        290                 295                 300

Trp Asp Met Glu Ala Leu Arg Ser Thr Leu Gln Thr Met Glu Ser Asp
305                 310                 315                 320

Ile Tyr Thr Glu Val Arg Glu Leu Val Ser Leu Lys Gln Glu Gln Gln
                325                 330                 335

Ala Phe Lys Glu Ala Ala Asp Thr Glu Arg Leu Ala Leu Gln Ala Leu
            340                 345                 350

Thr Glu Lys Leu Leu Arg Ser Glu Ser Val Ser Arg Leu Pro Glu
        355                 360                 365

Glu Ile Arg Arg Leu Glu Glu Glu Leu Arg Gln Leu Lys Ser Asp Ser
    370                 375                 380

His Gly Pro Lys Glu Asp Gly Gly Phe Arg His Ser Glu Ala Phe Glu
385                 390                 395                 400

Ala Leu Gln Gln Lys Ser Gln Gly Leu Asp Ser Arg Leu Gln His Val
                405                 410                 415

Glu Asp Gly Val Leu Ser Met Gln Val Ala Ser Ala Arg Gln Thr Glu
            420                 425                 430

Ser Leu Glu Ser Leu Leu Ser Lys Ser Gln Glu His Glu Gln Arg Leu
        435                 440                 445

Ala Ala Leu Gln Gly Arg Leu Glu Gly Leu Gly Ser Ser Glu Ala Asp
    450                 455                 460

Gln Asp Gly Leu Ala Ser Thr Val Arg Ser Leu Gly Glu Thr Gln Leu
465                 470                 475                 480

Val Leu Tyr Gly Asp Val Glu Glu Leu Lys Arg Ser Val Gly Glu Leu
                485                 490                 495

Pro Ser Thr Val Glu Ser Leu Gln Lys Val Gln Glu Gln Val His Thr
            500                 505                 510

Leu Leu Ser Gln Asp Gln Ala Gln Ala Ala Arg Leu Pro Pro Gln Asp
        515                 520                 525

Phe Leu Asp Arg Leu Ser Ser Leu Asp Asn Leu Lys Ala Ser Val Ser
    530                 535                 540

Gln Val Glu Ala Asp Leu Lys Met Leu Arg Thr Ala Val Asp Ser Leu
545                 550                 555                 560

Val Ala Tyr Ser Val Lys Ile Glu Thr Asn Glu Asn Asn Leu Glu Ser
                565                 570                 575

Ala Lys Gly Leu Leu Asp Asp Leu Arg Asn Asp Leu Asp Arg Leu Phe
            580                 585                 590

Val Lys Val Glu Lys Ile His Glu Lys Val
        595                 600

<210> SEQ ID NO 7
<211> LENGTH: 4012
<212> TYPE: DNA
<213> ORGANISM: Homo sapiens

<400> SEQUENCE: 7
gtgggagccc gcgaggtggc ccgagcgagg gccccgcatc ccgcagagc ccgcccgagg      60 gcgcagcctg ccacgccagg ggaggcggcc gggcggcggg gaacggcggg ggcggagcgc     120
agcctcccga cgccgccgcc tcaccgcccc cctccgcctc ctcggcctcc gctcgcagcc    180
gccgcctccg cctccgccgg gctgaggagc cgggagtccg ccgcgccggc tcggggctgc    240

```
gggatgggga gttagcgcca cggcggcggc agtggccgca gcgcaccccg ccgccgccca    300
ggagcccgtc cagccagggg tgccgggccc gcccagcccg ccccggagcc aggcccgcgg    360
gcggcggcgg agctgggcag gtggatgcgg ctggaagatg gcgccctcgg gcccgggcag    420
cagcgccagg cggcggtgcc ggcgggtgct gtactggatc ccggtggtgt tcatcaccct    480
cctgctcggc tggtcctact acgcctacgc catccagctg tgcatagtgt ccatggaaaa    540
cactggcgaa caagttgtgt gcctgatggc ctatcatcta cttttgcaa tgtttgtctg     600 gtcatactgg aaaactatct ttacattacc aatgaatcct tcaaaagaat tccatctctc    660
ttatgcagag aaagatttgt tggagagaga gccaagagga gaagcccatc aggaagttct    720
taggcgagca gccaaggatc ttcccatcta taccaggacc atgtctggag ccatccgata    780
ctgtgacaga tgccaactta aaaaccaga tcgctgccat cactgctccg tctgtgataa      840
atgtattttg aagatggatc atcattgtcc atgggtgaac aattgtgttg gattttcaaa    900
ttataagttc tttctccttt tcttggctta ttctctgctc tactgccttt ttattgcggc    960
aacagattta cagtatttta tcaaattttg gacaaatggc ctacctgata ctcaagccaa   1020
gttccatatt atgtttttat tctttgctgc agctatgttt tctgtcagct tgtcttctct   1080
gtttggctat cattgttggc tagtcagcaa aaataaatct acattagagg cattcagaag   1140
tccagtattt cgacatggaa cagataagaa tggattcagc ttgggtttca gtaaaaacat   1200
gcgacaagtt tttggtgatg agaagaagta ctggttgcta cccatttttt caagtctagg   1260
tgatggctgc tcctttccaa cttgccttgt taaccaggat cctgaacaag catctactcc   1320
tgcagggctg aattccacag ctaaaaatct cgaaaaccat cagtttcctg caaagccatt   1380
gagagagtcc cagagccacc ttcttactga ttctcagtct tggacggaga gcagcataaa   1440
cccaggaaaa tgcaaagctg gtatgagcaa tcctgcatta accatggaaa atgagactta   1500
actcttcaag caagataaat tcatactttta taaaagtatc aatgctgtag atggatggaa   1560
gaggcttccc acaggaaggt gccaccagtc agttgtgcct atgtccctttggctggaaat    1620 gcagaatatg aattgattag ttctctccaa gccattgctt aaaatataac atgttttgga   1680
tccaatacac acattgttac aactaacaca aattcctatt aaatattaaa agtagttctg   1740
gtttattaat caacggggaa aacatcttct ccaaaaaact tggaataaat ccaaggacca   1800
gtttttaccc aaatatatgg gtagcacagt ttatcacata gaaactccat taatcatctg   1860
attttccgaa tctgaaaatt gagactatta agatattagg atttcagaga tttcaagtca   1920
cattataatg ataagcatta ttcataaaac ttgttacctt taagaaggtg gaagtggcaa   1980
accatacttc ttttttttcc tctgatgtga atccagcctc agactgagtg aactgtaata   2040
attatgaatt cattacagag tccaggtggc ctgcagttga agatcatcaa ccattttgc    2100 ctcacttaat tccagccttt tgttttctgc tggaaaataa gtgtggacat tgaagcttga   2160
gctctcaaag cagttggctg gaatactttt gtcagaatac ggtacatttc tattacatca   2220
gaaatatatt ttcatctctt cttgttaaat tgggaggaaa tttatgatag caattatgaa   2280
gattgtttta tgacattctt ttgtcagttt ggctttctaa aaatctcttt ttagattatt   2340
tctcctgttg aacatagtaa aactattgaa tttctcttaa gaattcctaa taggtcaata   2400 gatttacccct ccagtgatat ctatattatt tcttttctcgt ctcatcaaaa tgatgacagg   2460
taaactatat ttttccttaa acacctatta cagttaaatt atgcaaatca ttaaataaaa   2520
atcatacaac ttttggaaag ttagttcaac atgaactaaa atggcatgct atttggaaat   2580
```

```
ttagtttgag ataaactaaa gtgtgttgat gccagaatgt tcagcttcag taaatataat    2640
aagctcttgt gccttgtatg cactatttaa aaaaagtttt ttttatttga gtccagtata    2700
attcatgtaa atgttaacaa ttagaataat actctgtatg cttttttgat actgattttg    2760
agaatttaaa gcagattacc ttttaaaact ggaccaacta agtaattggt atttaatcaa    2820
agagaaaatg gtaataaact tttcaaaatc tttgttaaac caaacattca acacaaaata    2880
aactagaagg ccagaggata atggaataaa agatcattgc aattacttat ccttcctaaa    2940
aatatagttt tatattaatt gtgcttatgg aagaaacaat gtcagccaag tccatttat    3000 agtttgagtg caattctttg aacaatgaaa atatctgcag tctttcacag atttgtatta    3060
tgctgaagag tttcatctga caatctgctt caagaaatct cagaaaatat gataacattt    3120
taactttcat tttagagcac gttttggtca tttttaaaaa tacctaaagt gccagaccgg    3180
aacctatagc tactgctaga agtcttaaaa aaaccaacag cagcacagga tgtattaaga    3240
attatatgaa gtcaggtttg tttttttttt tttttttttt tcaaagcaca gtactgttag    3300 ctgttttgt ggacaggatt cgattaagta ttccctcttg tcaaactgga agctagggga    3360
aaaagaggga tttttatcct ttactcttct agagtactgt taatgcccct ttcccacagt    3420 ctttatata attaaatata tgtcaataca cattagaatc agatttgaaa agttaaaac    3480 aatttcattg ttgtaattgt tccctttctg ttttcatata gtgaataacc tttaagggt    3540 tgttttgttt tgttttgaat ataggagtt ataatctttg gagatgattg catatctcat    3600
tagatatgca atataaattt atctgagtga acaaagtgct aaataaatag atctacattt    3660
tgtacatatt tatataaat ttacctttaa gtatttactt taaaaaattt aatggcttaa    3720
ctcgaacttg aagacacata cttcaactgt ccttattgtc cattaaactg ataattttga    3780
tttttcttgc ttttatagat tttactatat aggaatcaag atttaagaaa ttttgcatta    3840
aaaatagtgt accaatgctt catatacgtt agttatttgc tattatgtag ggaagaggat    3900
tgttatttca aagatatatt aaagaacagt tgcatctgaa tataatcatg atgcattcaa    3960
tgaagttcat atccatgaat tcactcctaa tataccctaa taaagtggtt ga            4012
```

<210> SEQ ID NO 8
<211> LENGTH: 367
<212> TYPE: PRT
<213> ORGANISM: Homo sapiens

<400> SEQUENCE: 8

```
Met Ala Pro Ser Gly Pro Gly Ser Ser Ala Arg Arg Cys Arg Arg
1               5                   10                  15

Val Leu Tyr Trp Ile Pro Val Val Phe Ile Thr Leu Leu Gly Trp
                20                  25                  30

Ser Tyr Tyr Ala Tyr Ala Ile Gln Leu Cys Ile Val Ser Met Glu Asn
                35                  40                  45

Thr Gly Glu Gln Val Val Cys Leu Met Ala Tyr His Leu Leu Phe Ala
            50                  55                  60

Met Phe Val Trp Ser Tyr Trp Lys Thr Ile Phe Thr Leu Pro Met Asn
65                  70                  75                  80

Pro Ser Lys Glu Phe His Leu Ser Tyr Ala Glu Lys Asp Leu Leu Glu
                85                  90                  95

Arg Glu Pro Arg Gly Glu Ala His Gln Glu Val Leu Arg Arg Ala Ala
            100                 105                 110

Lys Asp Leu Pro Ile Tyr Thr Arg Thr Met Ser Gly Ala Ile Arg Tyr
        115                 120                 125
```

```
Cys Asp Arg Cys Gln Leu Ile Lys Pro Asp Arg Cys His His Cys Ser
            130                 135                 140

Val Cys Asp Lys Cys Ile Leu Lys Met Asp His His Cys Pro Trp Val
145                 150                 155                 160

Asn Asn Cys Val Gly Phe Ser Asn Tyr Lys Phe Phe Leu Leu Phe Leu
                165                 170                 175

Ala Tyr Ser Leu Leu Tyr Cys Leu Phe Ile Ala Ala Thr Asp Leu Gln
                180                 185                 190

Tyr Phe Ile Lys Phe Trp Thr Asn Gly Leu Pro Asp Thr Gln Ala Lys
                195                 200                 205

Phe His Ile Met Phe Leu Phe Phe Ala Ala Ala Met Phe Ser Val Ser
            210                 215                 220

Leu Ser Ser Leu Phe Gly Tyr His Cys Trp Leu Val Ser Lys Asn Lys
225                 230                 235                 240

Ser Thr Leu Glu Ala Phe Arg Ser Pro Val Phe Arg His Gly Thr Asp
                245                 250                 255

Lys Asn Gly Phe Ser Leu Gly Phe Ser Lys Asn Met Arg Gln Val Phe
                260                 265                 270

Gly Asp Glu Lys Lys Tyr Trp Leu Leu Pro Ile Phe Ser Ser Leu Gly
            275                 280                 285

Asp Gly Cys Ser Phe Pro Thr Cys Leu Val Asn Gln Asp Pro Glu Gln
290                 295                 300

Ala Ser Thr Pro Ala Gly Leu Asn Ser Thr Ala Lys Asn Leu Glu Asn
305                 310                 315                 320

His Gln Phe Pro Ala Lys Pro Leu Arg Glu Ser Gln Ser His Leu Leu
                325                 330                 335

Thr Asp Ser Gln Ser Trp Thr Glu Ser Ser Ile Asn Pro Gly Lys Cys
                340                 345                 350

Lys Ala Gly Met Ser Asn Pro Ala Leu Thr Met Glu Asn Glu Thr
                355                 360                 365

<210> SEQ ID NO 9
<211> LENGTH: 740
<212> TYPE: DNA
<213> ORGANISM: Artificial
<220> FEATURE:
<223> OTHER INFORMATION: Artifical Construct

<400> SEQUENCE: 9
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccaa gctgagcaaa gaccccaacg agaagcgcga tcacatggtc     660
ctgctggagt tcgtgaccgc cgccgggatc actctcggca tggacgagct gtacaagtaa     720
```
ttacttgtac agctcgtcca 740

<210> SEQ ID NO 10
<211> LENGTH: 239
<212> TYPE: PRT
<213> ORGANISM: Artificial
<220> FEATURE:
<223> OTHER INFORMATION: Artifical Construct

<400> SEQUENCE: 10

```
Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65              70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 11
<211> LENGTH: 591
<212> TYPE: PRT
<213> ORGANISM: Homo sapiens

<400> SEQUENCE: 11

```
Ala Arg Ser Pro Pro Ser Pro Arg Pro Glu Pro Pro Arg Pro Pro
1               5                   10                  15

Cys Pro Arg Pro Asn Lys Gly Ala Pro Arg Ala Ala Thr Ala Pro Arg
                20                  25                  30

Ala Pro Arg Arg Arg Val Pro Thr Arg Arg Ala Ala Met Thr Trp
            35                  40                  45

Arg Arg Ser Arg Arg Arg Arg Ser Arg Arg Arg Pro Arg
        50                  55                  60

Arg Thr Arg Ser Ser Thr Arg Ser Ser Thr Arg Arg Thr Arg Arg Thr
```

```
            65                  70                  75                  80
Ala Arg Ala Ala Thr Ala Ala Ala Ala Ala Leu Gly Arg Ala
                85                  90                  95
Leu Asn Phe Leu Phe Tyr Leu Ala Leu Val Ala Ala Phe Ser
                100                 105                 110
Gly Trp Cys Val His His Val Leu Glu Val Gln Val Arg Arg
                115                 120                 125
Ser His Gln Asp Phe Ser Arg Gln Arg Glu Glu Leu Gly Gln Gly Leu
        130                 135                 140
Gln Gly Val Glu Gln Lys Val Gln Ser Leu Gln Ala Thr Phe Gly Thr
145                 150                 155                 160
Phe Glu Ser Ile Leu Arg Ser Ser Gln His Lys Gln Asp Leu Thr Glu
                165                 170                 175
Lys Ala Val Lys Gln Gly Glu Ser Glu Val Ser Arg Ile Ser Glu Val
                180                 185                 190
Leu Gln Lys Leu Gln Asn Glu Ile Leu Lys Asp Leu Ser Asp Gly Ile
                195                 200                 205
His Val Val Lys Asp Ala Arg Glu Arg Asp Phe Thr Ser Leu Glu Asn
        210                 215                 220
Thr Val Glu Glu Arg Leu Thr Glu Leu Thr Lys Ser Ile Asn Asp Asn
225                 230                 235                 240
Ile Ala Ile Phe Thr Glu Val Gln Lys Arg Ser Gln Lys Glu Ile Asn
                245                 250                 255
Asp Met Lys Ala Lys Val Ala Ser Leu Glu Glu Ser Glu Gly Asn Lys
                260                 265                 270
Gln Asp Leu Lys Ala Leu Lys Glu Ala Val Lys Glu Ile Gln Thr Ser
        275                 280                 285
Ala Lys Ser Arg Glu Trp Asp Met Glu Ala Leu Arg Ser Thr Leu Gln
        290                 295                 300
Thr Met Glu Ser Asp Ile Tyr Thr Glu Val Arg Glu Leu Val Ser Leu
305                 310                 315                 320
Lys Gln Glu Gln Gln Ala Phe Lys Glu Ala Ala Asp Thr Glu Arg Leu
                325                 330                 335
Ala Leu Gln Ala Leu Thr Glu Lys Leu Leu Arg Ser Glu Glu Ser Val
                340                 345                 350
Ser Arg Leu Pro Glu Glu Ile Arg Arg Leu Glu Glu Leu Arg Gln
        355                 360                 365
Leu Lys Ser Asp Ser His Gly Pro Lys Glu Asp Gly Gly Phe Arg His
        370                 375                 380
Ser Glu Ala Phe Glu Ala Leu Gln Gln Lys Ser Gln Gly Leu Asp Ser
385                 390                 395                 400
Arg Leu Gln His Val Glu Asp Gly Val Leu Ser Met Gln Val Ala Ser
                405                 410                 415
Ala Arg Gln Thr Glu Ser Leu Glu Ser Leu Leu Ser Lys Ser Gln Glu
                420                 425                 430
His Glu Gln Arg Leu Ala Ala Leu Gln Gly Arg Leu Glu Gly Leu Gly
        435                 440                 445
Ser Ser Glu Ala Asp Gln Asp Gly Leu Ala Ser Thr Val Arg Ser Leu
        450                 455                 460
Gly Glu Thr Gln Leu Val Leu Tyr Gly Asp Val Glu Glu Leu Lys Arg
465                 470                 475                 480
Ser Val Gly Glu Leu Pro Ser Thr Val Glu Ser Leu Gln Lys Val Gln
                485                 490                 495
```

```
Glu Gln Val His Thr Leu Leu Ser Gln Asp Gln Ala Gln Ala Ala Arg
            500                 505                 510

Leu Pro Pro Gln Asp Phe Leu Asp Arg Leu Ser Ser Leu Asp Asn Leu
        515                 520                 525

Lys Ala Ser Val Ser Gln Val Glu Ala Asp Leu Lys Met Leu Arg Thr
530                 535                 540

Ala Val Asp Ser Leu Val Ala Tyr Ser Val Lys Ile Glu Thr Asn Glu
545                 550                 555                 560

Asn Asn Leu Glu Ser Ala Lys Gly Leu Leu Asp Asp Leu Arg Asn Asp
            565                 570                 575

Leu Asp Arg Leu Phe Val Lys Val Glu Lys Ile His Glu Lys Val
        580                 585                 590
```

```
<210> SEQ ID NO 12
<211> LENGTH: 526
<212> TYPE: PRT
<213> ORGANISM: Homo sapiens

<400> SEQUENCE: 12

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Gly
            20                  25                  30

Ala Gln Leu Ser Leu Leu Pro Arg Pro Ala Ala Ala Phe Ser Gly
        35                  40                  45

Trp Cys Val His His Val Leu Glu Glu Val Gln Val Arg Arg Ser
    50                  55                  60

His Gln Asp Phe Ser Arg Gln Arg Glu Glu Leu Gly Gln Gly Leu Gln
65                  70                  75                  80

Gly Val Glu Gln Lys Val Gln Ser Leu Gln Ala Thr Phe Gly Thr Phe
                85                  90                  95

Glu Ser Ile Leu Arg Ser Ser Gln His Lys Gln Asp Leu Thr Glu Lys
            100                 105                 110

Ala Val Lys Gln Gly Glu Ser Glu Val Ser Arg Ile Ser Glu Val Leu
        115                 120                 125

Gln Lys Leu Gln Asn Glu Ile Leu Lys Asp Leu Ser Asp Gly Ile His
130                 135                 140

Val Val Lys Asp Ala Arg Glu Arg Asp Phe Thr Ser Leu Glu Asn Thr
145                 150                 155                 160

Val Glu Glu Arg Leu Thr Glu Leu Thr Lys Ser Ile Asn Asp Asn Ile
                165                 170                 175

Ala Ile Phe Thr Glu Val Gln Lys Arg Ser Gln Lys Glu Ile Asn Asp
            180                 185                 190

Met Lys Ala Lys Val Ala Ser Leu Glu Glu Ser Glu Gly Asn Lys Gln
        195                 200                 205

Asp Leu Lys Ala Leu Lys Glu Ala Val Lys Glu Ile Gly Thr Ser Ala
210                 215                 220

Lys Ser Arg Glu Trp Asp Met Glu Ala Leu Arg Ser Thr Leu Gln Thr
225                 230                 235                 240

Met Glu Ser Asp Ile Tyr Thr Glu Val Arg Glu Leu Val Ser Leu Lys
                245                 250                 255

Gln Glu Gln Gln Ala Phe Lys Glu Ala Ala Asp Thr Glu Arg Leu Ala
            260                 265                 270

Leu Gln Ala Leu Thr Glu Lys Leu Leu Arg Ser Glu Glu Ser Val Ser
```

```
                275                 280                 285
Arg Leu Pro Glu Glu Ile Arg Arg Leu Glu Glu Leu Arg Gln Leu
    290                 295                 300
Lys Ser Asp Ser His Gly Pro Lys Glu Asp Gly Phe Arg His Ser
305                 310                 315                 320
Glu Ala Phe Glu Ala Leu Gln Gln Lys Ser Gln Gly Leu Asp Ser Arg
                325                 330                 335
Leu Gln His Val Glu Asp Gly Val Leu Ser Met Gln Val Ala Ser Ala
                340                 345                 350
Arg Gln Thr Glu Ser Leu Glu Ser Leu Leu Ser Lys Ser Gln Glu His
            355                 360                 365
Glu Gln Arg Leu Ala Ala Leu Gln Gly Arg Leu Glu Gly Leu Gly Ser
    370                 375                 380
Ser Glu Ala Asp Gln Asp Gly Leu Ala Ser Thr Val Arg Ser Leu Gly
385                 390                 395                 400
Glu Thr Gln Leu Val Leu Tyr Gly Asp Val Glu Glu Leu Lys Arg Ser
                405                 410                 415
Val Gly Glu Leu Pro Ser Thr Val Glu Ser Leu Gln Lys Val Gln Glu
                420                 425                 430
Gln Val His Thr Leu Leu Ser Gln Asp Gln Ala Gln Ala Ala Arg Leu
            435                 440                 445
Pro Pro Gln Asp Phe Leu Asp Arg Leu Ser Ser Leu Asp Asn Leu Lys
    450                 455                 460
Ala Ser Val Ser Gln Val Glu Ala Asp Leu Lys Met Leu Arg Thr Ala
465                 470                 475                 480
Val Asp Ser Leu Val Ala Tyr Ser Val Lys Ile Glu Thr Asn Glu Asn
                485                 490                 495
Asn Leu Glu Ser Ala Lys Gly Leu Leu Asp Asp Leu Arg Asn Asp Leu
                500                 505                 510
Asp Arg Leu Phe Val Lys Val Glu Lys Ile His Glu Lys Val
                515                 520                 525

<210> SEQ ID NO 13
<211> LENGTH: 602
<212> TYPE: PRT
<213> ORGANISM: Homo sapiens

<400> SEQUENCE: 13

Met Pro Ser Ala Lys Gln Arg Gly Ser Lys Gly Gly His Gly Ala Ala
1               5                   10                  15
Ser Pro Ser Glu Lys Gly Ala His Pro Ser Gly Gly Ala Asp Asp Val
                20                  25                  30
Ala Lys Lys Pro Pro Pro Ala Pro Gln Gln Pro Pro Pro Pro Pro Ala
            35                  40                  45
Pro His Pro Gln Gln His Pro Gln Gln His Pro Gln Asn Gln Ala His
        50                  55                  60
Gly Lys Gly Gly His Arg Gly Gly Gly Gly Gly Gly Lys Ser Ser
65                  70                  75                  80
Ser Ser Ser Ser Ala Ser Ala Ala Ala Ala Ala Ala Ser Ser
                85                  90                  95
Ser Ala Ser Cys Ser Arg Arg Leu Gly Arg Ala Leu Asn Phe Leu Phe
                100                 105                 110
Tyr Leu Ala Leu Val Ala Ala Ala Phe Ser Gly Trp Cys Val His
            115                 120                 125
```

```
His Val Leu Glu Glu Val Gln Gln Val Arg Arg Ser His Gln Asp Phe
    130                 135                 140
Ser Arg Gln Arg Glu Glu Leu Gly Gln Gly Leu Gln Gly Val Glu Gln
145                 150                 155                 160
Lys Val Gln Ser Leu Gln Ala Thr Phe Gly Thr Phe Glu Ser Ile Leu
                165                 170                 175
Arg Ser Ser Gln His Lys Gln Asp Leu Thr Glu Lys Ala Val Lys Gln
            180                 185                 190
Gly Glu Ser Glu Val Ser Arg Ile Ser Glu Val Leu Gln Lys Leu Gln
        195                 200                 205
Asn Glu Ile Leu Lys Asp Leu Ser Asp Gly Ile His Val Val Lys Asp
210                 215                 220
Ala Arg Glu Arg Asp Phe Thr Ser Leu Glu Asn Thr Val Glu Glu Arg
225                 230                 235                 240
Leu Thr Glu Leu Thr Lys Ser Ile Asn Asp Asn Ile Ala Ile Phe Thr
                245                 250                 255
Glu Val Gln Lys Arg Ser Gln Lys Glu Ile Asn Asp Met Lys Ala Lys
            260                 265                 270
Val Ala Ser Leu Glu Glu Ser Glu Gly Asn Lys Gln Asp Leu Lys Ala
        275                 280                 285
Leu Lys Glu Ala Val Lys Glu Ile Gln Thr Ser Ala Lys Ser Arg Glu
290                 295                 300
Trp Asp Met Glu Ala Leu Arg Ser Thr Leu Gln Thr Met Glu Ser Asp
305                 310                 315                 320
Ile Tyr Thr Glu Val Arg Glu Leu Val Ser Leu Lys Gln Glu Gln Gln
                325                 330                 335
Ala Phe Lys Glu Ala Ala Asp Thr Glu Arg Leu Ala Leu Gln Ala Leu
            340                 345                 350
Thr Glu Lys Leu Leu Arg Ser Glu Glu Ser Val Ser Arg Leu Pro Glu
        355                 360                 365
Glu Ile Arg Arg Leu Glu Glu Leu Arg Gln Leu Lys Ser Asp Ser
370                 375                 380
His Gly Pro Lys Glu Asp Gly Gly Phe Arg His Ser Glu Ala Phe Glu
385                 390                 395                 400
Ala Leu Gln Gln Lys Ser Gln Gly Leu Asp Ser Arg Leu Gln His Val
                405                 410                 415
Glu Asp Gly Val Leu Ser Met Gln Val Ala Ser Ala Arg Gln Thr Glu
            420                 425                 430
Ser Leu Glu Ser Leu Leu Ser Lys Ser Gln Glu His Glu Gln Arg Leu
        435                 440                 445
Ala Ala Leu Gln Gly Arg Leu Glu Gly Leu Gly Ser Ser Glu Ala Asp
450                 455                 460
Gln Asp Gly Leu Ala Ser Thr Val Arg Ser Leu Gly Glu Thr Gln Leu
465                 470                 475                 480
Val Leu Tyr Gly Asp Val Glu Glu Leu Lys Arg Ser Val Gly Glu Leu
                485                 490                 495
Pro Ser Thr Val Glu Ser Leu Gln Lys Val Gln Glu Gln Val His Thr
            500                 505                 510
Leu Leu Ser Gln Asp Gln Ala Gln Ala Ala Arg Leu Pro Pro Gln Asp
        515                 520                 525
Phe Leu Asp Arg Leu Ser Ser Leu Asp Asn Leu Lys Ala Ser Val Ser
530                 535                 540
Gln Val Glu Ala Asp Leu Lys Met Leu Arg Thr Ala Val Asp Ser Leu
```

```
                545                 550                 555                 560
Val Ala Tyr Ser Val Lys Ile Glu Thr Asn Glu Asn Asn Leu Glu Ser
                565                 570                 575

Ala Lys Gly Leu Leu Asp Asp Leu Arg Asn Asp Leu Asp Arg Leu Phe
                580                 585                 590

Val Lys Val Glu Lys Ile His Glu Lys Val
                595                 600

<210> SEQ ID NO 14
<211> LENGTH: 424
<212> TYPE: PRT
<213> ORGANISM: Homo sapiens

<400> SEQUENCE: 14

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
                20                  25                  30

Ala Lys Lys Pro Pro Ala Pro Gln Gln Pro Pro Pro Pro Pro Pro Ala
            35                  40                  45

Pro His Pro Gln Gln His Pro Gln Gln His Pro Gln Asn Gln Ala His
        50                  55                  60

Gly Lys Gly Gly His Arg Gly Gly Gly Gly Gly Gly Gly Lys Ser Ser
65              70                  75                  80

Ser Ser Ser Ser Ala Ser Ala Ala Ala Ala Ala Ala Ala Ser Ser
                85                  90                  95

Ser Ala Ser Cys Ser Arg Arg Leu Gly Arg Ala Leu Asn Phe Leu Phe
                100                 105                 110

Tyr Leu Ala Leu Val Ala Ala Ala Phe Ser Gly Trp Cys Val His
            115                 120                 125

His Val Leu Glu Glu Val Gln Gln Val Arg Arg Ser His Gln Asp Phe
        130                 135                 140

Ser Arg Gln Arg Glu Glu Leu Gly Gln Gly Leu Gln Gly Val Glu Gln
145                 150                 155                 160

Lys Val Gln Ser Leu Gln Ala Thr Phe Gly Thr Phe Glu Ser Ile Leu
                165                 170                 175

Arg Ser Ser Gln His Lys Gln Asp Leu Thr Glu Lys Ala Val Lys Gln
            180                 185                 190

Gly Glu Ser Glu Val Ser Arg Ile Ser Glu Val Leu Gln Lys Leu Gln
        195                 200                 205

Asn Glu Ile Leu Lys Asp Leu Ser Asp Gly Ile His Val Val Lys Asp
    210                 215                 220

Ala Arg Glu Arg Asp Phe Thr Ser Leu Glu Asn Thr Val Glu Glu Arg
225                 230                 235                 240

Leu Thr Glu Leu Thr Lys Ser Ile Asn Asp Asn Ile Ala Ile Phe Thr
                245                 250                 255

Glu Ser Leu Leu Ser Lys Ser Gln Glu His Glu Gln Arg Leu Ala Ala
            260                 265                 270

Leu Gln Gly Arg Leu Glu Gly Leu Gly Ser Ser Glu Ala Asp Gln Asp
        275                 280                 285

Gly Leu Ala Ser Thr Val Arg Ser Leu Gly Glu Thr Gln Leu Val Leu
    290                 295                 300

Tyr Gly Asp Val Glu Glu Leu Lys Arg Ser Val Gly Glu Leu Pro Ser
305                 310                 315                 320
```

```
Thr Val Glu Ser Leu Gln Lys Val Gln Glu Val His Thr Leu Leu
            325                 330                 335

Ser Gln Asp Gln Ala Gln Ala Ala Arg Leu Pro Pro Gln Asp Phe Leu
            340                 345                 350

Asp Arg Leu Ser Ser Leu Asp Asn Leu Lys Ala Ser Val Ser Gln Val
            355                 360                 365

Glu Ala Asp Leu Lys Met Leu Arg Thr Ala Val Asp Ser Leu Val Ala
        370                 375                 380

Tyr Ser Val Lys Ile Glu Thr Asn Glu Asn Asn Leu Glu Ser Ala Lys
385                 390                 395                 400

Gly Leu Leu Asp Asp Leu Arg Asn Asp Leu Asp Arg Leu Phe Val Lys
                405                 410                 415

Val Glu Lys Ile His Glu Lys Val
            420

<210> SEQ ID NO 15
<211> LENGTH: 602
<212> TYPE: PRT
<213> ORGANISM: Homo sapiens

<400> SEQUENCE: 15

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
            20                  25                  30

Ala Lys Lys Pro Pro Pro Ala Pro Gln Gln Pro Pro Pro Pro Pro Ala
            35                  40                  45

Pro His Pro Gln Gln His Pro Gln Gln His Pro Arg Asn Gln Ala His
        50                  55                  60

Gly Lys Gly Gly His Arg Gly Gly Gly Gly Gly Gly Gly Lys Ser Ser
65                  70                  75                  80

Ser Ser Ser Ser Ala Ser Ala Ala Ala Ala Ala Ala Ala Ala Ser Ser
                85                  90                  95

Ser Ala Ser Cys Ser Arg Arg Leu Gly Arg Ala Leu Asn Phe Leu Phe
            100                 105                 110

Tyr Leu Ala Leu Val Ala Ala Ala Phe Ser Gly Trp Cys Val His
            115                 120                 125

His Val Leu Glu Glu Val Gln Gln Val Arg Arg Ser His Gln Asp Phe
        130                 135                 140

Ser Arg Gln Arg Glu Glu Leu Gly Gln Gly Leu Gln Gly Val Glu Gln
145                 150                 155                 160

Lys Val Gln Ser Leu Gln Ala Thr Phe Gly Thr Phe Glu Ser Ile Leu
                165                 170                 175

Arg Ser Ser Gln His Lys Gln Asp Leu Thr Glu Lys Ala Val Lys Gln
            180                 185                 190

Gly Glu Ser Glu Val Ser Arg Ile Ser Glu Val Leu Gln Lys Leu Gln
            195                 200                 205

Asn Glu Ile Leu Lys Asp Leu Ser Asp Gly Ile His Val Val Lys Asp
        210                 215                 220

Ala Arg Glu Arg Asp Phe Thr Ser Leu Glu Asn Thr Val Glu Glu Arg
225                 230                 235                 240

Leu Thr Glu Leu Thr Lys Ser Ile Asn Asp Asn Ile Ala Ile Phe Thr
                245                 250                 255

Glu Val Gln Lys Arg Ser Gln Lys Glu Ile Asn Asp Met Lys Ala Lys
            260                 265                 270
```

```
Val Ala Ser Leu Glu Glu Ser Glu Gly Asn Lys Gln Asp Leu Lys Ala
            275                 280                 285

Leu Lys Glu Ala Val Lys Glu Ile Gln Thr Ser Ala Lys Ser Arg Glu
        290                 295                 300

Trp Asp Met Glu Ala Leu Arg Ser Thr Leu Gln Thr Met Glu Ser Asp
305                 310                 315                 320

Ile Tyr Thr Glu Val Arg Glu Leu Val Ser Leu Lys Gln Glu Gln Gln
                325                 330                 335

Ala Phe Lys Glu Ala Ala Asp Thr Glu Arg Leu Ala Leu Gln Ala Leu
            340                 345                 350

Thr Glu Lys Leu Leu Arg Ser Glu Ser Val Ser Arg Leu Pro Glu
        355                 360                 365

Glu Ile Arg Arg Leu Glu Glu Leu Arg Gln Leu Lys Ser Asp Ser
        370                 375                 380

His Gly Pro Lys Glu Asp Gly Gly Phe Arg His Ser Glu Ala Phe Glu
385                 390                 395                 400

Ala Leu Gln Gln Lys Ser Gln Gly Leu Asp Ser Arg Leu Gln His Val
                405                 410                 415

Glu Asp Gly Val Leu Ser Met Gln Val Ala Ser Ala Arg Gln Thr Glu
            420                 425                 430

Ser Leu Glu Ser Leu Leu Ser Lys Ser Gln Glu His Glu Gln Arg Leu
        435                 440                 445

Ala Ala Leu Gln Gly Arg Leu Glu Gly Leu Gly Ser Ser Glu Ala Asp
        450                 455                 460

Gln Asp Gly Leu Ala Ser Thr Val Arg Ser Leu Gly Glu Thr Gln Leu
465                 470                 475                 480

Val Leu Tyr Gly Asp Val Glu Glu Leu Lys Arg Ser Val Gly Glu Leu
                485                 490                 495

Pro Ser Thr Val Glu Ser Leu Gln Lys Val Gln Glu Gln Val His Thr
            500                 505                 510

Leu Leu Ser Gln Asp Gln Ala Gln Ala Ala Arg Leu Pro Pro Gln Asp
        515                 520                 525

Phe Leu Asp Arg Leu Ser Ser Leu Asp Asn Leu Lys Ala Ser Val Ser
        530                 535                 540

Gln Val Glu Ala Asp Leu Lys Met Leu Arg Thr Ala Val Asp Ser Leu
545                 550                 555                 560

Val Ala Tyr Ser Val Lys Ile Glu Thr Asn Glu Asn Leu Glu Ser
                565                 570                 575

Ala Lys Gly Leu Leu Asp Asp Leu Arg Asn Asp Leu Asp Arg Leu Phe
            580                 585                 590

Val Lys Val Glu Lys Ile His Glu Lys Val
        595                 600

<210> SEQ ID NO 16
<211> LENGTH: 602
<212> TYPE: PRT
<213> ORGANISM: Homo sapiens

<400> SEQUENCE: 16

Met Pro Ser Ala Lys Gln Arg Gly Ser Lys Gly His Gly Ala Ala
1               5                   10                  15

Ser Pro Ser Glu Lys Gly Ala His Pro Ser Gly Gly Ala Asp Asp Val
            20                  25                  30

Ala Lys Lys Pro Pro Pro Ala Pro Gln Gln Pro Pro Pro Pro Pro Ala
```

```
                35                  40                  45
Pro His Pro Gln Gln His Pro Gln Gln His Pro Gln Asn Gln Ala His
     50                  55                  60
Gly Lys Gly Gly His Arg Gly Gly Gly Gly Gly Gly Lys Ser Ser
 65                  70                  75                  80
Ser Ser Ser Ser Ala Ser Ala Ala Ala Ala Ala Ala Ala Ser Ser
                 85                  90                  95
Ser Ala Ser Cys Ser Arg Arg Leu Gly Arg Ala Leu Asn Phe Leu Phe
                100                 105                 110
Tyr Leu Ala Leu Val Ala Ala Ala Phe Ser Gly Trp Cys Val His
            115                 120                 125
His Val Leu Glu Glu Val Gln Gln Val Arg Arg Ser His Gln Asp Phe
        130                 135                 140
Ser Arg Gln Arg Glu Glu Leu Gly Gln Gly Leu Gln Gly Val Glu Gln
145                 150                 155                 160
Lys Val Gln Ser Leu Gln Ala Thr Phe Gly Thr Phe Glu Ser Ile Leu
                165                 170                 175
Arg Ser Ser Gln His Lys Gln Asp Leu Thr Glu Lys Ala Val Lys Gln
                180                 185                 190
Gly Glu Ser Glu Val Ser Arg Ile Ser Glu Val Leu Gln Lys Leu Gln
            195                 200                 205
Asn Glu Ile Leu Lys Asp Leu Ser Asp Gly Ile His Val Val Lys Asp
210                 215                 220
Ala Arg Glu Arg Asp Phe Thr Ser Leu Glu Asn Thr Val Glu Glu Arg
225                 230                 235                 240
Leu Thr Glu Leu Thr Lys Ser Ile Asn Asp Asn Ile Ala Ile Phe Thr
                245                 250                 255
Glu Val Gln Lys Arg Ser Gln Lys Glu Ile Asn Asp Met Lys Ala Lys
                260                 265                 270
Val Ala Ser Leu Glu Glu Ser Glu Gly Asn Lys Gln Asp Leu Lys Ala
            275                 280                 285
Leu Lys Glu Ala Val Lys Glu Ile Gln Thr Ser Ala Lys Ser Arg Glu
        290                 295                 300
Trp Asp Met Glu Ala Leu Arg Ser Thr Leu Gln Thr Met Glu Ser Asp
305                 310                 315                 320
Ile Tyr Thr Glu Val Arg Glu Leu Val Ser Leu Lys Gln Glu Gln Gln
                325                 330                 335
Ala Phe Lys Glu Ala Ala Asp Thr Glu Arg Leu Ala Leu Gln Ala Leu
            340                 345                 350
Thr Glu Lys Leu Leu Arg Ser Glu Glu Ser Val Ser Arg Leu Pro Glu
        355                 360                 365
Glu Ile Arg Arg Leu Glu Glu Leu Arg Gln Leu Lys Ser Asp Ser
        370                 375                 380
His Gly Pro Lys Glu Asp Gly Gly Phe Arg His Ser Glu Ala Phe Glu
385                 390                 395                 400
Ala Leu Gln Gln Lys Ser Gln Gly Leu Asp Ser Arg Leu Gln His Val
                405                 410                 415
Glu Asp Gly Val Leu Ser Met Gln Val Ala Ser Ala Arg Gln Thr Glu
            420                 425                 430
Ser Leu Glu Ser Leu Leu Ser Lys Ser Gln Glu His Glu Gln Arg Leu
        435                 440                 445
Ala Ala Leu Gln Gly Arg Leu Glu Gly Leu Gly Ser Ser Glu Ala Asp
        450                 455                 460
```

```
Gln Asp Gly Leu Ala Ser Thr Val Arg Ser Leu Gly Glu Thr Gln Leu
465                 470                 475                 480

Val Leu Tyr Gly Asp Val Glu Glu Leu Lys Arg Ser Val Gly Glu Leu
                485                 490                 495

Pro Ser Thr Val Glu Ser Leu Gln Lys Val Gln Glu Val His Thr
            500                 505                 510

Leu Leu Ser Gln Asp Gln Ala Gln Ala Ala Arg Leu Pro Pro Gln Asp
        515                 520                 525

Phe Leu Asp Arg Leu Ser Ser Leu Asp Asn Leu Lys Ala Ser Val Ser
    530                 535                 540

Gln Val Glu Ala Asp Leu Lys Met Leu Arg Thr Ala Val Asp Ser Leu
545                 550                 555                 560

Val Ala Tyr Ser Val Lys Ile Glu Thr Asn Glu Asn Asn Leu Glu Ser
                565                 570                 575

Ala Lys Gly Leu Leu Asp Asp Leu Arg Asn Asp Leu Asp Arg Leu Phe
            580                 585                 590

Val Lys Val Glu Lys Ile His Glu Lys Val
        595                 600
```

<210> SEQ ID NO 17
<211> LENGTH: 1809
<212> TYPE: DNA
<213> ORGANISM: Homo sapiens

<400> SEQUENCE: 17

```
atgccctcgg ccaaacaaag gggctccaag ggcggccacg cgccgcgag ccctcggag      60
aagggtgccc acccgtcggg cggcgcggat gacgtggcga agaagccgcc gccggcgccg     120
cagcagccgc cgccgccgcc cgcgccgcac ccgcagcagc accgcagca gcacccgcag     180
aaccaggcgc acggcaaggg cggccaccgc ggcggcggcg gcggcggcgg caagtcctcc     240
tcctcctcct ccgcctccgc cgccgctgcc gccgccgccg cctcgtcctc ggcgtcctgc     300
tcgcgcaggc tcggcagggc gctcaacttt ctcttctacc tcgccctggt ggcggcggcc     360
gctttctcgg gctggtgcgt ccaccacgtc ctggaggagg tccagcaggt ccggcgcagc     420
caccaggact tctcccggca gaggaggag ctgggccagg gcttgcaggg cgtcgagcag     480
aaggtgcagt ctttgcaagc cacatttgga acttttgagt ccatcttgag aagctcccaa     540
cataaacaag acctcacaga gaaagctgtg aagcaagggg agagtgaggt cagccggatc     600
agcgaagtgc tgcagaaact ccagaatgag attctcaaag acctctcgga tgggatccat     660
gtggtgaagg acgcccggga gcgggacttc acgtccctgg agaacacggt ggaggagcgg     720
ctgacggagt caccaaatc catcaacgac aacatcgcca tcttcacaga agtccagaag     780
aggagccaga aggagatcaa tgacatgaag gcaaaggttg cctccctgga gaatctgag     840
ggaacaagc aggatttgaa agccttaaag gaagctgtga aggagataca gacctcagcc     900
aagtccagag agtgggacat ggaggccctg agaagtaccc ttcagactat ggagtctgac     960
atctacaccg aggtccgcga gctggtgagc ctcaagcagg agcagcaggc tttcaaggag    1020
gcggccgaca cggagcggct cgccctgcag gccctcacgg agaagcttct caggtctgag    1080
gagtccgtct cccgcctccc ggaggagatc cggagactgg aggaagagct ccgccagctg    1140
aagtccgatt cccacggggcc gaaggaggac ggaggcttca gacactcgga agcctttgag    1200
gcactccagc aaaagagtca gggactggac tccaggctcc agcacgtgga ggatggggtg    1260
ctctccatgc aggtggcttc tgcgcgccag accgagagcc tggagtccct cctgtccaag    1320
```

```
agccaggagc acgagcagcg cctggccgcc ctgcaggggc gcctggaagg cctcgggtcc    1380
tcagaggcag accaggatgg cctggccagc acggtgagga gcctgggcga gacccagctg    1440
gtgctctacg gtgacgtgga ggagctgaag aggagtgtgg gcgagctccc cagcaccgtg    1500
gaatcactcc agaaggtgca ggagcaggtg cacacgctgc tcagtcagga ccaagcccag    1560
gccgcccgtc tgcctcctca ggacttcctg gacagacttt cttctctaga caacctgaaa    1620
gcctcagtca gccaagtgga ggcggacttg aaaatgctca ggactgctgt ggacagtttg    1680
gttgcatact cggtcaaaat agaaaccaac gagaacaatc tggaatcagc caagggttta    1740
ctagatgacc tgaggaatga tctggatagg ttgtttgtga agtggagaa gattcacgaa     1800 aaggtctaa                                                            1809
```

<210> SEQ ID NO 18
<211> LENGTH: 1581
<212> TYPE: DNA
<213> ORGANISM: Homo sapiens
<400> SEQUENCE: 18

```
atgccctcgg ccaaacaaag gggctccaag ggcggccacg gcgccgcgag cccctcggag      60
aagggtgccc acccgtcggg cggcgcggat gacggcgctc aactttctct tctacctcgc     120
cctgcggcgg ccgctttctc gggctggtgc gtccaccacg tcctgaggga ggtccagcag     180
gtccggcgca gccaccagga cttctcccgg cagagggagg agctgggcca gggcttgcag     240
ggcgtcgagc agaaggtgca gtcttttgcaa gccacatttg gaacttttga gtccatcttg     300
agaagctccc aacataaaca agacctcaca gagaaagctg tgaagcaagg ggagagtgag     360
gtcagccgga tcagcgaagt gctgcagaaa ctccagaatg agattctcaa agacctctcg     420
gatgggatcc atgtggtgaa ggacgcccgg gagcgggact tcacgtccct ggagaacacg     480
gtggaggagc ggctgacgga gctcaccaaa tccatcaacg acaacatcgc catcttcaca     540
gaagtccaga gaggagccaa gaggagatc aatgacatga aggcaaaggt tgcctccctg     600
gaagaatctg aggggaacaa gcaggatttg aaagccttaa aggaagctgt gaaggagata     660
cagacctcag ccaagtccag agagtgggac atggaggccc tgagaagtac ccttcagact     720
atggagtctg acatctacac cgaggtccgc gagctggtga gcctcaagca ggagcagcag     780
gctttcaagg aggcggccga cacggagcgg ctcgccctgc aggccctcac ggagaagctt     840
ctcaggtctg aggagtccgt ctcccgcctc ccggaggaga tccggagact ggaggaagag     900
ctccgccagc tgaagtccga ttcccacggg ccgaaggagg acgaggctt cagacactcg     960 gaagcctttg aggcactcca gcaaagagt cagggactgg actccaggct ccagcacgtg    1020
gaggatgggt tgctctccat gcaggtggct tctgcgcgcc agaccgagag cctggagtcc    1080
ctcctgtcca agagccagga gcacgagcag cgcctggccg ccctgcaggg gcgcctggaa    1140
ggcctcgggt cctcagaggc agaccaggat ggcctggcca gcacggtgag gagcctgggc    1200
gagacccagc tggtgctcta cggtgacgtg gaggagctga agaggagtgt gggcgagctc    1260
cccagcaccg tggaatcact ccagaaggtg caggagcagg tgcacacgct gctcagtcag    1320
gaccaagccc aggccgcccg tctgcctcct caggacttcc tggacagact tcttctcta     1380 gacaacctga aagcctcagt cagccaagtg gaggcggact tgaaaatgct caggactgct    1440
gtggacagtt tggttgcata ctcggtcaaa atagaaacca acgagaacaa tctggaatca    1500
gccaagggtt tactagatga cctgaggaat gatctggata ggttgtttgt gaaagtggag    1560
```

```
aagattcacg aaaaggtcta a                                              1581

<210> SEQ ID NO 19
<211> LENGTH: 1776
<212> TYPE: DNA
<213> ORGANISM: Homo sapiens

<400> SEQUENCE: 19
gctcgctcgc ctcccagccc gcggcccgag ccgccgccgc gcccgccatg ccctcggcca     60
aacaaagggg ctccaagggc ggccacggcg ccgcgagccc ctcggagaag ggtgccacc    120
cgtcgggcgg cgcggatgac gtggcgaaga agccgccgcc ggcgccgcag cagccgccgc   180
cgccgcccgc gccgcacccg cagcagcacc cgcagcagca cccgcagaac caggcgcacg   240
gcaagggcgg ccaccgcggc ggcgcggcg cggcgctcg gcagggcgct caactttctc    300
ttctacctcg ccctggtggc ggcggccgct ttctcgggct ggtgcgtcca ccacgtcctg   360
gaggaggtcc agcaggtccg gcgcagccac caggacttct cccggcagag ggaggagctg   420
ggccagggct gcagggcgt cgagcagaag gtgcagtctt tgcaagccac atttggaact    480
tttgagtcca tcttgagaag ctcccaacat aaacaagacc tcacagagaa agctgtgaag   540
caaggggaga gtgaggtcag ccggatcagc gaagtgctgc agaaactcca gaatgagatt   600
ctcaaagacc tctcggatgg gatccatgtg gtgaaggacg cccgggagcg ggacttcacg   660
tccctggaga cacggtgga ggagcggctg acggagctca ccaaatccat caacgacaac    720
atcgccatct tcacagaagt ccagaagagg agccagaagg agatcaatga catgaaggca   780
aaggttgcct ccctggaaga atctgagggg aacaagcagg atttgaaagc cttaaaggaa   840
gctgtgaagg agatacagac ctcagccaag tccagagagt gggacatgga ggccctgaga   900
agtacccttc agactatgga gtctgacatc tacaccgagg tccgcgagct ggtgagcctc   960
aagcaggagc agcaggcttt caaggaggcg ccgacacgg agcggctcgc cctgcaggcc   1020
ctcacggaga gcttctcag gtctgaggag tccgtctccc gcctcccgga ggagatccgg  1080
agactggagg aagagctccg ccagctgaag tccgattccc acgggccgaa ggaggacgga  1140
ggcttcagac actcggaagc cttttgaggca ctccagcaaa agagtcaggg actggactcc  1200
aggctccagc acgtggagga tggggtgctc tccatgcagg tggcttctgc gcgccagacc  1260
gagagcctgg agtccctcct gtccaagagc aggagcacg agcagcgcct ggccgccctg   1320
cagggcgcc tggaaggcct cgggtcctca gaggcagacc aggatggcct ggccagcacg  1380
gtgaggagcc tgggcgagac ccagctggtg ctctacggtg acgtggagga gctgaagagg  1440
agtgtgggcg agctccccag caccgtggaa tcactccaga aggtgcagga gcaggtgcac  1500
acgctgctca gtcaggacca agcccaggcc gccgtctgc ctcctcagga cttcctggac  1560
agactttctt ctctagacaa cctgaaagcc tcagtcagcc aagtggaggc ggacttgaaa  1620
atgctcagga ctgctgtgga cagtttggtt gcatactcgg tcaaaataga aaccaacgag  1680
aacaatctgg aatcagccaa gggtttacta gatgacctga ggaatgatct ggataggttg  1740
tttgtgaaag tggagaagat tcacgaaaag gtctaa                             1776

<210> SEQ ID NO 20
<211> LENGTH: 2913
<212> TYPE: DNA
<213> ORGANISM: Homo sapiens

<400> SEQUENCE: 20
gggggagccc ctgcaagttt cccgggccgc gcgccgcgct cgctcgcctc ccagcccgcg    60
```

-continued

| | |
|---|---|
| gcccgagccg ccgccgcgcc cgccatgccc tcggccaaac aaaggggctc caagggcggc | 120 |
| cacggcgccg cgagcccctc ggagaagggt gcccacccgt cgggcggcgc ggatgacgtg | 180 |
| gcgaagaagc cgccgccggc gccgcagcag ccgccgccgc cgcccgcgcc gcacccgcag | 240 |
| cagcacccgc agcagcaccc gcagaaccag gcgcacggca agggcggcca ccgcggcggc | 300 |
| ggcggcggcg gcggcaagtc ctcctcctcc tcctccgcct ccgccgccgc tgccgccgcc | 360 |
| gccgcctcgt cctcggcgtc ctgctcgcgc aggctcggca gggcgctcaa ctttctcttc | 420 |
| tacctcgccc tggtggcggc ggccgctttc tcgggctggt gcgtccacca cgtcctggag | 480 |
| gaggtccagc aggtccggcg cagccaccag gacttctccc ggcagaggga ggagctgggc | 540 |
| cagggcttgc agggcgtcga gcagaaggtg cagtctttgc aagccacatt tggaactttt | 600 |
| gagtccatct tgagaagctc ccaacataaa caagacctca cagagaaagc tgtgaagcaa | 660 |
| ggggagagtg aggtcagccg gatcagcgaa gtgctgcaga aactccagaa tgagattctc | 720 |
| aaagacctct cggatgggat ccatgtggtg aaggacgccc gggagcggga cttcacgtcc | 780 |
| ctggagaaca cggtggagga gcggctgacg gagctcacca aatccatcaa cgacaacatc | 840 |
| gccatcttca cagaagtcca gaagaggagc cagaaggaga tcaatgacat gaaggcaaag | 900 |
| gttgcctccc tggaagaatc tgaggggaac aagcaggatt tgaaagcctt aaaggaagct | 960 |
| gtgaaggaga tacagacctc agccaagtcc agagagtggg acatggaggc cctgagaagt | 1020 |
| acccttcaga ctatggagtc tgacatctac accgaggttc gcgagctggt gagcctcaag | 1080 |
| caggagcagc aggcttttca aggaggcggc gacacggagc ggctcgccct gcaggccctc | 1140 |
| acggagaagc ttctcaggtc tgaggagtcc gtctcccgcc tcccggagga gatccggaga | 1200 |
| ctggaggaag agctccgcca gctgaagtcc gattcccacg ggccgaagga ggacggaggc | 1260 |
| ttcagacact cggaagcctt tgaggcactc cagcaaaaga gtcagggact ggactccagg | 1320 |
| ctccagcacg tggaggatgg ggtgctctcc atgcaggtgg cttctgcgcg ccagaccgag | 1380 |
| agcctggagt ccctcctgtc caagagccag gagcacgagc agcgcctggc cgccctgcag | 1440 |
| gggcgcctgg aaggcctcgg gtcctcagag gcagaccagg atggcctggc cagcacggtg | 1500 |
| aggagcctgg gcgagaccca gctggtgctc tacggtgacg tggaggagct gaagaggagt | 1560 |
| gtgggcgagc tccccagcac cgtggaatca ctccagaagg tgcaggagca ggtgcacacg | 1620 |
| ctgctcagtc aggaccaagc ccaggccgcc cgtctgcctc ctcaggactt cctggacaga | 1680 |
| cttt cttctc tagacaacct gaaagcctca gtcagccaag tggaggcgga cttgaaaatg | 1740 |
| ctcaggactg ctgtggacag tttggttgca tactcggtca aaatagaaac caacgagaac | 1800 |
| aatctggaat cagccaaggg tttactagat gacctgagga atgatctgga taggttgttt | 1860 |
| gtgaaagtgg agaagattca cgaaaaggtc taaatgaatt gcgtgtgcag ggcgcggatt | 1920 |
| taaagtccaa tttctcatga ccaaaaaatg tgtggttttt tcccatgtgt ccctaccccc | 1980 |
| ccaatttctt gtccctctct aaagagcagt tgtcaccacc tgaacaccaa ggcattgtat | 2040 |
| tttcatgccc agtaacttaa tttacaatat ttaagttctc tgcttctgca tttggttggt | 2100 |
| ttcctgaagc gcagcccctg tgaataacag gtggcttttc atggatgtct ctagtcagag | 2160 |
| aaaaatgata aaggcttaaa ttgaggatta acagaagcag attaacctca gaaatcctgt | 2220 |
| ctggctggca gatttcaagt aaaaaaaaaa aaaggtgggt tgggggggac ccttttcttt | 2280 |
| ctagttgtct ttaaggaaaa ttaattttac ttttttttt gttctggccg aaattttat | 2340 |
| gagatatctc tcacttgtct tccactttga accggttaaa gctcatagct gtcagctctg | 2400 |

```
aatgaggagg ggagaagccc ctgggtctct ctttgaaagg aatccgctgc ttgagggctg    2460
cctccctcat ggtgtgcgtg tcgttctctt cctgacgcat ctgtgatatc agaggtaact    2520
atgcaaagca tccaggcggt tctgaatgtg aagcactaca cccagcagag tcccggtgcc    2580
ctctgtcccc actgccggcc catgtcctct tccggaggt caccaaggaa tgcacaggtt    2640
tcgactacca gaaaggggag tccttgggtt ctttcaaaaa attcgtgagg agagctgtct    2700
acagtggaat aggggtctc cctggggaat gcaggccaag tccttttatt ttaacatgat    2760
gtccatgaag aggtttgccg tctgggcagc cctgtcggca aggagcgtgc atactgcgtt    2820
tgtgtaattg tttgctgtat ctcccttccc tctgagctgt attgttcttt aatggctgtc    2880
ttgcccttcc aaaaaaaatt gaaaaaaaaa aaa                                2913
```

```
<210> SEQ ID NO 21
<211> LENGTH: 2231
<212> TYPE: DNA
<213> ORGANISM: Homo sapiens

<400> SEQUENCE: 21
```

```
agccaatggg gctcgctcgc ctcccagccc gcggcccgag ccgccgccgc gcccgccatg      60 cccctcggcca aacaaggggg ctccaagggc ggccacggcg ccgcgagccc ctcggagaag    120
ggtgcccacc cgtcgggcgg cgcggatgac gtggcgaaga agccgccgcc ggcgccgcag    180
cagccgccgc cgccgcccgc gccgcacccg cagcagcacc cgcagcagca cccgcagaac    240
caggcgcacg gcaagggcgg ccaccgcggc ggcggcggcg gcggcggcaa gtcctcctcc    300
tcctcctccg cctccgccgc cgctgccgcc ccgccgcct cgtcctcggc gtcctgctcg    360
cgcaggctcg gcagggcgct caactttctc ttctacctcg ccctggtggc ggcggccgct    420
ttctcgggct ggtgcgtcca ccacgtcctg gaggaggtcc agcaggtccg gcgcagccac    480
caggacttct cccggcagag ggaggagctg gccagggct tgcagggcgt cgagcagaag    540
gtgcagtctt tgcaagccac atttggaact tttgagtcca tcttgagaag ctcccaacat    600
aaacaagacc tcacagagaa agctgtgaag caaggggaga gtgaggtcag ccggatcagc    660
gaagtgctgc agaaactcca gaatgagatt ctcaaagacc tctcggatgg gatccatgtg    720
gtgaaggacg cccgggagcg ggacttcacg tccctggaga cacggtgga ggagcggctg    780 acggagctca ccaaatccat caacgacaac atcgccatct tcacagaagt ccagaagagg    840
agccagaagg agatcaatga catgaaggca aaggttgcct ccctggaaga atctgagggg    900
aacaagcagg atttgaaagc cttaaaggaa gctgtgaagg agatacagac ctcagccaag    960
tccagagagt gggacatgga ggccctgaga agtacccttc agactatgga gtctgacatc   1020
tacaccgagg tccgcgagct ggtgagcctc aagcaggagc agcaggcttt caaggaggcg   1080
gccgacacgg agcggctcgc cctgcaggcc tcacggagag gcttctcag gtctgaggag   1140 tccgtctccc gcctcccgga ggagatccgg agactggagg aagagctccg ccagctgaag   1200
tccgattccc acgggccgaa ggaggacgga ggcttcagac actcggaagc ctttgaggca   1260
ctccagcaaa agagtcaggg actggactcc aggctccagc acgtggagga tggggtgctc   1320
tccatgcagg tggcttctgc gcgccagacc gagagcctgg agtccctcct gtccaagagc   1380
caggagcacg agcagcgcct ggccgccctg caggggcgcc tggaaggcct cgggtcctca   1440
gaggcagacc aggatggcct ggccagcacg gtgaggagcc tgggcgagac ccagctggtg   1500
ctctacggtg acgtggagga gctgaagagg agtgtgggcg agctcccag caccgtggaa   1560 tcactccaga aggtgcagga gcaggtgcac acgctgctca gtcaggacca agcccaggcc   1620
```

```
gcccgtctgc ctcctcagga cttcctggac agactttctt ctctagacaa cctgaaagcc    1680
tcagtcagcc aagtggaggc ggacttgaaa atgctcagga ctgctgtgga cagtttggtt    1740
gcatactcgg tcaaaataga aaccaacgag aacaatctgg aatcagccaa gggtttacta    1800
gatgacctga ggaatgatct ggataggttg tttgtgaaag tggagaagat tcacgaaaag    1860
gtctaaatga attgcgtgtg cagggcgcgg atttaaagtc caatttctca tgaccaaaaa    1920
atgtgtggtt ttttcccatg tgtcccctac cccccaattt cttgtcccct cttaaagagc    1980
agttgtcacc acctgaacac caaggcattg tattttcatg cccagttaac ttatttacaa    2040
tatttaagtt ctctgcttct gcatttggtt ggtttcctga agcgcagccc ctgtgaataa    2100
caggtggctt ttcatggatg tctctagtca gagaaaaatg ataaaggctt aaattgagga    2160
ttaacagaag cagattaacc tcagaaatcc tgtctggctg gcagatttca agtaaaaaaa    2220
aaaaaaaaaa a                                                         2231

<210> SEQ ID NO 22
<211> LENGTH: 2039
<212> TYPE: DNA
<213> ORGANISM: Homo sapiens

<400> SEQUENCE: 22
gcgtgccgct cgcccagtcc cggggagcc cctgcaagtt tcccgggccg cgcgccgcgc       60
tcgctcgcct cccagcccgc ggcccgagcc gccgccgcgc ccgccatgcc ctcggccaaa    120
caaaggggct ccaagggcgg ccacggcgcc gcgagcccct cggagaaggg tgcccacccg    180
tcgggcggcg cggatgacgt ggcgaagaag ccgccgccgg cggccgcttt ctcgggctgg    240
tgcgtccacc acgtcctgga ggaggtccag caggtccggc gcagccacca ggacttctcc    300
cggcagaggg aggagctggg ccaggcttg cagggcgtcg agcagaaggt gcagtctttg    360
caagccacat ttggaacttt tgagtccatc ttgagaagct cccaacataa acaagacctc    420
acagagaaag ctgtgaagca aggggagagt gaggtcagcc ggatcagcga agtgctgcag    480
aaactccaga tgagattct caaagacctc tcggatggga tccatgtggt gaaggacgcc    540
cgggagcggg acttcacgtc cctggagaac acggtggagg agcggctgac ggagctcacc    600
aaatccatca acgacaacat cgccatcttc acagaagtcc agaagaggag ccagaaggag    660
atcaatgaca tgaaggcaaa ggttgcctcc ctggaagaat ctgaggggaa caagcaggat    720
ttgaaagcct taaaggaagc tgtgaaggag atacagacct cagccaagtc cagagagtgg    780
gacatggagg ccctgagaag tacccttcag actatggagt ctgacatcta caccgaggtc    840
cgcgagctgg tgagcctcaa gcaggagcag caggctttca aggaggcggc cgacacggag    900
cggctcgccc tgcaggccct cacgagaag cttctcaggt ctgaggagcc cgtctcccgc    960
ctcccggagg agatccggag actggaggaa gagctccgcc agctgaagtc cgattcccac    1020
gggccgaagg aggacggagg cttcagacac tcggaagcct tgaggcact ccagcaaaag    1080 agtcagggac tggactccag gctccagcac gtggaggatg gggtgctctc catgcaggtg    1140
gcttctgcgc gccagaccga gagcctggag tccctcctgt ccaagagcca ggagcacgag    1200
cagcgcctgg ccgccctgca ggggcgcctg aaggcctcg gtcctcaga ggcagaccag    1260 gatggcctgg ccagcacggt gaggagcctg gcgagaccc agctggtgct ctacggtgac    1320
gtggaggagc tgaagaggag tgtgggcgag ctccccagca ccgtggaatc actccagaag    1380
gtgcaggagc aggtgcacac gctgctcagt caggaccaag cccaggccgc ccgtctgcct    1440
```

-continued

| | | | | | |
|---|---|---|---|---|---|
| cctcaggact | tcctggacag | actttcttct | ctagacaacc | tgaaagcctc | agtcagccaa | 1500 |
| gtggaggcgg | acttgaaaat | gctcaggact | gctgtggaca | gtttggttgc | atactcggtc | 1560 |
| aaaatagaaa | ccaacgagaa | caatctggaa | tcagccaagg | gtttactaga | tgacctgagg | 1620 |
| aatgatctgg | ataggttgtt | tgtgaaagtg | gagaagattc | acgaaaaggt | ctaaatgaat | 1680 |
| tgcgtgtgca | gggcgcggat | ttaaagtcca | atttctcatg | accaaaaaat | gtgtggtttt | 1740 |
| ttcccatgtg | tcccctaccc | cccaatttct | tgtcccctct | taaagagcag | ttgtcaccac | 1800 |
| ctgaacacca | aggcattgta | ttttcatgcc | cagttaactt | atttacaata | tttaagttct | 1860 |
| ctgcttctgc | atttggttgg | tttcctgaag | cgcagcccct | gtgaataaca | ggtggctttt | 1920 |
| catggatgtc | tctagtcaga | gaaaaatgat | aaaggcttaa | attgaggatt | aacagaagca | 1980 |
| gattaacctc | agaaatcctg | tctggctggc | agatttcaag | taaaaaaaaa | aaaaaaaaa | 2039 |

CELL-BASED DETECTION OF APF THROUGH ITS INTERACTION WITH CKAP4 FOR DIAGNOSIS OF INTERSTITIAL CYSTITIS

BACKGROUND OF THE INVENTION

1. Field of Invention

This invention relates to an assay system designed to detect a protein biomarker in urine that is diagnostic for interstitial cystitis (IC). The cytoskeletal associated protein 4 (CKAP4) is subcloned in frame with yellow-fluorescent protein (YFP) creating a fusion protein (CKAP4-YFP). CKAP4-YFP is ectopically expressed in the human cervical carcinoma cell line, HeLa, at the cell surface, creating a cell-based system. Urine samples from patients who exhibit symptoms consistent with IC are added to the cell-based system. The presence of a 9 amino acid glycopeptide, antiproliferative factor (APF), in urine is unique to patients with IC. APF specifically binds to CKAP4-YFP at the cell surface. Binding of APF to CKAP4-YFP enables transit of CKAP4-YFP-APF to the nucleus. Transit of this protein complex to the nucleus is measured using high-throughput immunofluorescence microscopy. Nuclear localization of the YFP signal is positive for the presence of APF in urine and diagnostic for IC. The cell-based diagnostic system is a significant and surprising advance in diagnosis of IC and has commercial applications relevant to greater than 147/100,000 women and 41/100,000 men who suffer from symptoms consistent with IC.

2. Description of Related Art

Interstitial cystitis/painful bladder syndrome (IC/PBS) is a poorly understood, chronic, urinary bladder disease manifested by bladder pain and increased frequency and urgency of urination (Sant and Hanno, 2001). IC has no single, definable presentation, but is best viewed as a continuum extending across decades of an individual's life, beginning with mild, intermittent symptoms that become more severe and constant over time. For many, pain is the most dominating and debilitating symptom, becoming so severe as the disease progresses that it significantly affects patients' quality of life (Marshall, 2003). As many as 1.3 million American men, women, and children of all ages and races have IC; however, the disease is far more common in women (Clemens et al, 2007). Approximately 60/100,000 adult American women are affected, with more recent studies suggesting a substantially higher prevalence (Curhan et al, 1999; Leppilahti et al, 2005). Indeed, the prevalence in the managed care population was 197/100,000 for women and 41/100,000 for men when diagnosed using ICD-9 code (Clemens et al, 2005). Because the causes of IC are unknown, current treatments are aimed only at providing symptom relief. Many patients have noted an improvement in symptoms after bladder distention has been performed to diagnose the condition; however, researchers are not sure why this helps. Bladder instillation (also called a bladder wash or bath) with dimethyl sulfoxide given every week or two for 6 to 8 weeks has also been noted to improve symptoms temporarily. Because DMSO passes into the bladder wall during this procedure, physicians believe that it may reach tissue more effectively to reduce inflammation, block pain, and also prevent muscle contractions that cause pain, frequency, and urgency. Pentosan polysulfate sodium (the first oral drug developed for IC; Elmiron) given orally (100 mg three times a day) has improved symptoms in 30% of patients. Bacillus Calmette-Guerin (BCG), a common intravesicular agent used in bladder cancer, has also been shown to improve symptoms (Peters et al, 1998). Electrical nerve stimulation and lifestyle interventions, including dietary modifications, bladder training, and exercise, are other approaches to symptom relief. Surgical procedures such as fulguration and resection of ulcers, bladder augmentation, or bladder removal (cystectomy) are a consideration only if all available treatments have failed and if the pain is disabling; however, most surgeons are reluctant to operate because some patients still have symptoms after surgery.

IC presents with symptoms that are identical to those detected in patients with bacterial infections and other disorders of the urogenital tract (Table 1) (Wein et al, 1990). In addition to the diseases listed in Table 1, differential diagnosis includes several other possibilities, including overactive bladder (although these patients do not have bladder pain), chronic urinary tract infection in an otherwise normal urinary tract, vulvodynia (or tender vulva) which may coexist with IC, and endometriosis which may also coexist with IC. These conditions are individually treated using different clinical approaches. Significantly, there is no commercially available diagnostic test for IC, making it difficult to distinguish it from other conditions with similar symptomology and difficult to develop an appropriate treatment strategy. These gaps in knowledge directly affect patient care: in the past, patients experienced an average lag time of five to seven years before they received a diagnosis of IC (Curhan et al, 1999). With current prevalence estimates for IC in the managed care population of 197/100,000 for women and 41/100,000 for men (Clemens et al, 2005), hundreds of thousands of people would have to be screened in order to differentiate IC from other conditions (Clemens et al, 2005). At present the only available diagnostic specific to IC is an ulcer of the bladder mucosa, which is called Hunner's ulcer. Unfortunately, this condition is not very helpful for the purposes of diagnosis because it is found in 10% or fewer IC cases (Sant and Hanno, 2001). Thus, there is a critical need for improved strategies to accurately diagnose IC.

TABLE 1

| Diseases that may mimic symptoms of IC (Wein et al, 1990) |
|---|
| Active genital herpes |
| Vaginitis |
| Bladder stones |
| Bladder cancer |
| Cancer of the uterus, cervix, vagina, or urethra |
| Urethral diverticulum |
| Radiation cystitis |
| Cyclophosphamide cystitis |
| Bladder tuberculosis |
| Neurogenic bladder |
| Drug effects: aspirin, NSAIDs, allopurinol |

Etiology of Interstitial Cystitis: Despite multiple hypotheses about the primary cause of IC, the underlying molecular mechanism of this disease remains completely undefined. Active theories include increased permeability of the bladder mucosa, abnormal neuronal function, mast cell activation, autoimmunity, infections, and toxic or antiproliferative substances in the urine (Erickson et al, 1999); however, insufficient data exist to definitively establish their roles in the pathology of IC. One of the most consistent findings in bladder mucosal biopsies from IC patients has proven to be thinning or erosion of the bladder epithelium (Keay, 2008; Leiby et al, 2007). It is speculated that normal repair of the damaged bladder epithelium does not occur in patients who develop IC; thus, urine contents, such as potassium, can leak into the bladder interstitium, possibly leading to mast cell activation and histamine release. In response, C-fiber nerves become activated, triggering the release of Substance P as well as immunogenic and allergic responses. These events are thought to lead to progressive bladder injury, which may promote spinal cord changes in some patients, causing chronic neuropathic pain (Hanno, 2007). Research studies have demonstrated abnormal cell signaling in IC bladder epithelial cells as compared to controls. The expression of several proteins, including group D-related human leukocyte antigen (HLA-DR) and inter-cellular adhesion molecule 1 ICAM-1, the secreted proteins IL-1, TNFα, and various epithelial growth factors (i.e., HB-EGF, EGF, and IGF1) have been shown to have altered expression in bladder biopsies and/or explanted primary bladder epithelial cells from IC patients (Keay, 2008). In addition, increased paracellular permeability and abnormalities in tight junction protein expression (i.e, zonula occludens-1 [ZO-1], occludin, and claudin 1, 4, and 8) have been demonstrated in explanted bladder epithelial cells grown for IC patient biopsies as compared to cells from normal controls (Zhang et al, 2005; Keay et al, 2003a; Zhang et al, 2007). These abnormalities may be related to altered bladder epithelial cell differentiation in IC patients, with increased E-cadherin expression and decreased expression of ZO-1 and uroplakin III, and altered cytokeratin gene expression in vivo and/or in vitro (Keay et al, 2003a; Zhang et al, 2007; Hauser et al, 2008; Southgate et al, 2007; Slobodov et al, 2004; Laguna et al, 2006; Keay, 2008). Bladder epithelial cells from IC patients also exhibit profoundly decreased proliferation (Keay et al, 2003b), decreased expression of cyclin D1 and JNK (Keay et al, 2003a), and increased paracellular permeability in vitro in the absence of exogenous serum or growth factors as compared to cells from normal controls (Zhang et al, 2005). Collectively, these findings provide additional indirect evidence for altered epithelial cell signaling in IC.

Current Approaches to IC Diagnosis: The diagnosis of IC in the general population is based on the presence of pain related to the bladder, usually accompanied by frequency and urgency to urinate, in the absence of other diseases that could cause the symptoms. Diagnostic tests that help rule out other disease include urinalysis, urine culture, cystoscopy, biopsy of the bladder wall, distention of the bladder under anesthesia, urine cytology, and laboratory examination of prostate secretions (Sant and Hanno, 2001). Multiple urine markers for IC have been described including antiproliferative factor (APF), EGF, IGF binding protein-3, and interleukin (IL)-6, which are significantly increased in IC and HB-EGF, cyclic guanosine monophosphate, and methylhistamine, which are significantly decreased in IC. In a study that compared these markers, APF was found to have the least overlap in the IC and control groups (Erickson et al, 2002). APF was originally purified from the urine of IC patients, and bioactivities attributed to APF include suppression of urothelial cell proliferation; increases in transcellular permeability; lowering of the expression of proteins that form intercellular junctional complexes; and reduction in the production of HB-EGF from urothelial cells (Keay et al, 2004). APF activity is detectable in the urine of approximately 95-97% of IC patients who fulfill the symptomatic, exclusionary, and cystoscopic NIDDK criteria for IC (Keay et al, 2001; Keay et al, 1996) and 94% of patients who fulfill symptomatic and exclusionary criteria alone (Keay et al, 2007). The specificity of APF for urine from IC patients (vs. normal controls or patients with a variety of other urogenital disorders (Keay et al, 2001)) suggests that it is useful as a diagnostic marker for IC.

Potential Role of APF Interstitial Cystitis: APF is a low molecular weight sialoglycopeptide secreted specifically from bladder epithelial cells in patients suffering from IC (Keay et al, 2004; Keay et al, 2000). The peptide sequence of APF is identical to residues 541-549 of the 6th transmembrane domain of Frizzled 8, a Wnt ligand receptor. The glycosyl moiety of APF consists of sialic acid α-2,3 linked to galactose P1-3-N-acetylgalactosamine, which is α-O-linked to the N-terminal threonine residue of the nonapeptide. APF has been shown to profoundly inhibit the proliferation of normal bladder epithelial, bladder carcinoma, and cervical adenocarcinoma cells in vitro (Keay et al, 2004; Keay et al, 2000). Furthermore, APF can induce multiple changes in the pattern of cellular gene expression including decreased production of HB-EGF and increased production of E-cadherin, resulting in a more differentiated bladder epithelial cell phenotype (Keay et al, 2000; Keay et al, 2003). APF was also recently determined to decrease tight junction protein (zonula occludens-1 and occludin) production and increase paracellular permeability of normal bladder epithelial cell monolayers similar to changes seen in cells from patients with IC in vitro (Zhang et al, 2005). This accumulation in urine of a bioactive factor, capable of altering the behavior of urothelial cells, is consistent with the clinical observation of epithelial thinning and denudation observed in IC bladder tissue.

The potency of APF (EC50 in the picomolar range), its varied effects on bladder epithelial cell protein expression and proliferation, and the requirement for a hexosamine-galactose disaccharide linked in a specific alpha configuration to the backbone peptide for activity, all indicate that APF's effects are mediated by binding to and activating a receptor.

In 2006, Conrads et al identified cytoskeletal associated protein 4 (CKAP4) (also known as p63, CLIMP-63, ERGIC-63), as a high affinity receptor for APF (Conrads et al, 2006). CKAP4 has also been identified as a functional cell surface receptor for tissue plasminogen activator (tPA) in smooth muscle cells (Razzaq et al, 2006) and for surfactant protein A (SP-A) in rat type II pneumocytes (Gupta et al, 2006). CKAP4 is a nonglycosylated, reversibly palmitoylated, type II transmembrane protein. At its NH2 terminus, CKAP4 has a 106-amino acid long cytosolic tail, a single transmembrane domain, and a large extracytoplasmic domain of 474 amino acids. Original studies of CKAP4 described it as an endoplasmic reticulum (ER) resident protein (Schweizer et al, 1994). Subsequently, it was shown to aid in the anchoring of rough ER to microtubules in epithelial cells (ie, COS and HeLa) (Klopfenstein et al, 1998). This function requires a direct interaction between the cytoplasmic N-terminal tail of the protein to microtubules and is regulated by phosphorylation (Vedrenne et al, 2005).

A system for detecting APF bioactivity utilizes $^3$H-thymidine incorporation to measure the cellular proliferation of cultured normal bladder epithelial cells (explanted from human bladder tissue) following exposure of the cells to patient urine. This bioassay does not discriminate from other factors present in urine that have also been shown to regulate cellular proliferation (e.g., heparin binding epidermal growth factor-like growth factor (HB-EGF), epidermal growth factor (EGF), interleukin-1 (IL-1) and insulin-like growth factor 1 (IGF1), etc.) A system for detecting APF by generating specific antibodies against this 9 amino acid glycopeptides is problematic. It's size of 9 amino acids indicate it is not a good immunogen as this is the minimal size epitope for any antibody to recognize and well below minimal sized polypeptides used to generate specific antibodies. Further, developing a specific antibody against APF is also problematic given that its 9 amino acids are identical to sequences found in a receptor protein called Frizzled 8, presenting the potential to cross-react with a larger protein that shares this sequence. A second system for detecting APF is the focus of the present invention, includes measuring its presence based on bioactivity, a cell-based system that expresses a specific receptor for APF and upon presentation of urine samples to the cell based system, binding of APF induces translocation of the receptor to the nucleus. The receptor protein is fused to a fluorescent indicator signaling protein. The presence of the fluorescent signal in the nucleus is quantified by high-throughput microscopy. Translocation of the fluorescent signal into the nucleus is diagnostic for the presence of APF and for IC.

In addition, Palmitoylation is the posttranslational addition of the 16-carbon palmitate group to specific cysteine residues of proteins (Smotrys and Linder, 2004) via a labile thioester bond. Unlike other forms of lipidation, such as myristoylation and prenylation, palmitoylation is reversible which allows for dynamic regulation of protein-membrane interactions, trafficking between membrane compartments (Wedegaertner and Bourne, 1994; Jones et al., 1997; Moran et al., 2001; Zacharias et al., 2002), and synaptic plasticity (el-Husseini Ael and Bredt, 2002). For many years it was believed that palmitoylation occurred primarily by autocatalytic mechanisms (Bizzozero et al., 1987; Bano et al., 1998); however, the recent discovery of a family of palmitoyl acyl transferase (PAT) enzymes that catalyze protein palmitoylation has reversed this notion, expanding the complexity of the mechanisms by which palmitoylation is regulated (Lobo et al., 2002; Roth et al., 2002; Fukata et al., 2004; Linder and Deschenes, 2007).

PATs are encoded by the ZDHHC gene family and are characterized by an Asp-His-His-Cys motif (DHHC) within a cysteine-rich domain (CRD). The DHHC and CRD domains are essential for palmitoyl acyl transferase activity (Roth et al., 2002; Fukata et al., 2004; Sharma et al., 2008). Twenty-three genes encoding proteins with DHHC-CRD domains have been identified in mouse and human databases (Fukata et al., 2004). Of these, at least seven have been shown to be associated with human disease: DHHC8 with schizophrenia (Mukai et al., 2004); DHHC 17/HIP 14 with Huntington's disease (Yanai et al., 2006); DHHC15 and DHHC9 with X-linked mental retardation (Mansouri et al., 2005; Raymond et al., 2007); and DHHC2, DHHC9, DHHC17, and DHHC11 with cancer (Oyama et al., 2000; Ducker et al., 2004; Mansilla et al., 2007; Yamamoto et al., 2007). In many of these examples, the absence of PAT expression and subsequent failure to palmitoylate target substrates is the underlying problem.

Although now recognized as a PAT, DHHC2 was previously known as ream for reduced expression associated with metastasis. As the name suggests, this gene was first identified because its expression level was consistently and significantly reduced in clonal murine colorectal adenocarcinoma cell lines with high metastatic potential, but not in clonal lines derived from the same tumor that did not metastasize (Tsuruo et al., 1983; Oyama et al., 2000). It was concluded that ream expression is inversely related to the metastatic potential of a cell, leading to speculation that this gene normally suppresses one or more of the processes by which cancer cells escape from blood vessels, invade into and proliferate in a target organ, and induce angiogenesis and form metastatic foci. Human ZDHHC2 maps to a region of chromosome 8 (p21.3-22) that is frequently deleted in many types of cancer, including colorectal (Fujiwara et al., 1993; Ichii et al., 1993; Fujiwara et al., 1994) hepatocellular carcinoma (Emi et al., 1993; Fujiwara et al., 1994), non-small cell lung (Fujiwara et al., 1993; Ohata et al., 1993), and cancers of the breast (Yaremko et al., 1996; Anbazhagan et al., 1998), urinary bladder (Knowles et al., 1993), and prostate (Bova et al., 1993). Loss of heterozygosity on chromosomal band 8p22 has been shown to be a common event in some epithelial tumors, pointing toward the likelihood that the region harbors potential tumor suppressor genes (Emi et al., 1993; Fujiwara et al., 1993; Ichii et al., 1993; Ohata et al., 1993) Because DHHC2 has no other known signaling properties beyond palmitoylation, knowledge of its target substrates in a cancer cell line could yield significant clues about its role in metastasis and tumor suppression. In previous work, we used a novel, proteomic method called PICA to identify the target substrates of DHHC2 in HeLa cells, a cervical adenocarcinoma cell line. We determined that cytoskeletal associated protein 4 (CKAP4, also known as p63, ERGIC-63, and CLIMP-63) is a principle, physiologically important substrate of DHHC2 (Zhang et al., 2008).

CKAP4 is a reversibly palmitoylated, type II transmembrane protein that has been shown to anchor rough ER to microtubules in epithelial cells (ie, COS and HeLa) (Schweizer et al., 1993a; Schweizer et al., 1993b; Schweizer et al., 1994; Schweizer et al., 1995a; Vedrenne and Hauri, 2006). This function requires a direct interaction between the cytoplasmic N-terminal tail of the protein to microtubules and is regulated by phosphorylation of three critical serine residues (Klopfenstein et al., 1998). More recently, CKAP4 has been identified as a functional cell surface receptor for antiproliferative factor (APF) (Conrads et al., 2006), a low molecular weight, Frizzled-8 protein-related sialoglycopeptide secreted from bladder epithelial cells in patients suffering from the chronic, painful bladder disorder, interstitial cystitis (IC) (Keay et al., 2000; Keay et al., 2004a). APF profoundly inhibits normal bladder epithelial cell growth (Keay et al., 1996; Keay et al., 2000; Keay et al., 2004a). APF also inhibits the proliferation of bladder carcinoma cells and HeLa cells in vitro with an IC50 of ~1 nM (Keay et al., 2004a; Conrads et al., 2006; Keay et al., 2006). Binding of APF to CKAP4 results in inhibition of cellular proliferation and altered transcription of at least 13 genes known to be involved in the regulation of proliferation and tumorigenesis (including E-cadherin, vimentin, cyclin D1, p53 and ZO-1) (Keay et al., 2003; Conrads et al., 2006; Kim et al., 2007).

The present invention is directed to the effects of reduced CKAP4 palmitoylation on APF-mediated signaling by silencing the expression of DHHC2 with targeted siRNA. Our data show that DHHC2-mediated palmitoylation of CKAP4 is a critical event regulating CKAP4 subcellular distribution, APF-stimulated changes in cellular proliferation and gene expression, as well as APF-independent changes in cellular migration.

All references cited herein are incorporated herein by reference in their entireties.

BRIEF SUMMARY OF THE INVENTION

The invention provides a nucleic acid reporter gene construct comprising: (a) a promoter; (b) a nucleic acid sequence selected from the group consisting of a CKAP4 gene, fragments thereof, and variants thereof; and (c) a reporter gene. The invention provides a nucleic acid comprising a reporter gene operatively linked to the gene encoding CKAP4, fragments thereof, and variants thereof. The invention further provides the nucleic acid, wherein the encoded CKAP4, fragment thereof, or variant thereof is capable of binding APF. The invention further provides the nucleic acid, wherein the encoded CKAP4, fragment thereof, or variant thereof is capable of binding APF and is capable of translocation to the nucleus. The invention further provides the nucleic acid, further comprising a protein synthesis termination signal and/or a polyadenylation signal downstream of the reporter gene sequence. The invention further provides the nucleic acid, wherein the reporter gene encodes a fluorescent polypeptide selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof. The invention further provides the nucleic acid, wherein the gene product of the reporter gene is a protein whose enzymatic activity is detectable. The invention further provides the nucleic acid, wherein the gene product is LUC (luciferase), AP (alkaline phosphatase), SEAP (secretory alkaline phosphatase) or CAT (chloramphenicol acetyltransferase). The invention further provides the nucleic acid, wherein the reporter protein is an immunologically detectable protein. The invention further provides the nucleic acid, wherein the reporter protein is a selection marker. The invention further provides the nucleic acid, wherein the vectors further comprises a sequence encoding an affinity tag. The invention further provides the nucleic acid, wherein the affinity tag is selected from the group consisting of a polyhistidine tag, polyarginine tag, glutathione-S-transferase, maltose binding protein, staphylococcal protein A tag, an EE-epitope tag, histidine tag, tag-100, c-myc, E2, V5 epitope tag, a 6-His epitope tag, a c-myc tag, a Flag tag, a GFP tag, a GST tag, a HA tag, a luciferase tag, a Protein C tag, an S-tag, a T7 tag, a thioredoxin tag, a VSV-g tag, His-tag, a Flag-tag, an HA-tag, a myc-tag, and other epitope tag.

The invention provides a nucleic acid comprising: (a) a CKAP4 inducible promoter region; (b) a reporter gene operatively linked to the CKAP4 inducible promoter region. The invention further provides the nucleic acid, wherein the reporter gene encodes a fluorescent polypeptide selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof. The invention further provides the nucleic acid, wherein the gene product of the reporter gene is a protein whose enzymatic activity is detectable. The invention further provides the nucleic acid, wherein the gene product is LUC (luciferase), AP (alkaline phosphatase), SEAP (secretory alkaline phosphatase) or CAT (chloramphenicol acetyltransferase). The invention further provides the nucleic acid, wherein the reporter protein is an immunologically detectable protein. The invention further provides the nucleic acid, wherein the reporter protein is a selection marker.

The invention provides a host cell comprising a reporter gene operatively linked to a nucleic acid sequence selected from the group consisting of a CKAP4 gene, fragments thereof, and variants thereof, wherein the encoded CKAP4, fragment thereof, or variant thereof is capable of binding APF and is capable of translocation to the nucleus. The invention further provides the host cell, wherein the cell is selected from the group consisting of VERO, HeLa, CHO, COS, W138, BHK, HepG2, 3T3, RIN, MDCK, A549, PC12, K562 and 293 cells. The invention provides a host cell line stably transfected with a reporter gene operatively linked to a nucleic acid sequence selected from the group consisting of a CKAP4 gene, fragments thereof, and variants thereof, wherein the encoded CKAP4 gene, fragment thereof, or variant thereof is capable of binding APF and is capable of translocation to the nucleus. The invention further provides the stably transfected host cell, wherein the cell is selected from the group consisting of VERO, HeLa, CHO, COS, W138, BHK, HepG2, 3T3, RIN, MDCK, A549, PC12, K562 and 293 cells. The invention provides a host cell comprising a CKAP4 inducible promoter region and a reporter gene operatively linked to the CKAP4 inducible promoter region. The invention further provides the host cell, wherein the cell is selected from the group consisting of VERO, HeLa, CHO, COS, W138, BHK, HepG2, 3T3, RIN, MDCK, A549, PC12, K562 and 293 cells. The invention provides a stably transfected host cell line comprising a CKAP4 inducible promoter region and a reporter gene operatively linked to the CKAP4 inducible promoter region. The invention further provides the stably transfected host cell, wherein the cell is selected from the group consisting of VERO, HeLa, CHO, COS, W138, BHK, HepG2, 3T3, RIN, MDCK, A549, PC12, K562 and 293 cells.

The invention provides an isolated protein encoded by a nucleic acid construct comprising: (a) a promoter; (b) a nucleic acid sequence selected from the group consisting of a CKAP4 gene, fragments thereof, and variants thereof; and (c) a reporter gene. The invention further provides the protein, further comprising a protein synthesis termination signal and/or a polyadenylation signal downstream of the reporter gene sequence. The invention provides an isolated protein comprising a reporter gene operatively linked to the gene encoding CKAP4, fragments thereof, and variants thereof.

The invention further provides the protein, wherein the reporter gene encodes a fluorescent polypeptide selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof.

The invention provides an isolated protein comprising a reporter gene operatively linked to the gene encoding CKAP4, fragments thereof, and variants thereof. The invention further provides the protein, wherein the reporter gene is selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof. The invention further provides the protein, wherein the gene product of the reporter gene is a protein whose enzymatic activity is detectable. The invention further provides the protein, wherein the gene product is LUC (luciferase), AP (alkaline phosphatase), SEAP (secretory alkaline phosphatase) or CAT (chloramphenicol acetyltransferase). The invention further provides the protein, wherein the reporter protein is an immunologically detectable protein. The invention further provides the protein, wherein the reporter protein is a selection marker. The invention further provides the protein, wherein the encoded CKAP4, fragment thereof, or variant thereof is capable of binding APF. The invention further provides the protein, wherein the encoded CKAP4, fragment thereof, or variant thereof is capable of binding APF and is capable of translocation to the nucleus. The invention further provides the protein, wherein each of the expression vectors further comprises a sequence encoding an affinity tag. The invention further provides the protein, wherein the affinity tag is selected from the group consisting of a polyhistidine tag, polyarginine tag, glutathione-S-transferase, maltose binding protein, staphylococcal protein A tag, an EE-epitope tag, histidine tag, tag-100, c-myc, E2, V5 epitope tag, a 6-His epitope tag, a c-myc tag, a Flag tag, a GFP tag, a GST tag, a HA tag, a luciferase tag, a Protein C tag, an S-tag, a T7 tag, a thioredoxin tag, a VSV-g tag, His-tag, a Flag-tag, an HA-tag, a myc-tag, and other epitope tag.

The invention provides a kit comprising the nucleic acid, and instructions for use. The invention provides a kit comprising the host cell, and instructions for use.

The invention provides a method for diagnosis of IC disease in a patient by detecting the presence of APF in a biological sample comprising: (a) providing a first and a second population of host cells comprising a nucleic acid sequence selected from the group consisting of a CKAP4 gene, fragments thereof, and variants thereof, wherein the encoded CKAP4, fragment thereof, or variant thereof is capable of binding APF and is capable of translocation to the nucleus and a reporter gene; (b) providing a biological sample from a patient; (c) contacting the first host cell population with the biological sample; (d) providing a control sample; (e) contacting the second host cell population with the control sample; (f) isolating nuclei from the first and second host cell populations to provide a first and second nuclei population; (g) measuring reporter gene expression in the first nuclei population; (h) measuring reporter gene expression in the second nuclei population; and (i) assessing the reporter gene expression in the first nuclei population relative to the reporter gene expression in the second nuclei population, wherein detecting an increase in said reporter gene expression in the first nuclei population identifies the presence of APF in the biological sample, thereby indicating IC disease. The invention further provides a method wherein the nucleic acid sequence is integrated into a chromosome of the host cells or maintained episomally.

The invention further provides a method wherein the host cells are a mammalian cell population. The invention further provides a method wherein the mammalian cell population is a human cell population. The invention further provides a method wherein the reporter polypeptide is a fluorescent polypeptide. The invention further provides a method wherein the fluorescent polypeptide is selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof. The invention further provides a method wherein the gene product of the reporter gene is a protein whose enzymatic activity is detectable. The invention further provides a method wherein the gene product is LUC (luciferase), AP (alkaline phosphatase), SEAP (secretory alkaline phosphatase) or CAT (chloramphenicol acetyltransferase). The invention further provides a method wherein the reporter protein is an immunologically detectable protein. The invention further provides a method wherein the reporter protein is a selection marker.

The invention provides a method for diagnosis of IC disease in a patient by detecting the presence of APF in a biological sample comprising: (a) providing a first and a second population of host cells comprising a nucleic acid sequence selected from the group consisting of a CKAP4 gene, fragments thereof, and variants thereof, wherein the encoded CKAP4, fragment thereof, or variant thereof is capable of binding APF and is capable of translocation to the nucleus and a reporter gene; (b) providing a biological sample from a patient; (c) contacting the first host cell population with the biological sample; (d) providing a control sample; (e) contacting the second host cell population with the control sample; (f) isolating nuclei from the first and second host cell populations to provide a first and second nuclei population; (g) measuring reporter gene expression in the first nuclei population; (h) measuring reporter gene expression in the second nuclei population; and (i) contacting the first nuclei population with an antibody that binds the protein encoded by the reporter gene to form a first antibody complex; (j) contacting the second nuclei population with an antibody that binds the protein encoded by the reporter gene to form a second antibody complex; and (k) providing a detection antibody; (l) contacting the detection antibody with the first antibody complex; (m) contacting the detection antibody with the second antibody complex; (n) detecting the presence of the detection antibody that bound to the first and second antibody complex; and (o) assessing the reporter gene expression in the first antibody complex relative to the reporter gene expression in the second antibody complex, wherein detecting an increase in said reporter gene expression in the first antibody complex identifies the presence of APF in the biological sample, thereby indicating IC disease. The invention further provides a method wherein the biological sample is a member selected from the group consisting of whole blood, serum, plasma, cerebrospinal fluid, saliva, urine, spinal fluid, synovial fluid, amniotic fluid and cranial fluid, and lymphocyte or cell culture supernatants.

The invention provides a method for diagnosis of IC disease in a patient by detecting APF protein in a biological sample comprising: (a) providing a first and a second population of host cells comprising a nucleic acid sequence selected from the group consisting of a CKAP4 gene, fragments thereof, and variants thereof, wherein the encoded CKAP4, fragment thereof, or variant thereof is capable of binding APF and is capable of translocation to the nucleus and a reporter gene; (b) providing a biological sample from a patient; (c) contacting the first host cell population with the biological sample; (d) providing a control sample; (e) contacting the second host cell population with the control sample; (f) isolating nuclei from the first and second host cell populations to provide a first and second nuclei population; (g) measuring reporter gene expression in the first nuclei population; (h) measuring reporter gene expression in the second nuclei population; and (i) contacting the first nuclei population with an antibody that binds the protein encoded by the reporter gene to form a first antibody complex; (j) contacting the second nuclei population with an antibody that binds the protein encoded by the reporter gene to form a second antibody complex; and (k) providing a detection antibody to the first antibody complex; (l) providing a detection antibody to the second antibody complex; (m) performing gel electrophoresis on the first antibody complex; (n) performing gel electrophoresis on the second antibody complex; (o) detecting the presence of the detection antibody that bound to the first and second antibody complex; and (p) assessing the reporter gene expression in the first nuclei population relative to the reporter gene expression in the second nuclei population, wherein detecting an increase in said reporter gene expression in the first nuclei population identifies the presence of APF in the biological sample, thereby indicating IC disease.

The invention provides an isolated antibody or fragment thereof which specifically binds a polypeptide selected from the group consisting of CKAP4 gene, fragments thereof, and variants thereof. The invention further provides an antibody or fragment thereof wherein said polypeptide is glycosylated. The invention further provides an antibody or fragment thereof which is polyclonal. The invention further provides an antibody or fragment thereof which is selected from the group consisting of a) a chimeric antibody; b) a Fab fragment; and c) a F(ab)2 fragment. The invention further provides an antibody or fragment thereof which is labeled. The invention further provides an antibody or fragment thereof wherein the label is selected from the group consisting of: a) an enzyme; b) a fluorescent label; and c) a radioisotope; d) and epitope tag. The invention further provides an antibody or fragment thereof which specifically binds to said polypeptide in a Western blot. The invention further provides an antibody or fragment thereof wherein the epitope tag is selected from the group consisting of a polyhistidine tag, polyarginine tag, glutathione-S-transferase, maltose binding protein, staphylococcal protein A tag, an EE-epitope tag, histidine tag, tag-100, c-myc, E2, V5 epitope tag, a 6-His epitope tag, a c-myc tag, a Flag tag, a GFP tag, a GST tag, a HA tag, a luciferase tag, a Protein C tag, an S-tag, a T7 tag, a thioredoxin tag, a VSV-g tag, His-tag, a Flag-tag, an HA-tag, a myc-tag, and other epitope tag. The invention further provides an antibody or fragment thereof which specifically binds to said polypeptide in an ELISA. The invention further provides an antibody or fragment thereof which specifically binds to said polypeptide in a competitive-binding assay. The invention further provides an antibody or fragment thereof which specifically binds to said polypeptide in a radioimmunoassay. The invention provides a n isolated cell that produces the antibody or fragment thereof. The invention provides a hybridoma that produces the antibody of fragment thereof.

The invention provides a method for diagnosis of IC disease in a patient by detecting the presence of APF in a biological sample comprising: (a) providing a detectably labeled first CKAP4 protein, fragments thereof, and variants thereof, wherein the CKAP4 protein is capable of binding APF; (b) providing a detectably labeled second CKAP4 protein, fragments thereof, and variants thereof, wherein the CKAP4 protein is capable of binding APF; (c) providing a biological sample from a patient; (d) contacting the detectably labeled first CKAP4 protein with the biological sample to provide a first test sample; (e) providing a control sample; (f) contacting the detectably labeled second CKAP4 protein with the control sample to provide a second test sample; (g) measuring the label in the first test sample; (h) measuring the label in the second test sample; and (i) assessing the label in the first test sample relative to the label in the second test sample, wherein detecting an increase in the first test sample identifies the presence of APF in the biological sample, thereby indicating IC disease. The invention further provides a method wherein the method of measurement is selected from the group consisting of fluorescence resonance electron transfer (FRET), lanthamide resonance electron transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes. The invention further provides a method wherein the method of measurement is generated/detected following APF binding due to a change in the conformation of the receptor, a change in protein-protein interactions, a change in membrane-protein interactions or other. The other interacting partners being labeled with an appropriate fluorophore to serve as a resonance energy donor or acceptor that appropriately complements the donor or acceptor fluorophore that is attached to CKAP4.

The invention further provides a method wherein the signals from FRET, BRET, LRET and LET may be detected either intramolecularly, where the donor and acceptor fluorophore are part of the same sensor molecule (e.g., CKAP4) or intermolecularly where the donor and acceptor are physically associated with two separate molecules, on of which may be CKAP4, the other any molecule that interacts with CKAP4 in an APF-dependent manner.

The invention provides a method of detecting an agent that binds and/or modulates the activity of CKAP4, the method comprising: (a) contacting a CKAP4 protein, fragments thereof, and variants thereof, wherein the CKAP4 protein is capable of binding APF, with an APF protein, fragments thereof, and variants thereof in the presence of a candidate agent under conditions, which in the absence of the test agent, permit the binding of the APF polypeptide to the CKAP4 polypeptide; and (b) determining whether the candidate agent is capable of modulating the interaction between the CKAP4 polypeptide and the APF polypeptide.

The invention further provides a method wherein the APF polypeptide is a polypeptide comprising: (a) the sequence of APF; or (b) a sequence which is at least 70% identical to APF and which binds to and activates a signaling activity of CKAP4; or is a fragment of APF which binds to and activates a signaling activity of CKAP4. The invention further provides a method wherein the CKAP4 polypeptide is a polypeptide comprising: (a) the sequence of CKAP4; (b) a sequence which is at least 70% identical to CKAP4 over its entire length and functionally equivalent to CKAP4; or (c) a fragment of CKAP4 which is functionally equivalent to CKAP4. The invention further provides a method wherein the candidate agent is a polypeptide, an antibody or antigen-binding fragment thereof, a lipid, a carbohydrate, a nucleic acid, a small molecule, or a chemical compound. The invention further provides a method wherein step (b) comprises monitoring binding of the CKAP4 polypeptide to the APF polypeptide. The invention further provides a method wherein the binding of the CKAP4 polypeptide to the APF polypeptide is monitored using label displacement, surface plasmon resonance, fluorescence resonance energy transfer, fluorescence quenching or fluorescence polarization. The invention further provides a method wherein the APF polypeptide is detectably labelled. The invention further provides a method wherein the APF polypeptide is detectably labelled with a moiety is a radioisotope, a fluorophore, a quencher of fluorescence, an enzyme, an affinity tag or an epitope tag. The invention further provides a method wherein step (b) comprises monitoring the signaling activity of the CKAP4 polypeptide. The invention further provides a method wherein the signaling activity is monitored by measurement of guanosine nucleotide binding, GTPase activity, adenylate cyclase activity, cyclic adenosine monophosphate (cAMP), Protein Kinase C activity, phosphatidylinositol breakdown, diacylglycerol, inositol triphosphate, intracellular calcium, MAP kinase activity or reporter gene expression. The invention further provides a method wherein step (b) comprises monitoring the translocation activity of the CKAP4 polypeptide. The invention further provides a method wherein the CKAP4 polypeptide is expressed on a cell. The invention further provides a method wherein the cell is a mammalian cell.

The invention provides a method for assessing activity of a candidate compound in interfering with binding of an APF protein with a CKAP4 protein expressed in a eukaryotic cytoplasmic and/or cell membrane, comprising: assessing, in the presence and absence of a candidate compound, binding of a polypeptide comprising an APF protein with a CKAP4 protein expressed in a eukaryotic cytoplasmic and/or cell membrane; wherein reduced binding in the presence of the candidate compound relative to a level of binding in the absence of the candidate compound indicates activity of the candidate compound in interfering with binding of APF protein to the CKAP4 protein expressed in a eukaryotic cytoplasmic and/or cell membrane. The invention further provides a method wherein the assessing is performed extracellularly. The invention further provides a method wherein the assessing is performed in intact cells. The invention further provides a method wherein the cell membranes are a cytoplasmic and/or cell membrane preparation, and wherein said assessing comprises determining the binding of the APF to the cell membrane preparation in the presence of a candidate compound and in the absence of a candidate compound, wherein a decrease in the binding of the APF to the cell membrane preparation in the presence of the compound as compared to binding in the absence of the compound identifies the compound as interfering with binding of the APF to the cytoplasmic and/or cell membranes of the eukaryotic cell. The invention further provides a method wherein the method is performed intracellularly in a eukaryotic cytoplasmic and/or cell. The invention further provides a method wherein the APF is coupled to a detectable label and the intracellular distribution of the label is assessed in the presence of a candidate compound, wherein the candidate compound is identified as interfering with binding of the HCV nonstructural protein to a eukaryotic cytoplasmic and/or cell membrane when its presence results in an intracellular distribution of the label which does not show binding to cytoplasmic and/or cell membranes in comparison to the distribution of the label in the absence of the compound. The invention further provides a method wherein the detectable label is green fluorescent protein. The invention further provides a method wherein the eukaryotic cell is a mammalian cell. The invention further provides a method wherein the non-structural protein is NS4B. The invention further provides a method wherein the non-structural protein is NS 5A. The invention further provides a method wherein the candidate compound is a peptide. The invention further provides a method wherein the candidate compound is a modified version of APF that binds to CKAP4 but does not activate the receptor. The invention further provides a method wherein the candidate compound is a modified version of endogenous APF. The invention further provides a method wherein the candidate compound is a difference in the sugar moiety that modifies the N-terminus of APF. The invention further provides a method wherein the candidate compound is or the addition of a modified C-terminus of APF.

The invention provides a method of identifying a peptide that inhibits the binding of an APF to CKAP4 peptide expressed in a cytoplasmic and/or cell membrane of a eukaryotic cell, comprising contacting a polypeptide comprising an APF protein with CKAP4 peptide expressed in cytoplasmic and/or cell membranes of a eukaryotic cell in the presence and absence of a test peptide; and assessing binding of the APF of the polypeptide to the cytoplasmic and/or cell membranes; wherein a decreased level of binding of the APF to the cytoplasmic and/or cell membrane in the presence of the test peptide as compared to a level of binding of the APF to the CKAP4 expressed in cytoplasmic membrane in the absence of the test peptide indicates the test peptide inhibits the binding of an APF to CKAP4 expressed in a cytoplasmic and/or cell membrane of a eukaryotic cell. The invention further provides a method wherein the peptide is a variant of APF. The invention further provides a method wherein the eukaryotic cell is a mammalian cell. The invention further provides a method wherein the polypeptide comprises a detectable label. The invention further provides a method wherein the detectable label is a fluorescent label or a radioisotope. The invention further provides a method wherein the fluorescent label is a green fluorescent protein.

The invention provides a method for diagnosis of IC disease in a patient by detecting the presence of APF in a biological sample comprising: (a) providing a detectably labeled first CKAP4 protein, fragments thereof, and variants thereof, wherein the CKAP4 protein is capable of binding APF; (b) providing a detectably labeled second CKAP4 protein, fragments thereof, and variants thereof, wherein the CKAP4 protein is capable of binding APF; (c) providing an isosteric agent which binds CKAP4; (d) contacting the isosteric agent to the first CKAP4 protein to provide a first CKAP4/agent sample; (e) contacting the isosteric agent to the second CKAP4 protein to provide a second CKAP4/agent sample; (f) providing a biological sample from a patient; (g) contacting the detectably labeled first CKAP4/agent sample with the biological sample to provide a first test sample; (h) providing a control sample; (i) contacting the detectably labeled second CKAP4/agent sample with the biological sample to provide a second test sample; (j) measuring the label in the first test sample; (k) measuring the label in the second test sample; and (l) assessing the label in the first test sample relative to the label in the second test sample, wherein detecting an increase in the first test sample identifies the presence of APF in the biological sample, thereby indicating IC disease.

The invention provides a method to detect CKAP4/APF endocytosis/endocytic vesicles comprising: (a) providing a first and a second population of host cells comprising a nucleic acid sequence selected from the group consisting of a CKAP4 gene, fragments thereof, and variants thereof, wherein the encoded CKAP4, fragment thereof, or variant thereof is capable of binding APF and is capable of translocation to the nucleus and a reporter gene; (b) providing a biological sample from a patient; (c) contacting the first host cell population with the biological sample; (d) providing a control sample; (e) contacting the second host cell population with the control sample; (f) isolating vesicles from the host cells to provide a first and second vesicle population; (g) detecting the presence of the reporter gene in the first and second vesicle populations; and (h) assessing the reporter gene expression in the first vesicle population relative to the second vesicle population, wherein detecting an increase in said reporter gene expression in the first vesicle population identifies the presence of APF in the biological sample, thereby indicating IC disease. The invention further provides a method wherein the nucleic acid sequence is integrated into a chromosome of said population of cells or maintained episomally. The invention further provides a method wherein the population of cells is a mammalian cell population. The invention further provides a method wherein the mammalian cell population is a human cell population. The invention further provides a method wherein the reporter polypeptide is a fluorescent polypeptide. The invention further provides a method wherein the fluorescent polypeptide is selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof. The invention further provides a method wherein the gene product of the reporter gene is a protein whose enzymatic activity is detectable. The invention further provides a method wherein the gene product is LUC (luciferase), AP (alkaline phosphatase), SEAP (secretory alkaline phosphatase) or CAT (chloramphenicol acetyltransferase). The invention further provides a method wherein the reporter protein is an immunologically detectable protein.

The invention provides a method of detecting a APF protein in a biological sample comprising: (a) providing a first and a second population of host cells comprising a nucleic acid sequence selected from the group consisting of a CKAP4 gene, fragments thereof, and variants thereof, wherein the encoded CKAP4 is capable of binding APF and is capable of translocation to the nucleus and a reporter gene; (b) providing a biological sample from a patient; (c) contacting the first host cell population with the biological sample; (d) providing a control sample; (e) contacting the second host cell population with the control sample; (f) isolating nuclei from the first and second host cell populations to provide a first and second nuclei population; (g) measuring reporter gene expression in the first nuclei population; (h) measuring reporter gene expression in the second nuclei population; and (i) contacting the first nuclei population with an antibody that binds the protein encoded by the reporter gene to form a first antibody complex; (j) contacting the second nuclei population with an antibody that binds the protein encoded by the reporter gene to form a second antibody complex; and (k) providing a detection antibody to the first antibody complex; (l) providing a detection antibody to the second antibody complex; (n) detecting the presence of the detection antibody that bound to the first and second antibody complex; and (o) assessing the reporter gene expression in the first nuclei population relative to the reporter gene expression in the second nuclei population, wherein detecting an increase in said reporter gene expression in the first nuclei population identifies the presence of APF in the biological sample, thereby indicating IC disease.

The invention provides a method to measure APF in a biological sample comprising: (a) providing a first reporter vector comprising a promoter region, wherein the promoter region is responsive to CKAP4/APF binding, a nucleic acid sequence selected from the group consisting of a CKAP4 gene, fragments thereof, and variants thereof, and a reporter gene and CKAP4 protein, fragments thereof, or variants thereof to provide a first assay sample; (b) providing a second reporter vector comprising a promoter region, wherein the promoter region is responsive to CKAP4/APF binding, a nucleic acid sequence selected from the group consisting of a CKAP4 gene, fragments thereof, and variants thereof, and a reporter gene and CKAP4 protein, fragments thereof, or variants thereof to provide a second assay sample; (c) providing a biological sample; (d) contacting the first assay sample with the biological sample to provide a first test sample; (e) providing a control sample; (f) contacting the second assay sample with the control sample to provide a second test sample; (g) measuring reporter gene activity in the first test sample; (h) measuring reporter gene activity in the second test sample; and (i) comparing reporter gene activity in the first test sample compared to the second test sample, wherein detecting an increase in said reporter gene expression in the first test sample identifies the presence of APF in the biological sample. The invention further provides a method wherein the reporter polypeptide is a fluorescent polypeptide. The invention further provides a method wherein the fluorescent polypeptide is selected from the group consisting of a green fluorescent protein (GFP), an enhanced GFP (EGFP), a destabilized enhanced GFP (d2EGFP), a blue fluorescent protein (BFP), a cyan fluorescent protein (CFP) a yellow fluorescent protein (YFP), or a red fluorescent protein (RFP including DsRed), a fluorescent protein of any spectral characteristics from any organism, a fluorescent protein that is a monomer, and a fluorescent protein that is a fused dimer, and combinations thereof. The invention further provides a method wherein the gene product of the reporter gene is a protein whose enzymatic activity is detectable. The invention further provides a method wherein the gene product is LUC (luciferase), AP (alkaline phosphatase), SEAP (secretory alkaline phosphatase) or CAT (chloramphenicol acetyltransferase). The invention further provides a method wherein the reporter protein is an immunologically detectable protein.

The invention provides a kit for detecting interstitial cystitis in a patient, by detecting the presence of APF in a biological sample comprising said kit comprising: (a) at least one detection reagent which is specific for APF present in a fluid sample collected from the patient suspected of having the interstitial cystitis, wherein said at least one detection reagent is adapted to detect a threshold level of said APF, said threshold level adapted to indicate a presence of interstitial cystitis; and (b) instructions for using said at least one detection reagent to evaluate interstitial cystitis in the patient. The invention further provides a kit wherein the fluid sample is urine. The invention further provides a kit wherein a detection reagent is selected from the group consisting of antigens; haptens; monoclonal and polyclonal antibodies; natural and synthetic mono-, oligo- and polysaccharides; lectins; avidin and streptavidin; biotin; growth factors; hormones; receptor molecules; and combinations thereof. The invention further provides a kit wherein the detection reagent is selected from monoclonal and polyclonal antibodies. The invention further provides a kit wherein the detection reagent comprises an antibody or antibody fragment. The invention further provides a kit wherein the detection reagent comprises CKAP4 protein, fragments thereof, and variants thereof, wherein the CKAP4 protein is capable of binding APF. The invention further provides a kit wherein said kit comprises a detector device having a support in communication with at least one of said at least three detection reagents. The invention further provides a kit wherein said kit comprises a dipstick, a swab, and a container. The invention further provides a kit wherein the detection reagents are attached to a detectable label. The invention further provides a kit further comprising one or both of a positive and a negative control.

The invention provides a method of screening for interstitial cystitis in a patient, said method comprising the steps of: (a) obtaining a fluid sample from a patient; (b) applying the sample to a detector device, wherein the detector device comprises at least one detection reagent which is specific for APF, wherein said at least one detection reagent is adapted to detect a threshold level of APF, said threshold level correlated with a presence of interstitial cystitis; (c) ascertaining the threshold level of APF present in said sample, wherein if the concentration each of said APF exceeds the threshold level, then this is a positive screen for interstitial cystitis. The invention further provides a method wherein the fluid sample is urine. The invention further provides a method wherein said ascertaining is performed by an enzyme-linked immunosorbent assay. The invention further provides a method wherein the detection reagent is selected from the group of species consisting of antigens; haptens; monoclonal and polyclonal antibodies; natural and synthetic mono-, oligo- and polysaccharides; lectins: avidin and streptavidin; biotin; growth factors; hormones; receptor molecules; and combinations thereof. The invention further provides a method wherein the detection reagent is selected from monoclonal and polyclonal antibodies. The invention further provides a method wherein said reagents comprise an antibody or antibody fragment. The invention further provides a method wherein the detection reagent comprises CKAP4 protein, fragments thereof, and variants thereof, wherein the CKAP4 protein is capable of binding APF. The invention further provides a method wherein said detector device is a dipstick comprising at least one detection reagent which is specific for APF.

BRIEF DESCRIPTION OF SEVERAL VIEWS OF THE DRAWINGS

FIG. 1 is a diagram showing the cloning strategy of creating CKAP4-YFP. To monitor visually, by fluorescence microscopy, the subcellular distribution of CKAP4, wild-type CKAP4 was fused to the C-terminus of monomeric yellow fluorescent protein (CKAP4-YFP). The plasmid pCDNA3.1 is used for subcloning. Here, CKAP4 is subcloned in frame with YFP sequences which exist at the 3' end of the multiple cloning site. This results in a coding sequence that can direct expression of CKAP4-YFP fusion protein. Transcription of this gene in cells is driven by the strong promoter sequence, CMV.

FIG. 2 shows HeLa cells expressing CKAP4-YFP in the absence and presence of synthetic APF (Peptides International, Louiville Ky.). In HeLa cells transiently transfected with the CKAP4-YFP construct, CKAP4-YFP localization was observed on the plasma and perinuclear membranes similar to endogenous CKAP4 expression (Zhang et al, 2008; Planey et al, 2008). The application of synthetic APF to these transiently transfected cells promotes rapid nuclear localization of CKAP4:YFP.

FIG. 3 shows endogenous CKAP4 localization in the presence and absence of APF, which is consistent with the appearance of CKAP4-YFP expressed in HeLa cells (Conrads et al, 2006; Razzaq et al, 2006; Zhang et al, 2008; Planey et al, 2008; Gupta et al, 2006; Bates et al, 2008).

FIG. 4 confirms the results of FIG. 2 and FIG. 3 using a biochemical approach where the nuclear fraction of a cell is separated from the cytoskeletal fraction. The proteins associated with each fraction are resolved by SDS polyacrylamide gel electrophoresis (SDS-PAGE), proteins transferred to nitrocellulose by western transfer and the nitrocellulose probed with anti-CKAP4 antibodies using western blot analysis. CKAP4 abundance is increased in nuclear fractions from APF treated HeLa cells. Application of synthetic APF to these cells resulted in a 5-fold increase in the abundance of CKAP4 in the nucleus versus untreated cells.

FIG. 5 is a depiction of cells expressing CKAP4-YFP (panel A). Urine samples from patients displaying symptoms consistent with IC are added to the cells (panel B). If APF is present in the patient urine sample, CKAP4-YFP moves to the nucleus (panel C) while, patient samples that do not have APF will reveal CKAP4-YFP at the cell membrane (panel D).

FIG. 6 shows the half-life of DHHC2 mRNA. (6A) The abundance of DHHC2 mRNA after siRNA-mediated DHHC2 knockdown was measured by qRT-PCR at 0, 12, 24, 48, 72 and 96 hours following siRNA oligo transfection. These experiments were run in triplicate. The data were approximated most accurately using a non-linear, first-order exponential decay. The half life was calculated to be 13.87 hours ($R2=0.998$, n=3 error bars=SE). (6B) The relative abundance of DHHC2 mRNA in siRNA-transfected cells versus mock transfected control cells was determined after 96 hours by qRT-PCR. DHHC2 expression was reduced ~84% with siRNA knockdown. (6C) CKAP4 interacts with CFP-DHHC2. CFP-tagged DHHC2 was immunoprecipitated from transiently-transfected HeLa cells using an anti-GFP mAb (see Materials and Methods). Western blot analysis with an anti-CKAP4 antibody detected a robust band at ~63 kDa characteristic of CKAP4 in lysates from cells transfected with CFP-DHHC2 but not in lysates from mock transfected cells. Exposure time was 15 seconds.

FIG. 9 shows the siRNA-mediated knockdown of DHHC2 blocks the antiproliferative response of HeLa and NB cells to APF. (9A) HeLa cells were electroporated with DHHC2 double-stranded siRNA (solid circles) or with nonsense siRNA (open circles) as a control for nonsequence-specific effects on Day 1, serum-starved on Day 2, and varying concentrations of APF or control peptide (0.25-250 nM) were added to the medium on Day 3; cells were then cultured for an additional 48 hours under conditions of serum starvation. (9B) NB epithelial cells were electroporated with DHHC2 double-stranded siRNA (solid circles) or with nonsense siRNA (solid triangles) as a control for nonsequence-specific effects on Day 1, serum-starved on Day 2, and varying concentrations of APF or control peptide (0.25-250 nM) were added to the medium on Day 3; cells were then cultured for an additional 48 hours under conditions of serum starvation. For both cell types, cellular proliferation was assessed by inhibition of 3H-thymidine incorporation. Each data point represents the mean and standard deviation of three independent experiments. Data are presented as percent inhibition of 3H-thymidine incorporation compared to controls. The ability of APF to block proliferation was inhibited in the presence of DHHC2 siRNA for all APF concentrations except 250 nM for HeLa cells, or 25 and 250 nM for NB cells.

FIG. 10 shows APF-mediated changes in gene expression are dependent on palmitoylation of CKAP4 by DHHC2 in NB cells. Primary NB epithelial cells were electroporated with DHHC2 double-stranded siRNA or with nonsense siRNA on Day 1, serum-starved on Day 2, and 2.5 nM APF or control peptide were added to the medium on Day 3; cells were then cultured for an additional 48 hours under conditions of serum starvation. Expression of ZO-1, vimentin, and E-cadherin mRNA was assessed by quantitative real-time PCR as described in the Experimental Procedures. (10A, 10B) APF alone or in the presence of nonsense siRNA reduced ZO-1 and vimentin mRNA levels by ~93% and ~97%, respectively. DHHC2 knockdown blocked this APF-stimulated reduction in ZO-1 and vimentin mRNA levels. (10C) APF alone or in the presence of nonsense siRNA dramatically increased E-cadherin mRNA levels, an effect that was also blocked by DHHC2 knockdown. ZO-1, vimentin, and E-cadherin mRNA levels were measured in triplicate runs and quantified by normalization to mRNA levels for β-actin using real-time PCR analysis software from Applied Biosystems. The error in the normalized, relative abundance of each mRNA species was propagated forward from the standard deviation of the mean Ct value for each of the experimental samples and the actin control.

FIG. 11 shows the APF-mediated changes in protein expression are dependent on palmitoylation of CKAP4 by DHHC2 in NB cells. Primary NB epithelial cells were transfected with DHHC2 double-stranded siRNA on Day 1, serum-starved on Day 2, and 2.5 nM APF or control peptide were added to the medium on Day 3; cells were then cultured for an additional 48 hours under conditions of serum starvation. FIG. 11A—ZO-1 and vimentin protein expression was analyzed by SDS-PAGE followed by Western blotting with antibodies to ZO-1 (220 kDa) and vimentin (57 kDa) as described in Experimental Procedures. To assess equal loading of protein, membranes were stripped and reprobed with a mAb to β-actin (1:5000; Sigma). Proteins were visualized by enhanced chemiluminescence and subsequent exposure to film (BioMaxAR, Kodak). FIG. 11B—The signal intensities for ZO-1 was quantified by densitometry using ImageJ, normalized to the corresponding band for β-actin, and reported as the fractional abundance of the control (mock-transfected cells). FIG. 11C—The signal intensities for vimentin were quantified by densitometry using ImageJ, normalized to the corresponding band for β-actin, and reported as the fractional abundance of the control (mock-transfected cells). Results shown are representative of three independent experiments that gave similar results.

FIG. 12 shows the APF-mediated changes in vimentin protein expression are dependent on palmitoylation of CKAP4 by DHHC2 in HeLa cells. HeLa cells were transfected with DHHC2 double-stranded siRNA, nonsense siRNA, or mock-transfected and cultured for 48 hours. Cells were then serum-starved, and the indicated cultures incubated with APF (20 nM) for an additional 48 hours. (12A) Expression of vimentin protein was analyzed by SDS-PAGE and Western blotting with a mAb antibody against vimentin (57 kDa) as described in Experimental Procedures. To assess equal loading of protein, membranes were stripped and reprobed with a mAb to β-actin (1:5000; Sigma). Proteins were visualized by enhanced chemiluminescence and subsequent exposure to film (BioMaxAR, Kodak). (12B) The signal intensity for vimentin was quantified by densitometry using ImageJ, normalized to the corresponding band for β-actin, and reported as the fractional abundance of the control (mock-transfected cells). Results shown are representative of three independent experiments that gave similar results.

FIG. 13 shows the Stable CKAP4 C100S expression increases the migratory rate of HeLa cells. HeLa cells stably transfected with CKAP4 C100S, WT CKAP4, or parental controls were seeded in fibronectin coated, 6-well plates and grown to confluence. To permit measurement of migration in the absence of proliferation, cells were treated with AraC (5 µg/ml; Sigma), blocking further cell division. After 8 hours in AraC, a line of adherent cells was scraped from the bottom of each well with a p-200 pipette tip to generate a "wound." (13A) Cells were allowed to migrate into the wound for 24 hours, and the extent of migration into the region from which cells had been scraped was determined from consecutive images of the same field of view taken at 3-hour intervals. Cells were photographed using a Nikon Eclipse TE2000-U microscope under 20× magnification and phase contrast. (13B) The cell-free area introduced by each wound was measured using ImageJ and converted to a percentage of area at time 0 plotted against time. These data were fit to a monoexponential decay curve (Microcal Origin, Northampton Mass.). The T½ rate for migration of cells into the wound was calculated to be 2.3 hours for CKAP4 C100S cells (red, open circles) and 5.7 hours for WT CKAP4 cells (green squares); parental HeLa cells did not migrate into the wound during the course of these experiments (horizontal blue diamonds across the top of the graph).

FIG. 15 shows multiple alignment of CKAP4 proteins that result from alternative splicing. FIGS. 15A, 15B, and 15C show (SEQ ID NO: 11), (SEQ ID NO: 12), (SEQ ID NO: 13), (SEQ ID NO: 17), (SEQ ID NO: 18), (SEQ ID NO: 19).

FIG. 16 shows multiple sequence alignment of CKAP4 and variants. FIGS. 16A, 16B, 16C, 16D, and 16E show (SEQ ID NO: 14), (SEQ ID NO: 15), (SEQ ID NO: 16), (SEQ ID NO: 20), (SEQ ID NO: 21), (SEQ ID NO: 22).

FIG. 17 shows the detailed intron/exon structure of the gene encoding CKAP4. FIG. 17A shows the structure of Homo sapiens chromosome 12 at 12q23.3 and the splice variants and expressed sequence tags (ESTs) known to exist. FIG. 17B shows the gene summary for CKAP4. The gene is comprised of multiple exons. Alternative splicing of these exons may produce unique proteins that retain their ability to bind to and transduce the known effects of APF.

FIG. 18 shows the expression analyses of CKAP4 in a broad array of tissues and disease states. FIG. 18A—GeneNote Expression array images. FIG. 18B—GNF Normal Expression array images. FIG. 18C—GNF Cancer Expression array images. Experimental tissue vectors: Duplicate measurements were obtained for twelve normal human tissues (out of 28 tissues shown) hybridized against Affymetrix GeneChips HG-U95A-E (GeneNote data) and for 22 normal human tissues hybridized against HG-U133A (GNF Symatlas data **). The intensity values (shown on the y-axis) were first averaged between duplicates, then probeset values were averaged per gene, global median-normalized and scaled to have the same median of about 70 (half-way between GeneNOte and GNF medians). Available at GNF Symatlas, HG-U133A expression data for 18 NCI60 cancer cell lines was processed and added to the display (a single measurement taken; normalized according to the GNF Symatlas normal data).

FIG. 19 shows orthologs of the human CKAP4 gene. The table presents the following columns:

Organism—The names of the homologous species, using both scientific and popular terminology.

Gene—The symbol for the gene in the homologous species.

Locus—The position of the gene in the homologous species.

Description—Its description.

Human Similarity—The percent similarity to the human gene, followed either by (n) where the comparison was based on nucleic acids or (a) for amino acid based comparisons.

Figure 7:
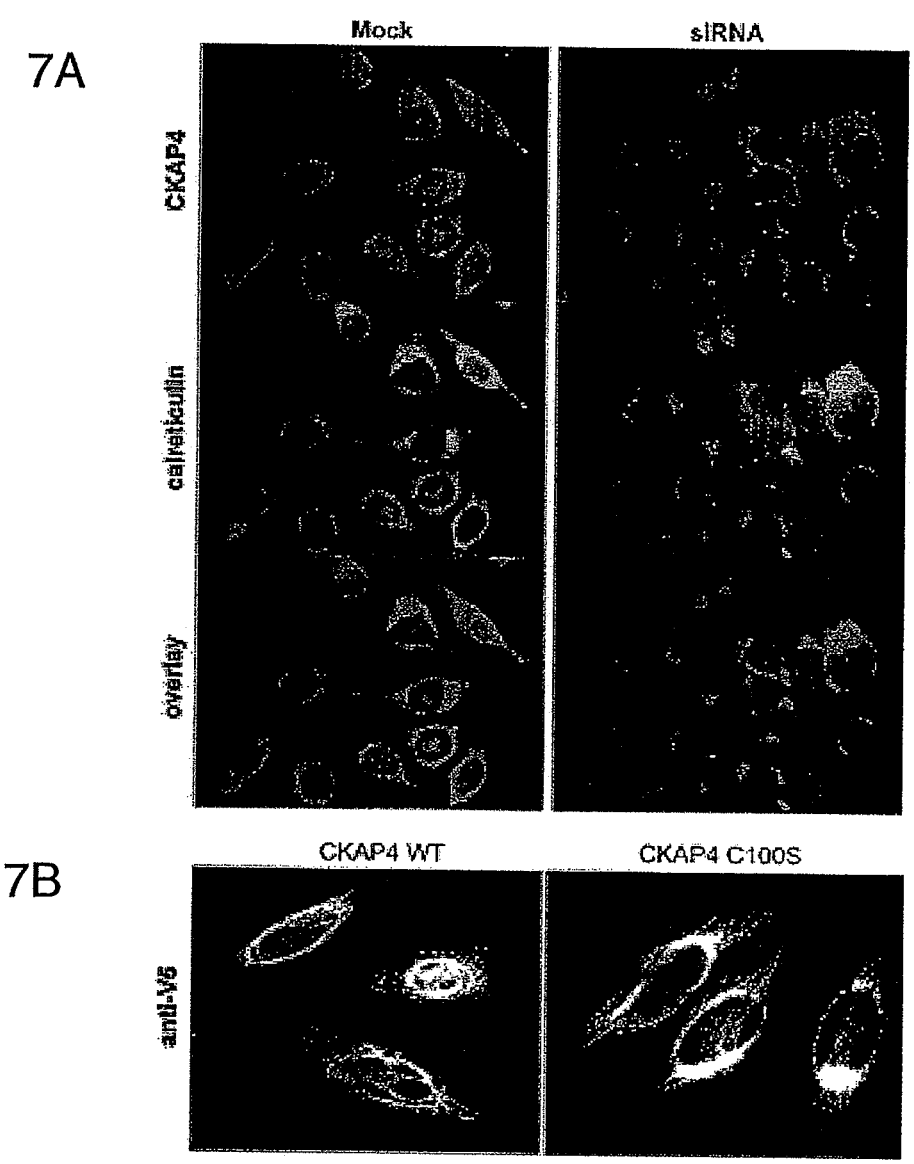
FIG. 7 shows that the DHHC2-mediated palmitoylation of CKAP4 on cysteine 100 regulates its trafficking from the ER to the PM. (7A) Mock-transfected or ZDHHC2 siRNA-transfected HeLa cells were grown on LabTek multiwell glass slides (Nalge Nunc), fixed, and incubated with a mAb G1/296 against CKAP4 ("anti-CLIMP-63", diluted 1:100, Alexis Biochemicals) followed by a TRITC-labeled, goat anti-mouse secondary antibody (diluted 1:1000, Jackson ImmunoResearch Laboratories) or with a pAb against calreticulin (diluted 1:1000, Abcam) followed by a FITC-labeled, goat anti-rabbit secondary antibody (diluted 1:1000, Invitrogen). Controls included cells processed without primary and/or secondary antibodies. Images were acquired using a Nikon TE2000 epifluorescence microscope with MS Elements Software and overlayed using Adobe Photoshop software. In HeLa cells with reduced DHHC2 expression, CKAP4 localization is restricted to the ER (white arrows). (7B) HeLa cell lines stably expressing CKAP4 WT-V5 or the palmitoylation-incompetent mutant, CKAP4 C100S-V5, were grown on LabTek multiwell glass slides (Nalge Nunc), fixed, and immunolabeled with a FITC-conjugated mAb antibody against the V5 epitope (1:500; Invitrogen). CKAP4 WT was expressed on the plasma membrane and perinuclear membranes, whereas CKAP4 C100S expression was restricted to the ER. Epifluorescence images in 7B were made with a 100X, 1.45 NA oil immersion objective (Nikon).
Figure 8:
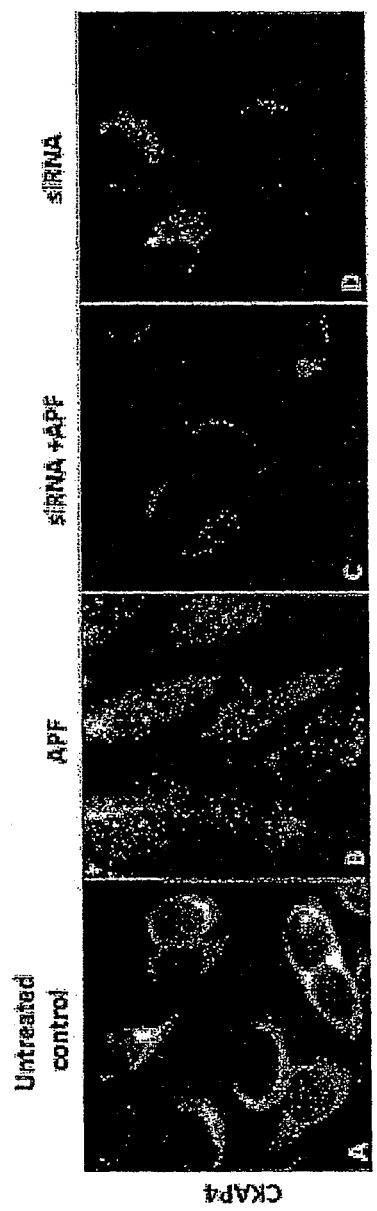
FIG. 8 shows that the palmitoylation of CKAP4 by DHHC2 is required for APF-stimulated translocation of CKAP4 to the nucleus. Mock-transfected or DHHC2 siRNA-transfected HeLa cells were treated with APF (20nM) for 48 hours. Cells were fixed and incubated with a mAb G1/296 against CKAP4 ("anti-CLIMP-63", Alexis Biochemicals) followed by a TRITC-labeled, goat anti-mouse secondary antibody (Jackson ImmunoResearch Laboratories). CKAP4 translocated to the nucleus and nucleolus in HeLa cells treated with APF (red arrows); however, this translocation was blocked in APF-treated HeLa cells transfected with DHHC2 siRNA. Epifluorescence images were made with a 60X 1.45NA oil immersion objective (Nikon).
Figure 14:
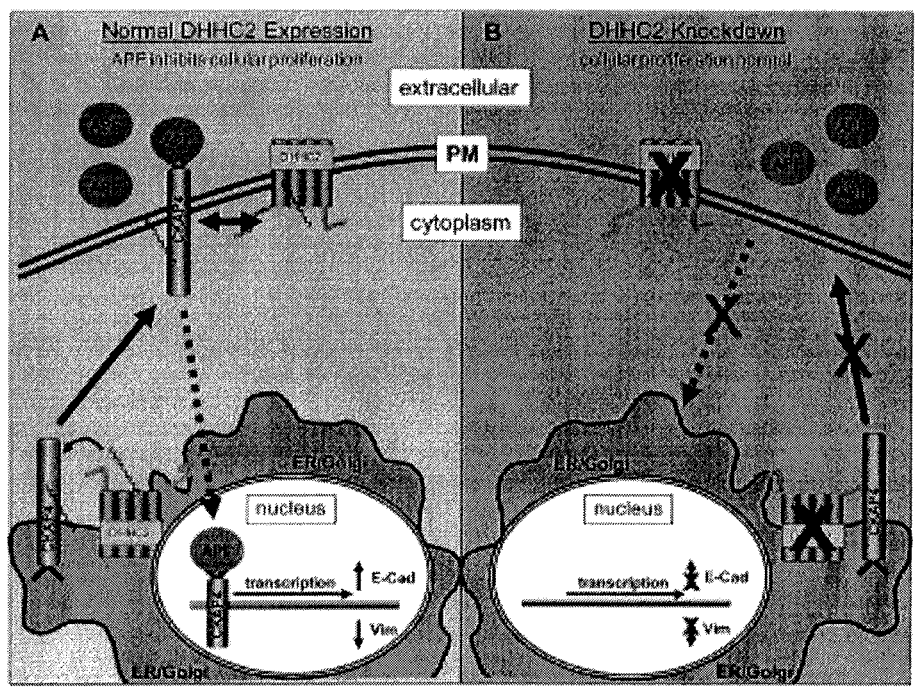
FIG. 14 shows that the palmitoylation of CKAP4 by DHHC2 is required for APF-mediated signaling. (14A) APF inhibits cellular proliferation and alters the expression of a specific set of genes by binding to its receptor, CKAP4 (Keay et al., 2003; Zhang et al., 2005; Kim et al., 2007). APF binds to CKAP4 with high affinity and this binding has been shown to be necessary for mediation of APF-related signaling events (Conrads et al., 2006). CKAP4 is also one substrate (of an unknown number) of the palmitoyl acyl transferase, DHHC2 (Zhang et al., 2008). (14B) siRNA-mediated knockdown of ZDHHC2 (the gene encoding the PAT, DHHC2) mRNA expression (see FIG. 6 half life or bar graph), prevents CKAP4 trafficking from the ER to the PM (see FIGS. 7 and 8) and in doing so, inhibits APF binding to CKAP4. Consequently, the inhibitory effect of APF on cellular proliferation (see FIG. 9) and APF-mediated changes in gene transcription (see FIGS. 10-12) are blocked. While it is likely that other substrates of DHHC2 exist, APF mediated changes in cellular proliferation and gene expression appear to be regulated by, DHHC2-mediated palmitoylation of CKAP4.
Figure 20:
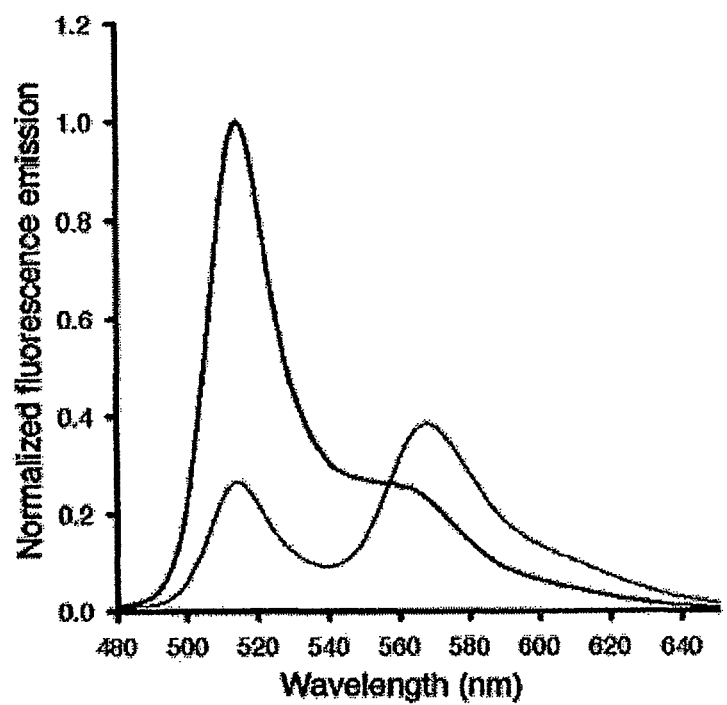

NCBI accessions—links to the sequences for the gene in NCBI databases including GenBank and Entrez Gene. Superscripts represent the source from which this data was extracted. If a '~' follows the superscript for HomoloGene, it means that data for this species exists only in the older version of HomoloGene, which used unfinished genomes and where the homologs found might not be true orthologs. The source of this information: www.genecards.org/info.shtml#ort FIG. 20 shows T.Sapphire mOrange FRET. Emission spectra for 400 nm excitation for a zinc-finger fused with mOrange on its N terminus and T-Sapphire on its C terminus. Emission in the presence of 1 mM EDTA in zinc-free buffer is represented by the green line, and emission in the presence of 1 mM $ZnCl_2$ is represented by the orange line.

Figure 21:
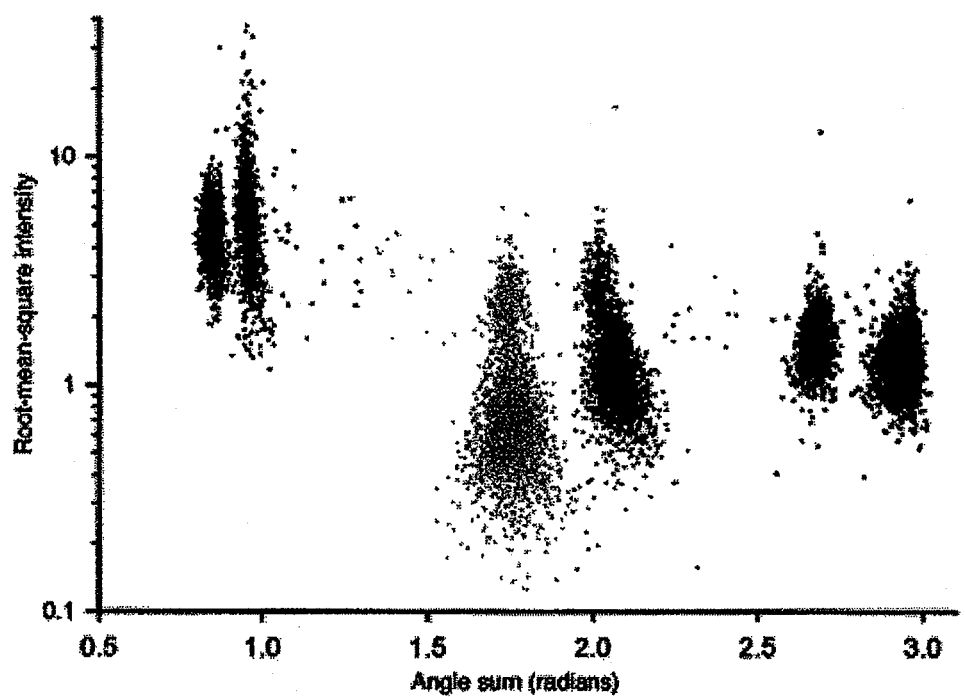

FIG. 21 shows discrimination of E. coli transfected with six different fluorescent proteins. Bacteria separately transformed with different fluorescent proteins were mixed and analyzed by flow cytometry for a total of about 10,000 events. Excitation was at 514 nm from an argon-ion laser. Emissions E1, E2, and E3 were simultaneously collected with 540-560 nm, 564-606 nm, and 595-635 nm bandpass filters respectively. Normalized fluorescence $F_i$ were calculated as $E_i$/ (mean of all $E_i$ values) for i=1, 2, 3. The root mean-square intensity (ordinate) was defined as (F/+F22+F/JII2, while the angle sum (abscissa) was tan-I(Fi1F1)+tan-I(F31F2) in radians. Each dot represents a cell. Control runs with pure populations verified that the dots represent GFP-expressing cells, dots represent Citrin YFP, mBanana, mOrange, mStrawberry, and mCherry.

Figure 22:
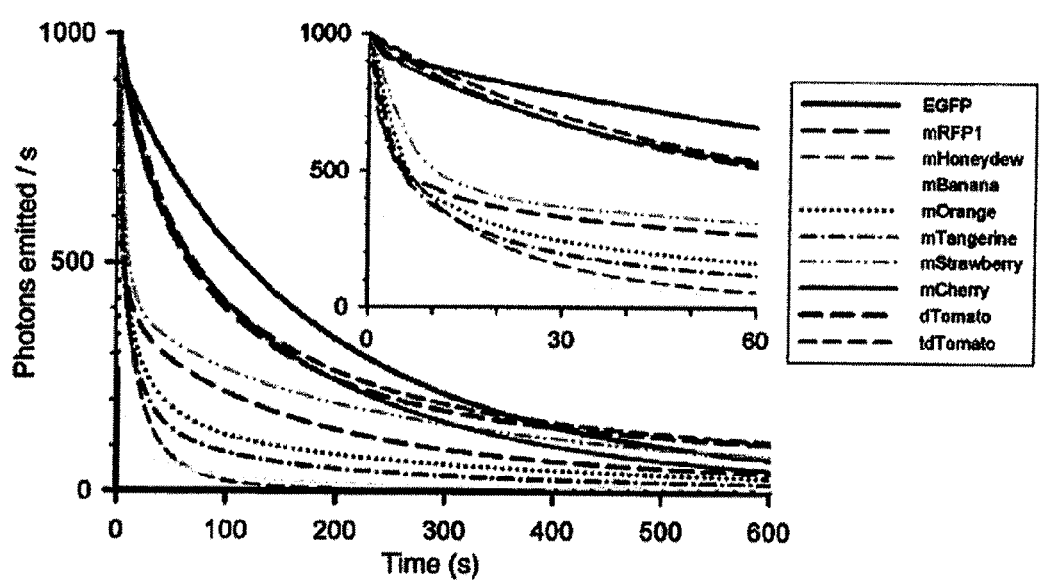

FIG. 22 shows photobleaching curves for new RFP variants. Curves for mRFP1 and EGFP are included for comparison. All curves are normalized to illumination intensities calculated to cause each molecule to emit 1,000 photons/s at time=0 before photobleaching. The inset is an expansion of the first 60 s of bleaching.

DETAILED DESCRIPTION OF PREFERRED EMBODIMENTS OF THE INVENTION

The invention provides, for example, a cell-based system whereby CKAP4, the receptor for APF, may be expressed at the cell membrane as a yellow fluorescent protein (YFP) fusion protein (CKAP4-YFP). Urine samples of patients with symptoms consistent with IC may be applied to the cell-based system. The presence of APF in the urine sample is detected when it binds to the CKAP4-YFP receptor protein. Binding of APF to CKAP4-YFP directs the receptor protein to translocate from the cell periphery (cellular plasma membrane) to the nucleus.

In another aspect, this invention is designed to detect APF in urine samples. This result, combined with patient symptoms would be diagnostic for IC and obviate the need for patients to undergo current diagnostic procedures whereby the patient is put under local anesthesia and an invasive procedure is performed to measure loss of thickening of the bladder wall. Thus, this invention would obviate the risks of anesthesia and invasive procedures and would also cost considerably less.

In another aspect, this invention is designed to distinguish IC from other conditions whose symptoms overlap with IC. Distinguishing one condition from another allows for a more directed therapeutic approach for patients with these symptoms. If the urine sample where negative for APF, diagnostic procedures that measure bacteria in urine (e.g., urinalysis, urine culture; cytology); that test for bladder carcinoma (cystoscopy, bladder biopsy, imaging tests [CT scan, MRI, sonogram, intravenous pyelogram, bone scan, chest x-ray]); overactive bladder (urinalysis, postvoid residual volume, simple cystometry, urodynamic testing, uroflowmetry, cystometrogram, cystoscopy, and imaging tests [x-ray, ultrasound]), and endometriosis (laparoscopy, histology) could then focus patient treatment using therapeutic strategies that target these other conditions.

This invention represents a significant advance for the diagnosis of IC. The invention is non-invasive and does not require anesthesia, indicating it is safer. The invention is estimated to cost a consumer $500 compared to current invasive diagnostic procedures which cost $10,000.00. This is a significant savings for consumers and insurance companies. This invention represents a significant advance in that it is much faster to diagnosis than current procedures (30 minutes compared to 1 week). This invention represents a surprising advance in that the biological activity of a biomarker for IC can be measured accurately and rapidly in a visual, high throughput system, improving diagnosis and treatment of IC. From an epidemiological standpoint, the ease (requires only the submission of a urine sample) and availability of the assay will mean that 1) many more patients that are suspected of having IC are more likely to be tested. It is possible that, due to the current difficulty in diagnosis, patients with milder or shorter term symptoms are not likely to be tested. The increase in the number of patients suspected of having IC that would be tested with this CKAP4:YFP assay may in time show that many more people have IC than previously believed. 2) The use of this test will more effectively exclude patients with IC symptoms that do not have the disease. The improvement in the delineating patient populations with previously indiscernible symptom boundaries will also improve our understanding of the epidemiology of IC and diseases that have similar symptomology.

From the symptomological standpoint, this assay will provide a concentration of APF in the urine of patients which can then be correlated to other factors such as age of onset, duration of time since the onset of symptoms, severity of symptoms and so forth. With a sufficient number of patients diagnosed in a database, a much clearer understanding of the progression of the disease can be obtained.

The assay itself is conceptually simple. The metric for diagnosis is the absence or presence of CKAP4:YFP fluorescence in the nucleus following the application of patient urine to the CKAP4:YFP reporter cells in culture; the nucleus being defined by labeling with one of many fluorescent dyes that bind nuclear DNA with exquisite specificity. Such dyes have no spectral overlap with the fluorescence associated with CKAP4:YFP. There are many ways to determine the absence or presence of CKAP4:YFP in the nucleus ranging from qualitative, simple visual inspection by a trained professional to a quantitative, morphometric instrument—vision analysis on a microscope without any unintended analyst biases. An alternative approach to using a stably-expressed, fluorescent reporter to measure APF in the urine is to use immunolabeling of endogenous CKAP4. The metric in this case would remain the same—abundance of CKAP4 in the nucleus. The labor involved in immunodetection is somewhat greater than it would be using CKAP4:YFP but may offer an advantage of long-term stability of the cellular response to APF.

Analysis by an unbiased instrument with a robust assay has the most potential to provide the highest density of data. However, alternative methods exist to make the same measurement. One of these is the measurement of CKAP4 abundance in the nucleus by Western blot following biochemical fractionation of the nucleus from all other cell fractions. The diagnostic metric in this case is the increased abundance of CKAP4 (either endogenous or the stably-expressed CKAP4:YFP) relative to another marker with specificity to the nucleus such as fibrillarin (see FIG. 4). This method would be significantly more labor intensive (the biochemical fractionation would add at least one hour of human labor to the measurement) but would also provide a quantitative measure of CKAP4 in the nucleus. The dynamic range of this detection method would not likely be as great as using the cell-based assay if the Western blot signal were detected by enhanced chemiluminescence (ECL)—captured on autofluorographic film. The dynamic range of ECL detection is limited by the dynamic range potential of the photographic film as well as by the length of film exposure to the signal emanating from the blot. However, an approach that could provide rapid and sensitive detection by Western blot with a wide dynamic range would be to label the antibodies used in the detection with radioisotope (other than tritium). The detection system in this case would be an instrument such as the PhosphorImager (Molecular Dynamics).

APF Activity Assay

In the assay of the present invention, a recombinant cell is exposed to a sample which may or may not contain APF. To determine whether or not APF is present in the sample, to quantitate an amount of APF in the sample, or to measure the biological activity of APF, for example, the expression of a reporter gene may be measured.

The recombinant cell may be contacted with the sample for a time sufficient to activate the receptor, for example CKAP4, translocate to the cell nucleus, induce transcription, and produce the reporter protein, which may or may not be secreted from the cell. The time required for the assay will vary with the assay conditions and with the specific reporter protein, as known to those in the art. Generally, the cells will be incubated in the presence of sample for about 30 minutes to about 24 hours, after which time the reporter protein may be assayed.

Reporter gene expression can be measured using any known method. Although it is preferable that expression of the reporter gene be easily detected, the reporter gene can be any gene that expresses a detectable gene product such as RNA or protein. Therefore, expression of the gene product can be determined using Northern or Western blot assays. Alternatively, the gene product can be selected because it is easily measured. Examples of reporter genes encoding more easily measured gene products include, but are not limited to, alkaline phosphatase, luciferase, β-galactosidase, chloramphenicol acetyl transferase (CAT), lux operon, green fluorescent protein (GFP), and/or fluorescent protein variants. The alkaline phosphatase gene product is secreted and therefore may be very easily measured in the conditioned culture medium.

The assay may be run simultaneously with a second control assay wherein the control recombinant cell does not contain a APF-responsive protein, such as, for example CKAP4. The assay may be run simultaneously with a second control assay wherein the control sample does not contain APF, but the recombinant cell contains an APF responsive protein, such as, for example CKAP4. The assay may be run simultaneously with a control set of APF standards to generate a standard curve from which sample concentrations of APF can be quantitated.

Nucleic Acids

A "APF responsive protein" is a protein that is capable of binding APF, wherein the activity of the APF-responsive protein is altered in response to the binding, for example CKAP4. In one embodiment, the protein can be a cell surface protein such as an APF receptor, such as CKAP4. In this embodiment, binding of APF to the APF-responsive protein results in the translocation to the cell nucleus.

The recombinant cell used in the assay of the present invention may contain either an endogenous or heterologous DNA sequence encoding the APF-responsive protein. An endogenous DNA sequence is a DNA sequence that is naturally present in the genome of a cell such that the cell naturally expresses the APF-responsive protein. A heterologous DNA sequence includes a DNA sequence that does not occur naturally as part of the genome in which it is present. Additionally, a heterologous DNA sequence includes a DNA sequence in a location or locations in the genome that differs from the location(s) in which it occurs in nature. Methods for introducing heterologous DNA into a host cell are well known in the art and any such method may be used.

Capital letters indicate restriction sites described in FIG. 3; underlined nucleotides are complimentary to the coding sequences of their respective mRNA or cDNA. Nucleotides are ordered according to convention from 5' to 3'.

```
CKAP4 Primers
5' RT PCR primer:
                                              (SEQ ID NO: 1)
5'-caccGGTACCatgccctcggccaaacaaagg-3'

3' RT PCR primer:
                                              (SEQ ID NO: 2)
5'-aattCTCGAGgaccttttcgtgaatcttctccactttcac-3'

YFP Primers
5' PCR primer:
                                              (SEQ ID NO: 3)
5'-tattCTCGAGatggtgagcaagggcgagga-3'

3' PCR primer:
                                              (SEQ ID NO: 4)
5'-ctcgGAATTCttacttgtacagctcgtcca-3'
```

CKAP4 mRNA sequence: DEFINITION Homo sapiens cytoskeleton-associated protein 4 (CKAP4), mRNA. ACCESSION NM_006825. The coding sequence, what is translated, nucleotides 85-1893, is underlined (SEQ ID NO: 5).

```
  1 gggggagccc ctgcaagttt cccgggccgc gcgccgcgct cgctcgcctc ccagcccgcg
 61 gcccgagccg ccgccgcgcc cgccatgccc tcggccaaac aaagggggctc caagggcggc
```

-continued

```
 121 cacggcgccg cgagcccctc ggagaagggt gcccacccgt cgggcggcgc ggatgacgtg
 181 gcgaagaagc cgccgccggc gccgcagcag ccgccgccgc cgcccgcgcc gcacccgcag
 241 cagcacccgc agcagcaccc gcagaaccag gcgcacggca agggcggcca ccgcggcggc
 301 ggcggcggcg gcggcaagtc ctcctcctcc tcctccgcct ccgccgccgc tgccgccgcc
 361 gccgcctcgt cctcggcgtc ctgctcgcgc aggctcggca gggcgctcaa ctttctcttc
 421 tacctcgccc tggtggcggc ggccgctttc tcgggctggt gcgtccacca cgtcctggag
 481 gaggtccagc aggtccggcg cagccaccag gacttctccc ggcagaggga ggagctgggc
 541 cagggcttgc agggcgtcga gcagaaggtg cagtctttgc aagccacatt tggaactttt
 601 gagtccatct tgagaagctc ccaacataaa caagacctca cagagaaagc tgtgaagcaa
 661 ggggagagtg aggtcagccg gatcagcgaa gtgctgcaga aactccagaa tgagattctc
 721 aaagacctct cggatgggat ccatgtggtg aaggacgccc gggagcggga cttcacgtcc
 781 ctggagaaca cggtggagga gcggctgacg gagctcacca atccatcaa cgcaacatc
 841 gccatcttca cagaagtcca gaagaggagc cagaaggaga tcaatgacat gaaggcaaag
 901 gttgcctccc tggaagaatc tgaggggaac aagcaggatt tgaaagcctt aaaggaagct
 961 gtgaaggaga tacagacctc agccaagtcc agagagtggg acatggaggc cctgagaagt
1021 acccttcaga ctatggagtc tgacatctac accgaggttc gcgagctggt gagcctcaag
1081 caggagcagc aggctttcaa ggaggcggcc gacacggagc ggctcgccct gcaggccctc
1141 acgagaaagc ttctcaggtc tgaggagtcc gtctcccgcc tcccggagga gatccggaga
1201 ctggaggaag agctccgcca gctgaagtcc gattcccacg ggccgaagga ggacggaggc
1261 ttcagacact cggaagcctt tgaggcactc cagcaaaaga gtcagggact ggactccagg
1321 ctccagcacg tggaggatgg ggtgctctcc atgcaggtgg cttctgcgcg ccagaccgag
1381 agcctggagt ccctcctgtc caagagccag gagcacgagc agcgcctggc cgccctgcag
1441 gggcgcctgg aaggcctcgg gtcctcagag gcagaccagg atggcctggc cagcacggtg
1501 aggagcctgg gcgagaccca gctggtgctc tacggtgacg tggaggagct gaagaggagt
1561 gtgggcgagc tccccagcac cgtggaatca ctccagaagg tgcaggagca ggtgcacacg
1621 ctgctcagtc aggaccaagc ccaggccgcc cgtctgcctc ctcaggactt cctggacaga
1681 ctttcttctc tagacaacct gaaagcctca gtcagccaag tggaggcgga cttgaaaatg
1741 ctcaggactg ctgtggacag tttggttgca tactcggtca aaatagaaac caacgagaac
1801 aatctggaat cagccaaggg tttactagat gacctgagga atgatctgga taggttgttt
1861 gtgaaagtgg agaagattca cgaaaaggtc taaatgaatt gcgtgtgcag ggcgcggatt
1921 taaagtccaa tttctcatga ccaaaaaatg tgtggttttt tcccatgtgt cccctacccc
1981 ccaatttctt gtcccctctt aaagagcagt tgtcaccacc tgaacaccaa ggcattgtat
2041 tttcatgccc agttaactta tttacaatat ttaagttctc tgcttctgca tttggttggt
2101 ttcctgaagc gcagccctg tgaataacag gtggcttttc atggatgtct ctagtcagag
2161 aaaaatgata aaggcttaaa ttgaggatta acagaagcag attaacctca gaaatcctgt
2221 ctggctggca gatttcaagt aaaaaaaaaa aaaggtgggg ttgggggggac ccttttcttt
2281 ctagttgtct ttaaggaaaa ttaattttac ttttttttttt gttctggccg aaattttat
2341 gagatatctc tcacttgtct tccactttga accggttaaa gctcatagct gtcagctctg
2401 aatgaggagg ggagaagccc ctgggtcttt cttgaaagg aatccgctgc ttgagggctg
2461 cctccctcat ggtgtgcgtg tcgttctctt cctgacgcat ctgtgatatc agaggtaact
```

```
2521 atgcaaagca tccaggcggt tctgaatgtg aagcactaca cccagcagag tcccggtgcc 2581 ctctgtcccc actgccggcc catgtcctct ctccggaggt caccaaggaa tgcacaggtt 2641 tcgactacca gaaaggggag tccttgggtt ctttcaaaaa attcgtgagg agagctgtct 2701 acagtggaat aggggggtctc cctggggaat gcaggccaag tcctttttatt ttaacatgat 2761 gtccatgaag aggtttgccg tctgggcagc cctgtcggca aggagcgtgc atactgcgtt 2821 tgtgtaattg tttgctgtat ctcccttccc tctgagctgt attgttcttt aatggctgtc 2881 ttgcccttcc aaaaaaaatt gaaaaaaaaa aaa
```

The protein sequence encoded by the mRNA (CKAP4 Genebank accession number NM_006825) contains the following sequence of amino acid residues and (Genebank accession number NP_006816.2) (SEQ ID NO: 6):

MPSAKQRGSKGGHGAASPSEKGAHPSGGADDVAKKPPPAPQQPPPPPAP

HPQQHPQQHPQNQAHGKGGHRGGGGGGGKSSSSSSASAAAAAAAASSSA

SCSRRLGRALNFLFYLALVAAAAFSGWCVHHVLEEVQQVRRSHQDFSRQ

REELGQGLQGVEQKVQSLQATFGTFESILRSSQHKQDLTEKAVKQGESE

VSRISEVLQKLQNEILKDLSDGIHVVKDARERDFTSLENTVEERLTELT

KSINDNIAIFTEVQKRSQKEINDMKAKVASLEESEGNKQDLKALKEAVK

EIQTSAKSREWDMEALRSTLQTMESDIYTEVRELVSLKQEQQAFKEAAD

TERLALQALTEKLLRSEESVSRLPEEIRRLEEELRQLKSDSHGPKEDGG

FRHSEAFEALQQKSQGLDSRLQHVEDGVLSMQVASARQTESLESLLSKS

QEHEQRLAALQGRLEGLGSSEADQDGLASTVRSLGETQLVLYGDVEELK

RSVGELPSTVESLQKVQEQVHTLLSQDQAQAARLPPQDFLDRLSSLDNL

KASVSQVEADLKMLRTAVDSLVAYSVKIETNENNLESAKGLLDDLRNDL

DRLFVKVEKIHEKV

APF Protein:

3 carbohydrate moieties-T-V-P-A-A-V-V-V-A

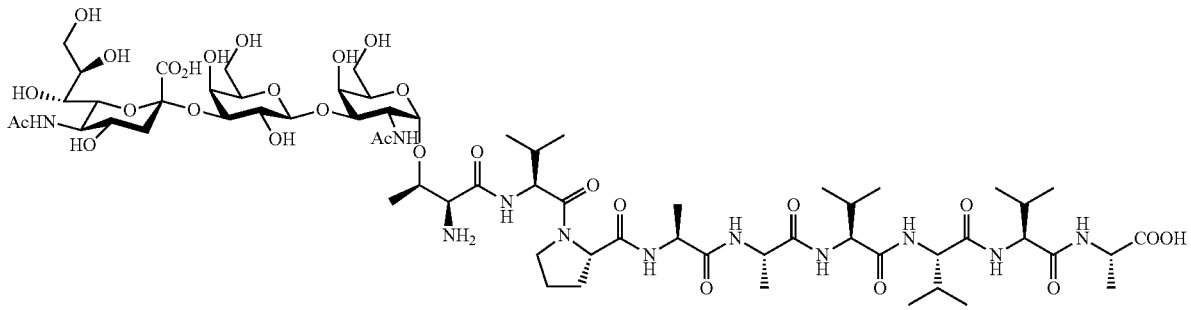

DHHC2 mRNA: DEFINITION Homo sapiens zinc finger, DHHC-type containing 2 (ZDHHC2), mRNA. ACCESSION NM_016353; VERSION NM_016353.4 GI:209180414 (SEQ ID NO: 7):

```
  1 gtgggagccc gcgaggtggc ccgagcgagg gccccgcatc cccgcagagc ccgcccgagg 61 gcgcagcctg ccacgccagg ggaggcggcc gggcggcggg gaacggcggg ggcggagcgc 121 agcctcccga cgccgccgcc tcaccgcccc cctccgcctc ctcggcctcc gctcgcagcc 181 gccgcctccg cctccgccgg gctgaggagc cgggagtccg ccgcgccggc tcggggctgc 241 gggatgggga gttagcgcca cggcggcggc agtggccgca gcgcaccccg ccgccgccca 301 ggagcccgtc cagccagggg tgccgggccc gcccagcccg ccccggagcc aggcccgcgg 361 gcggcggcgg agctgggcag gtggatgcgg ctggaagatg gcgccctcgg gcccgggcag 421 cagcgccagg cggcggtgcc ggcgggtgct gtactggatc ccggtggtgt tcatcaccct 481 cctgctcggc tggtcctact acgcctacgc catccagctg tgcatagtgt ccatggaaaa 541 cactggcgaa caagttgtgt gcctgatggc ctatcatcta cttttttgcaa tgtttgtctg
```

-continued

```
601   gtcatactgg aaaactatct ttacattacc aatgaatcct tcaaaagaat tccatctctc
661   ttatgcagag aaagatttgt tggagagaga gccaagagga gaagcccatc aggaagttct
721   taggcgagca gccaaggatc ttcccatcta taccaggacc atgtctggag ccatccgata
781   ctgtgacaga tgccaactta taaaaccaga tcgctgccat cactgctccg tctgtgataa
841   atgtattttg aagatggatc atcattgtcc atgggtgaac aattgtgttg gattttcaaa
901   ttataagttc tttctccttt tcttggctta ttctctgctc tactgccttt ttattgcggc
961   aacagattta cagtatttta tcaaattttg dacaaatggc ctacctgata ctcaagccaa
1021  gttccatatt atgttttat tctttgctgc agctatgttt tctgtcagct tgtcttctct
1081  gtttggctat cattgttggc tagtcagcaa aaataaatct acattagagg cattcagaag
1141  tccagtattt cgacatgaaa cagataagaa tggattcagc ttgggtttca gtaaaaacat
1201  gcgacaagtt tttggtgatg agaagaagta ctggttgcta cccattttt caagtctagg
1261  tgatggctgc tccttttccaa cttgccttgt taaccaggat cctgaacaag catctactcc
1321  tgcagggctg aattccacag ctaaaaatct cgaaaaccat cagtttcctg caaagccatt
1381  gagagagtcc cagagccacc ttcttactga ttctcagtct tggacggaga gcagcataaa
1441  cccaggaaaa tgcaaagctg gtatgagcaa tcctgcatta accatggaaa atgagactta
1501  actcttcaag caagataaat tcatacttta taaaagtatc aatgctgtag atggatggaa
1561  gaggcttccc acaggaaggt gccaccagtc agttgtgcct atgtcccttt ggctggaaat
1621  gcagaatatg aattgattag ttctctccaa gccattgctt aaaatataac atgttttgga
1681  tccaatacac acattgttac aactaacaca aattcctatt aaatattaaa agtagttctg
1741  gtttattaat caacggggaa aacatcttct ccaaaaaact tggaataaat ccaaggacca
1801  gttttttaccc aaatatatgg gtagcacagt ttatcacata gaaactccat taatcatctg
1861  attttccgaa tctgaaaatt gagactatta agatattagg atttcagaga tttcaagtca
1921  cattataatg ataagcatta ttcataaaac ttgttacctt taagaaggtg gaagtggcaa
1981  accatacttc ttttttttcc tctgatgtga atccagcctc agactgagtg aactgtaata
2041  attatgaatt cattacagag tccaggtggc ctgcagttga agatcatcaa ccattttgc
2101  ctcacttaat tccagccttt tgttttctgc tggaaaataa gtgtggacat tgaagcttga
2161  gctctcaaag cagttggctg gaatactttt gtcagaatac ggtacatttc tattacatca
2221  gaaatatatt ttcatctctt cttgttaaat tgggaggaaa tttatgatag caattatgaa
2281  gattgtttta tgacattctt ttgtcagttt ggctttctaa aaatctcttt ttagattatt
2341  tctcctgttg aacatagtaa aactattgaa tttctcttaa gaattcctaa taggtcaata
2401  gatttacccct ccagtgatat ctatattatt tctttctcgt ctcatcaaaa tgatgacagg
2461  taaactatat ttttccttaa acacctatta cagttaaatt atgcaaatca ttaaataaaa
2521  atcatacaac ttttggaaag ttagttcaac atgaactaaa atggcatgct atttggaaat
2581  ttagtttgag ataaactaaa gtgtgttgat gccagaatgt tcagcttcag taaatataat
2641  aagctcttgt gccttgtatg cactatttaa aaaagttttt tttatttga gtccagtata
2701  attcatgtaa atgttaacaa ttagaataat actctgtatg cttttttgat actgattttg
2761  agaatttaaa gcagattacc ttttaaaact ggaccaacta agtaattggt atttaatcaa
2821  agagaaaatg gtaataaact tttcaaaatc tttgttaaac caaacattca acacaaaata
2881  aactagaagg ccagaggata atggaataaa agatcattgc aattacttat ccttcctaaa
2941  aatatagttt tatattaatt gtgcttatgg aagaaacaat gtcagccaag tccatttat
3001  agtttgagtg caattctttg aacaatagaa atatctgcag tctttcacag atttgtatta
```

```
3061 tgctgaagag tttcatctga caatctgctt caagaaatct cagaaaatat gataacattt 3121 taactttcat tttagagcac gttttggtca tttttaaaaa tacctaaagt gccagaccgg 3181 aacctatagc tactgctaga agtcttaaaa aaaccaacag cagcacagga tgtattaaga 3241 attatatgaa gtcaggtttg tttttttttt tttttttttt tcaaagcaca gtactgttag 3301 ctgttttgt ggacaggatt cgattaagta ttccctcttg tcaaactgga agctagggga 3361 aaaagaggga tttttatcct ttactcttct agagtactgt taatgcccct ttcccacagt 3421 cttttatata attaaatata tgtcaataca cattagaatc agatttgaaa aagttaaaac 3481 aatttcattg ttgtaattgt tcccttctg ttttcatata gtgaataacc tttaaagggt 3541 tgttttgttt tgttttgaat tataggagtt ataatctttg gagatgattg catatctcat 3601 tagatatgca atataaattt atctgagtga acaaagtgct aaataaatag atctacattt 3661 tgtacatatt tatataaaat ttacctttaa gtatttactt taaaaaattt aatggcttaa 3721 ctcgaacttg aagacacata cttcaactgt ccttattgtc cattaaactg ataattttga 3781 tttttcttgc ttttatagat tttactatat aggaatcaag atttaagaaa ttttgcatta 3841 aaaatagtgt accaatgctt catatacgtt agttatttgc tattatgtag ggaagaggat 3901 tgttatttca aagatatatt aaagaacagt tgcatctgaa tataatcatg atgcattcaa 3961 tgaagttcat atccatgaat tcactcctaa tataccctaa taaagtggtt ga
```

DHHC Protein (SEQ ID NO: 8):

MAPSGPGSSARRRCRRVLYWIPVVFITLLLGWSYYAYAIQLCIVSMEN

TGEQVVCLMAYHLLFAMFVWSYWKTIFTLPMNPSKEFHLSYAEKDLLE

REPRGEAHQEVLRRAAKDLPIYTRTMSGAIRYCDRCQLIKPDRCHHCS

VCDKCILKMDHHCPWVNNCVGFSNYKFFLLFLAYSLLYCLFIAATDLQ

YFIKFWTNGLPDTQAKFHIMFLFFAAAMFSVSLSSLFGYHCWLVSKNK

STLEAFRSPVFRHGTDKNGFSLGFSKNMRQVFGDEKKYWLLPIFSSLG

DGCSFPTCLVNQDPEQASTPAGLNSTAKNLENHQFPAKPLRESQSHLL

TDSQSWTESSINPGKCKAGMSNPALTMENET

The fluorescent reporter construct CKAP4:YFP may be generated using the following methods. The cDNA for human CKAP4 was cloned by reverse transcription polymerase chain reaction (RT-PCR) from a HeLa cell cDNA library. Primers for amplifying the cDNA were purchased from (Integrated DNA Technologies). A 5' primer (sequence) incorporating the endonulcease restriction site KpnI at the 5' end of the primer and homology to the CKAP4 cDNA at the 3' end of the primer was used in conjunction with a 3' primer that incorporated a restriction site for the endonulcease XhoI to amplify the CKAP4 cDNA from the library. The amplified product was isolate from an agarose gel and purified using a PCR purification kit (Qiagen). The PCR product was then digested using the endonucleases (X and Y) to prepare it for cloning into the mammalian expression vector pcDNA3 (purchased from Invitrogen).

The cDNA for the Yellow Fluorescent Protein (YFP), a spectral mutant or color variation of the Green Fluorescent protein from the jellyfish *Aequorea Victoria*, may be obtained from (Clontech). To subclone YFP in-frame directly to the carboxy-terminus of CKAP4 with no intervening linker sequence, primers complimentary to the 5' and 3' ends of the coding sequence of monomeric YFP were made and included XhoI and EcoRI sites respectively.

cDNA sequence of monomeric *Aequorea victoria* Yellow Fluorescent Protein YFP DEFINITION Synthetic construct fluorescent protein mVenus mRNA, complete cds. ACCESSION DQ092360 (SEQ ID NO: 9):

```
  1 atggtgagca agggcgagga gctgttcacc ggggtggtgc ccatcctggt cgagctggac 61 ggcgacgtaa acggccacaa gttcagcgtg tccggcgagg gcgagggcga tgccacctac 121 ggcaagctga ccctgaagct gatctgcacc accggcaagc tgcccgtgcc ctggcccacc 181 ctcgtgacca ccctgggcta cggcctgcag tgcttcgccc gctaccccga ccacatgaag 241 cagcacgact tcttcaagtc cgccatgccc gaaggctacg tccaggagcg caccatcttc 301 ttcaaggacg acggcaacta caagacccgc gccgaggtga agttcgaggg cgacaccctg 361 gtgaaccgca tcgagctgaa gggcatcgac ttcaaggagg acggcaacat cctggggcac 421 aagctggagt acaactacaa cagccacaac gtctatatca ccgccgacaa gcagaagaac 481 ggcatcaagg ccaacttcaa gatccgccac aacatcgagg acggcggcgt gcagctcgcc
```

-continued

```
541 gaccactacc agcagaacac ccccatcggc gacggccccg tgctgctgcc cgacaaccac 601 tacctgagct accagtccaa gctgagcaaa gacccaacg agaagcgcga tcacatggtc 661 ctgctggagt tcgtgaccgc cgccgggatc actctcggca tggacgagct gtacaagtaa ttacttgtacagctcgtcca
```

Protein sequence of monomeric Yellow Fluorescent Protein from *Aequorea victoria*. /protein_id="AAZ65844.1" GI:72003806". The sequence of the amino acid residues is from the amino terminus to the carboxy terminus (SEQ ID NO: 10):

MVSKGEELFTGVVPILVELDGDVNGHKFSVSGEGEGDATYGKLTLKLIC

TTGKLPVPWPTLVTTLGYGLQCFARYPDHMKQHDFFKSAMPEGYVQERT

IFFKDDGNYKTRAEVKFEGDTLVNRIELKGIDFKEDGNILGHKLEYNYN

SHNVYITADKQKNGIKANFKIRHNIEDGGVQLADHYQQNTPIGDGPVLL

PDNHYLSYQSKLSKDPNEKRDHMVLLEFVTAAGITLGMDELYK

One aspect of the present invention is the polynucleotide sequences essentially as set forth above, the complement of these sequences, the RNA versions of both DNA strands and the information otherwise contained within the linear sequence of these polynucleotide sequences, and fragments thereof. The polynucleotide encoding CKAP4, APF, and/or DHHC2 is exemplified as set forth above. In the case of nucleic acid segments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between 91% and about 99%; or which contain nucleotides that are identical, functionality equivalent, or functionally irrelevant, with respect to the nucleotides set forth above are considered to be essentially similar. Also encompassed within the present invention are nucleic acids that encode polypeptides that are at least 40% identical or similar to the amino acid sequences as shown.

The invention also encompasses other nucleic acids or nucleic acid like molecules that are sufficient in any regard to mimic, substitute for, or interfere with the CKAP4 and/or APF polynucleotide sequences, as exemplified as set forth above, or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality, or for the purpose of engineering altered functionality with respect to CKAP4, DHHC2 and/or APF.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences as set forth above, under stringent or under permissive hybridization conditions, or to the complement of said sequences.

The invention also includes oligonucleotide, or oligonucleotide-like sequences such as phosphorothioate, or peptide nucleic acid sequences, which possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art. In addition to the sequences disclosed here, related sequences in other organisms, or homologs, will be readily identified by hybridization using the present sequences. Similar techniques will also apply to the identification of mutant alleles, polymorphisms, deletions, insertions, and so forth, in genomic and cDNA sequences. Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60-80 degrees Celsius may be substantially purified.

It will be understood that this invention is not limited to the particular nucleic acid sequences presented herein. Recombinant vectors, including for example plasmids, phage, viruses, and other sequences, and isolated DNA or RNA segments may therefore variously include the CKAP4, APF and/or DHHC2 gene sequences or their complements, and coding regions, as well as those that may bear selected alterations or modifications that nevertheless include CKAP4, APF and/or DHHC2 segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

Proteins and Polypeptides

One aspect of the invention is the protein, polypeptide, oligopeptide, or amino acid sequences or fragments thereof, of CKAP4, APF and/or DHHC2, essentially as set forth above. The CKAP4, APF and/or DHHC2 polypeptide is exemplified above. Sequences that have greater than about 40-50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented above are included. The invention thus applies to CKAP4, APF and/or DHHC2 polypeptide sequences, or fragments thereof, and nucleic acids which encode such polypeptides, such as those of other species. Reference is particularly, but not exclusively, made to the conserved regions of CKAP4, APF and/or DHHC2, in contrast to similarity throughout the entire length.

The invention thus encompasses amino acid sequences, or amino acid-like molecules, that are sufficient in any regard to mimic, substitute for, or interfere with the CKAP4, APF and/or DHHC2 amino acid sequences, or fragments thereof.

The invention encompasses CKAP4, APF and/or DHHC2 amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, and those that affect interactions between CKAP4, APF and/or DHHC2 other proteins, other nucleic acid regions, and other proteins. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, lip, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the CKAP4, APF and/or DHHC2 polypeptides.

Methods to produce and purify said polypeptides in eukaryotic systems are widely available and understood by those proficient in the art. Cells for such production are known to include yeast and other fungi, Drosophila and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

Vectors

Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®. 2.0 from INVITROGEN® and BACPACK® BACULOVIRUS EXPRESSION SYSTEM FROM CLONTECH.

Vectors may be of bacterial origin, which may comprise a promoter of a bacteriophage such as phage or T7 which is capable of functioning in the bacteria. In one of the most widely used expression systems, the nucleic acid encoding the CKAP4, APF and/or DHHC2 may be transcribed from the vector by T7 RNA polymerase (Studier et al, Methods in Enzymol. 185: 60-89, 1990). In the *E. coli* BL21 (DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for over-production of many proteins. Alternatively, the polymerase gene may be introduced on a lambda phage by infection with an int-phage such as the CE6 phage, which is commercially available (Novagen, Madison, USA). Other vectors include vectors containing the lambda PL promoter such as PLEX® (Invitrogen, NL), vectors containing the trc promoters such as pTrcHisXpress® (Invitrogen), or pTrc99 (Pharmacia Biotech, SE), or vectors containing the tac promoter such as pKK223-3 (Pharmacia Biotech), or PMAL (New England Biolabs, MA, USA).

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as *E. coli* HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/CaPO4 co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., Molecular Biomethods Handbook, Chapter 20, p. 235-250.

According to another embodiment of the instant invention, in vitro transcription is carried out on a recombinant plasmid carrying a cloned cDNA of the invention, under the control of an expressible promoter (i.e., a promoter which is effectively enabled or activated in vitro in the presence of corresponding transcription factors and RNA polymerase). The transcription process generates a fully-infectious mRNA transcript that can be used to transfect (i.e., infect) a cell host, such as BHK-21 (hamster kidney cells) or Vero cells. In one embodiment, the cDNA is operably linked with the bacteriophage transcriptional promoter, T7; to enable the in vitro transcription of the cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of, for example, the CKAP4, APF and/or DHHC2 gene, or fragment thereof, and for controlling the expression of a nucleotide sequence encoding a reporter is contemplated by the present invention. It will be appreciated that the promoter is typically selected from promoters which are functional in mammalian cells susceptible to infection by the CKAP4, APF and/or DHHC2 gene, or fragment thereof, encoding sequences of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of, for example, the CKAP4 and/or APF gene, or fragment thereof, encoding sequence or construct is to occur.

With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, Wnt-1 and Rhodopsin promoters, respectively. For example, the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter, the human cytomegalovirus (CMV) IE promoter, or SV40 promoter.

It may also be advantageous for the promoters to be inducible so that the levels of expression of, for example, the CKAP4, APF and/or DHHC2 gene, or fragment thereof encoding sequence can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

Plasmid Vectors

Any plasmid vector that allows expression of a differentially expressed coding sequence of the invention in a selected host cell type is acceptable for use according to the invention. A plasmid vector useful in the invention may have any or all of the above-noted characteristics of vectors useful according to the invention. Plasmid vectors useful according to the invention include, but are not limited to the following examples: Bacterial-pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, and pRIT5 (Pharmacia); Eukaryotic-pWLneo, pSV2cat, pOG44, pXT1, pSG (Stratagene) pSVK3, pBPV, pMSG, and pSVL (Pharmacia). However, any other plasmid or vector may be used as long as it is replicable and viable in the host.

Bacteriophage Vectors.

There are a number of well known bacteriophage-derived vectors useful according to the invention. Foremost among these are the lambda-based vectors, such as Lambda Zap II or Lambda-Zap Express vectors (Stratagene) that allow inducible expression of the polypeptide encoded by the insert. Others include filamentous bacteriophage such as the M13-based family of vectors.

Viral Vectors.

A number of different viral vectors are useful according to the invention, and any viral vector that permits the introduction and expression of one or more of the differentially expressed polynucleotides of the invention in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semliki forest viral (alphaviral) vectors. Defective retroviruses are well characterized for use in gene transfer (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

In addition to retroviral vectors, Adenovirus can be manipulated such that it encodes and expresses a gene product of interest but is inactivated in terms of its ability to replicate in a normal lytic viral life cycle (see for example Berkner et al., 1988, BioTechniques 6:616; Rosenfeld et al., 1991, Science 252:431-434; and Rosenfeld et al., 1992, Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol. 158:97-129). An AAV vector such as that described in Traschin et al. (1985, Mol. Cell. Biol. 5:3251-3260) can be used to introduce nucleic acid into cells. A variety of nucleic acids have been introduced into different cell types using AAV vectors (see, for example, Hermonat et al., 1984, Proc. Natl. Acad. Sci. USA 81: 6466-6470; and Traschin et al., 1985, Mol. Cell. Biol. 4: 2072-2081).

Introduction of Vectors to Host Cells

Vectors useful in the present invention may be introduced to selected host cells by any of a number of suitable methods known to those skilled in the art. For example, vector constructs may be introduced to appropriate bacterial cells by infection, in the case of E. coli bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y.), but electroporation may also be used (Ausubel et al., 1988, Current Protocols in Molecular Biology, (John Wiley & Sons, Inc., NY, N.Y.)).

For the introduction of vector constructs to yeast or other fungal cells, chemical transformation methods are generally used (e.g. as described by Rose et al., 1990, Methods in Yeast Genetics, Cold Spring Harbor Laboratory Press, Cold Spring Harbor, N.Y.). For transformation of S. cerevisiae, for example, the cells are treated with lithium acetate to achieve transformation efficiencies of approximately 104 colony-forming units (transformed cells)/.mu.g of DNA. Transformed cells are then isolated on selective media appropriate to the selectable marker used. Alternatively, or in addition, plates or filters lifted from plates may be scanned for GFP fluorescence to identify transformed clones.

For the introduction of vectors comprising differentially expressed sequences to mammalian cells, the method used will depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation. These methods are detailed, for example, in Current Protocols in Molecular Biology (Ausubel et al., 1988, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, Lipofectamine™ (Life Technologies) or Lipo-Taxi™ (Stratagene) kits are available. Other companies offering reagents and methods for lipofection include BioRad Laboratories, CLONTECH, Glen Research, InVitrogen, JBL Scientific, MBI Fermentas, PanVera, Promega, Quantum Biotechnologies, Sigma-Aldrich, and Wako Chemicals USA. Following transfection with a vector of the invention, eukaryotic (e.g., human) cells successfully incorporating the construct (intra- or extrachromosomally) may be selected, as noted above, by either treatment of the transfected population with a selection agent, such as an antibiotic whose resistance gene is encoded by the vector, or by direct screening using, for example, FACS of the cell population or fluorescence scanning of adherent cultures. Frequently, both types of screening may be used, wherein a negative selection is used to enrich for cells taking up the construct and FACS or fluorescence scanning is used to further enrich for cells expressing differentially expressed polynucleotides or to identify specific clones of cells, respectively. For example, a negative selection with the neomycin analog G418 (Life Technologies, Inc.) may be used to identify cells that have received the vector, and fluorescence scanning may be used to identify those cells or clones of cells that express the vector construct to the greatest extent.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of CKAP4, APF and/or DHHC2, or variants produced as described above can be achieved by any of several widely available methods. Cells may be subject to freeze-thaw cycles or sonication to achieve disruption, or may be fractionated into subcellular components prior to further purification. Purification may be achieved by one or more techniques such as precipitation with salts or organic solvents, ion exchange, hydrophobic interaction, HPLC and FPLC chromatograpic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availability of purified recombinant proteins facilitates the generation of large quantities of RNA from cloned cDNA sequences. In contrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukaryotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., Molecular Biomethods Handbook, Chapter 26, p. 327-334 and Sambrook, J. and D. W. Russell, Molecular Cloning: A Laboratory Manual, Third Edition (2001).

The invention provides a dual luciferase reporter system for measuring recoding efficiencies in vivo or in vitro from a single construct see U.S. Pat. No. 6,143,502 (Grentzmann et al.). For example, the firefly luciferase gene (fluc) has been cloned behind the *renilla* luciferase gene (rluc) into an altered vector pRL-SV40 vector (Promega Corp., Madison, Wis.; catalog no. TB239). Other reporter genes may also be used, for example, green fluorescent protein, and variants thereof Expression features for initiation and termination of transcription and translation, as well as the nature of the two reporter genes (short enough to be efficiently synthesized in an in vitro translation system), allow application of the same reporter construct for in vivo and in vitro applications. Between the 5' reporter (rluc) and the 3' reporter (fluc) two alternative polylinkers have been inserted, yielding p2luc and p2luci. The p2luc polylinker has restriction sites for digestion with SalI, BamHI, and SadI, whereas the p2luci polylinker has restriction sites for digestion with SalI, ApaI, BglII, Eco47III, BamHI, SmaI, and SacI. The assay using these reporter plasmids combines rapidity of the reactions with very low background levels and provides a powerful assay. In vitro experiments can be performed in 96-well microtiter plates, and in vivo experiments can be performed in 6-well culture dishes. This makes the dual-luciferase assay suitable for high throughput screening approaches.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

A suitable recombinant cell for use in the present invention includes a protein that is responsive to APF and a reporter gene whose expression is modulated by the binding of APF to the APF-responsive protein, such as, for example, CKAP4. "Modulated" can include up-regulation or down-regulation.

A heterologous DNA sequence encoding the reporter gene can be introduced into the recombinant cell by transient transfection or by stable transfection of a vector containing the DNA sequence. Numerous methods are know for introducing foreign DNA into a host cell.

In one embodiment, the host cell contains an endogenous DNA sequence encoding a APF-responsive protein. In this embodiment, a DNA sequence encoding the reporter gene is introduced into the cell. In another embodiment, the host cell may or may not contain an endogenous DNA sequence encoding a APF-responsive protein. In this embodiment, a heterologous DNA sequence encoding the reporter gene can be co-transfected with another heterologous DNA sequence encoding a APF responsive protein. Alternatively, the heterologous DNA sequence encoding the reporter gene can be included within a construct that also includes a heterologous DNA sequence encoding a APF-responsive protein. In an exemplary embodiment, the recombinant assay cell stably expresses both the APF-responsive protein and the reporter gene.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE®. Competent Cells and SOLOPACK® Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12, etc. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Reporter Genes

The DNA encoding the reporter gene can be included within a DNA construct which further includes a transcriptional control sequence. A transcriptional control sequence can include regulatory elements such as promoter sequences, enhancer sequences, repressor sequences and the like. According to the present invention, the activity of the transcriptional control sequence can be affected by the binding of APF to a cell surface receptor, such as CKAP4. For example, the transcriptional control element is a APF/CKAP4-responsive promoter, which in the presence of APF/CKAP4, modulates expression of the reporter. For example, the APF/CKAP4-responsive promoter induces activity of the promoter in the presence of APF/CKAP4, resulting in expression of the reporter protein.

A promoter is a region of DNA upstream from the reporter gene with respect to the direction of transcription of the reporter gene and a transcription initiation site. It includes the RNA polymerase binding and transcription initiation sites and other regions such as repressor or activator protein binding sites.

The transcriptional control sequence is operatively linked to the DNA sequence encoding the reporter gene. Typically, the DNA sequences are included in a vector such as a plasmid, bacteriophage or yeast chromosome. The vector can also include other gene sequences such as a DNA sequence encoding the APF-responsive protein, resistance genes, enhancers or other regulatory elements such as terminators, polyadenylation sequences or nucleic acid sequences encoding signal peptides to direct the encoded protein to the cell surface.

Fluorescent Protein Variants

The present invention also provides polynucleotides encoding fluorescent protein variants as the reporter, where the protein can be a dimeric fluorescent protein, a tandem dimeric fluorescent protein, a monomeric protein, or a fusion protein comprising a fluorescent protein operatively linked to one or more polypeptides of interest. In the case of the tandem dimer the entire dimer may be encoded by one polynucleotide molecule. If the linker is a non-peptide linker, the two subunits will be encoded by separate polynucleotide molecules, produced separately, and subsequently linked by methods known in the art.

The invention further concerns vectors containing such polynucleotides, and host cell containing a polynucleotide or vector. Also provided is a recombinant nucleic acid molecule, which includes at least one polynucleotide encoding a fluorescent protein variant operatively linked to one or more other polynucleotides. The one or more other polynucleotides can be, for example, a transcription regulatory element such as a promoter or polyadenylation signal sequence, or a translation regulatory element such as a ribosome binding site. Such a recombinant nucleic acid molecule can be contained in a vector, which can be an expression vector, and the nucleic acid molecule or the vector can be contained in a host cell.

The vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993; each of which is incorporated herein by reference).

A vector for containing a polynucleotide encoding a fluorescent protein variant can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the fluorescent protein variant, for example, a tandem dimer fluorescent protein, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, BioTechniques 7:980-990, 1992; Anderson et al., Nature 392:25-30 Suppl., 1998; Verma and Somia, Nature 389:239-242, 1997; Wilson, New Engl. J. Med. 334:1185-1187 (1996), each of which is incorporated herein by reference).

Recombinant production of a fluorescent protein variant, which can be a component of a fusion protein, involves expressing a polypeptide encoded by a polynucleotide. A polynucleotide encoding the fluorescent protein variant is a useful starting material. Polynucleotides encoding fluorescent protein are disclosed herein or otherwise known in the art, and can be obtained using routine methods, then can be modified such that the encoded fluorescent protein lacks a propensity to oligomerize. For example, a polynucleotide encoding a GFP can be isolated by PCR of cDNA from *A. victoria* using primers based on the DNA sequence of *Aequorea* GFP. A polynucleotide encoding the red fluorescent protein from Discosoma (DsRed) can be similarly isolated by PCR of cDNA of the Discosoma coral, or obtained from the commercially available DsRed2 or HcRed1 (CLONTECH). PCR methods are well known and routine in the art (see, for example, U.S. Pat. No. 4,683,195; Mullis et al., Cold Spring Harbor Symp. Quant. Biol. 51:263, 1987; Erlich, ed., "PCR Technology" (Stockton Press, NY, 1989)). A variant form of the fluorescent protein then can be made by site-specific mutagenesis of the polynucleotide encoding the fluorescent protein. Similarly, a tandem dimer fluorescent protein can be expressed from a polynucleotide prepared by PCR or obtained otherwise, using primers that can encode, for example, a peptide linker, which operatively links a first monomer and at least a second monomer of a fluorescent protein.

The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Expression vectors contain expression control sequences operatively linked to a polynucleotide sequence of interest, for example, that encodes a fluorescent protein variant, as indicated above. The expression vector can be adapted for function in prokaryotes or eukaryotes by inclusion of appropriate promoters, replication sequences, markers, and the like. An expression vector can be transfected into a recombinant host cell for expression of a fluorescent protein variant, and host cells can be selected, for example, for high levels of expression in order to obtain a large amount of isolated protein. A host cell can be maintained in cell culture, or can be a cell in vivo in an organism. A fluorescent protein variant can be produced by expression from a polynucleotide encoding the protein in a host cell such as *E. coli. Aequorea* GFP-related fluorescent proteins, for example, are best expressed by cells cultured between about 15° C. and 30° C., although higher temperatures such as 37° C. can be used. After synthesis, the fluorescent proteins are stable at higher temperatures and can be used in assays at such temperatures.

An expressed fluorescent protein variant, which can be a tandem dimer fluorescent protein or a non-oligomerizing monomer, can be operatively linked to a first polypeptide of interest, further can be linked to a second polypeptide of interest, for example, a peptide tag, which can be used to facilitate isolation of the fluorescent protein variant, including any other polypeptides linked thereto. For example, a polyhistidine tag containing, for example, six histidine residues, can be incorporated at the N-terminus or C-terminus of the fluorescent protein variant, which then can be isolated in a single step using nickel-chelate chromatography. Additional peptide tags, including a c-myc peptide, a FLAG epitope, or any ligand (or cognate receptor), including any peptide epitope (or antibody, or antigen binding fragment thereof, that specifically binds the epitope are well known in the art and similarly can be used. (see, for example, Hopp et al., Biotechnology 6:1204 (1988); U.S. Pat. No. 5,011,912, each of which is incorporated herein by reference).

Uses of Fluorescent Protein Variants

A fluorescent protein variant of the invention is useful in any method that employs a fluorescent protein. Thus, the fluorescent protein variants, including the monomeric, dimeric, and tandem dimer fluorescent proteins, are useful as fluorescent markers in the many ways fluorescent markers already are used, including, for example, coupling fluorescent protein variants to antibodies, polynucleotides or other receptors for use in detection assays such as immunoassays or hybridization assays, or to track the movement of proteins in cells. For intracellular tracking studies, a first (or other) polynucleotide encoding the fluorescent protein variant is fused to a second (or other) polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein. In one embodiment of this method, two proteins of interest independently are fused with two fluorescent protein variants that have different fluorescent characteristics.

The fluorescent protein variants of this invention are useful in systems to detect induction of transcription. For example, a nucleotide sequence encoding a non-oligomerizing monomeric, dimeric or tandem dimeric fluorescent protein can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

A fluorescent protein variant of the invention also is useful in applications involving FRET, which can detect events as a function of the movement of fluorescent donors and acceptors towards or away from each other. One or both of the donor/acceptor pair can be a fluorescent protein variant. Such a donor/acceptor pair provides a wide separation between the excitation and emission peaks of the donor, and provides good overlap between the donor emission spectrum and the acceptor excitation spectrum. Variant red fluorescent proteins or red-shifted mutants as disclosed herein are specifically disclosed as the acceptor in such a pair.

FRET can be used to detect cleavage of a substrate having the donor and acceptor coupled to the substrate on opposite sides of the cleavage site. Upon cleavage of the substrate, the donor/acceptor pair physically separate, eliminating FRET. Such an assay can be performed, for example, by contacting the substrate with a sample, and determining a qualitative or quantitative change in FRET (see, for example, U.S. Pat. No. 5,741,657, which is incorporated herein by reference). A fluorescent protein variant donor/acceptor pair also can be part of a fusion protein coupled by a peptide having a proteolytic cleavage site (see, for example, U.S. Pat. No. 5,981,200, which is incorporated herein by reference). FRET also can be used to detect changes in potential across a membrane. For example, a donor and acceptor can be placed on opposite sides of a membrane such that one translates across the membrane in response to a voltage change, thereby producing a measurable FRET (see, for example, U.S. Pat. No. 5,661,035, which is incorporated herein by reference).

In other embodiments, a fluorescent protein of the invention is useful for making fluorescent sensors for protein kinase and phosphatase activities or indicators for small ions and molecules such as $Ca^{2+}$, $Zn^{2+}$, cyclic 3',5'-adenosine monophosphate, and cyclic 3',5'-monophosphate.

Fluorescence in a sample generally is measured using a fluorimeter, wherein excitation radiation from an excitation source having a first wavelength, passes through excitation optics, which cause the excitation radiation to excite the sample. In response, a fluorescent protein variant in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, for example, Lakowicz, "Principles of Fluorescence Spectroscopy" (Plenum Press 1983); Herman, "Resonance energy transfer microscopy" In "Fluorescence Microscopy of Living Cells in Culture" Part B, Meth. Cell Biol. 30:219-243 (ed. Taylor and Wang; Academic Press 1989); Turro, "Modern Molecular Photochemistry" (Benjamin/Cummings Publ. Co., Inc. 1978), pp. 296-361, each of which is incorporated herein by reference).

Accordingly, the present invention provides a method for identifying the presence of a molecule in a sample. Such a method can be performed, for example, by linking a fluorescent protein variant of the invention to the molecule, and detecting fluorescence due to the fluorescent protein variant in a sample suspected of containing the molecule. The molecule to be detected can be a polypeptide, a polynucleotide, or any other molecule, including, for example, an antibody, an enzyme, or a receptor, and the fluorescent protein variant can be a tandem dimer fluorescent protein.

The sample to be examined can be any sample, including a biological sample, an environmental sample, or any other sample for which it is desired to determine whether a particular molecule is present therein. For example, the sample includes a cell or an extract thereof. The cell can be obtained from a vertebrate, including a mammal such as a human, or from an invertebrate, and can be a cell from a plant or an animal. The cell can be obtained from a culture of such cells, for example, a cell line, or can be isolated from an organism. As such, the cell can be contained in a tissue sample, which can be obtained from an organism by any means commonly used to obtain a tissue sample, for example, by biopsy of a human. Where the method is performed using an intact living cell or a freshly isolated tissue or organ sample, the presence of a molecule of interest in living cells can be identified, thus providing a means to determine, for example, the intracellular compartmenentalization of the molecule. The use of the fluorescent protein variants of the invention for such a purpose provides a substantial advantage in that the likelihood of aberrant identification or localization due to oligomerization the fluorescent protein is greatly minimized.

A fluorescent protein variant can be linked to the molecule directly or indirectly, using any linkage that is stable under the conditions to which the protein-molecule complex is to be exposed. Thus, the fluorescent protein and molecule can be linked via a chemical reaction between reactive groups present on the protein and molecule, or the linkage can be mediated by linker moiety, which contains reactive groups specific for the fluorescent protein and the molecule. It will be recognized that the appropriate conditions for linking the fluorescent protein variant and the molecule are selected depending, for example, on the chemical nature of the molecule and the type of linkage desired. Where the molecule of interest is a polypeptide, a convenient means for linking a fluorescent protein variant and the molecule is by expressing them as a fusion protein from a recombinant nucleic acid molecule, which comprises a polynucleotide encoding, for example, a tandem dimer fluorescent protein operatively linked to a polynucleotide encoding the polypeptide molecule.

A method of identifying an agent or condition that regulates the activity of an expression control sequence also is provided. Such a method can be performed, for example, by exposing a recombinant nucleic acid molecule, which includes a polynucleotide encoding a fluorescent protein variant operatively linked to an expression control sequence, to an agent or condition suspected of being able to regulate expression of a polynucleotide from the expression control sequence, and detecting fluorescence of the fluorescent protein variant due to such exposure. Such a method is useful, for example, for identifying chemical or biological agents, including cellular proteins, that can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The fluorescent protein variants of the invention also are useful in a method of identifying a specific interaction of a first molecule and a second molecule. Such a method can be performed, for example, by contacting the first molecule, which is linked to a donor first fluorescent protein variant, and the second molecule, which is linked to an acceptor second fluorescent protein variant, under conditions that allow a specific interaction of the first molecule and second molecule; exciting the donor; and detecting fluorescence or luminescence resonance energy transfer from the donor to the acceptor, thereby identifying a specific interaction of the first molecule and the second molecule. The conditions for such an interaction can be any conditions under which is expected or suspected that the molecules can specifically interact. In particular, where the molecules to be examined are cellular molecules, the conditions generally are physiological conditions. As such, the method can be performed in vitro using conditions of buffer, pH, ionic strength, and the like, that mimic physiological conditions, or the method can be performed in a cell or using a cell extract.

Luminescence resonance energy transfer entails energy transfer from a chemiluminescent, bioluminescent, lanthanide, or transition metal donor to the red fluorescent protein moiety. The longer wavelengths of excitation of red fluorescent proteins permit energy transfer from a greater variety of donors and over greater distances than possible with green fluorescent protein variants. Also, the longer wavelengths of emission is more efficiently detected by solid-state photodetectors and is particularly valuable for in vivo applications where red light penetrates tissue far better than shorter wavelengths. Chemiluminescent donors include but are not limited to luminol derivatives and peroxyoxalate systems. Bioluminescent donors include but are not limited to aequorin, obelin, firefly luciferase, *Renilla* luciferase, bacterial luciferase, and variants thereof. Lanthanide donors include but are not limited to terbium chelates containing ultraviolet-absorbing sensitizer chromophores linked to multiple liganding groups to shield the metal ion from solvent water. Transition metal donors include but are not limited to ruthenium and osmium chelates of oligopyridine ligands. Chemiluminescent and bioluminescent donors need no excitation light but are energized by addition of substrates, whereas the metal-based systems need excitation light but offer longer excited state lifetimes, facilitating time-gated detection to discriminate against unwanted background fluorescence and scattering.

The first and second molecules can be cellular proteins that are being investigated to determine whether the proteins specifically interact, or to confirm such an interaction. Such first and second cellular proteins can be the same, where they are being examined, for example, for an ability to oligomerize, or they can be different where the proteins are being examined as specific binding partners involved, for example, in an intracellular pathway. The first and second molecules also can be a polynucleotide and a polypeptide, for example, a polynucleotide known or to be examined for transcription regulatory element activity and a polypeptide known or being tested for transcription factor activity. For example, the first molecule can comprise a plurality of nucleotide sequences, which can be random or can be variants of a known sequence, that are to be tested for transcription regulatory element activity, and the second molecule can be a transcription factor, such a method being useful for identifying novel transcription regulatory elements having desirable activities.

The present invention also provides a method for determining whether a sample contains an enzyme. Such a method can be performed, for example, by contacting a sample with a tandem fluorescent protein variant of the invention; exciting the donor, and determining a fluorescence property in the sample, wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a tandem fluorescent protein variant construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

Also provided is a method for determining the pH of a sample. Such a method can be performed, for example, by contacting the sample with a first fluorescent protein variant, which can be a tandem dimer fluorescent protein, wherein the emission intensity of the first fluorescent protein variant changes as pH varies between pH 5 and pH 10; exciting the indicator; and determining the intensity of light emitted by the first fluorescent protein variant at a first wavelength, wherein the emission intensity of the first fluorescent protein variant indicates the pH of the sample. The first fluorescent protein variant useful in this method, or in any method of the invention, can comprise two DsRed monomers. It will be recognized that such fluorescent protein variants similarly are useful, either alone or in combination, for the variously disclosed methods of the invention.

The sample used in a method for determining the pH of a sample can be any sample, including, for example, a biological tissue sample, or a cell or a fraction thereof. In addition, the method can further include contacting the sample with a second fluorescent protein variant, wherein the emission intensity of the second fluorescent protein variant changes as pH varies from 5 to 10, and wherein the second fluorescent protein variant emits at a second wavelength that is distinct from the first wavelength; exciting the second fluorescent protein variant; determining the intensity of light emitted by the second fluorescent protein variant at the second wavelength; and comparing the fluorescence at the second wavelength to the fluorescence at the first wavelength. The first (or second) fluorescent protein variant can include a targeting sequence, for example, a cell compartmentalization domain such a domain that targets the fluorescent protein variant in a cell to the cytosol, the endoplasmic reticulum, the mitochondrial matrix, the chloroplast lumen, the medial trans-Golgi cisternae, a lumen of a lysosome, or a lumen of an endosome. For example, the cell compartmentalization domain can include amino acid residues 1 to 81 of human type II membrane-anchored protein galactosyltransferase, or amino acid residues 1 to 12 of the presequence of subunit IV of cytochrome c oxidase.

Detectable Labels Useful for the Invention

The detectable label useful according to the invention may be selected from the group consisting of radioactive, enzymatic, colorimetric, chemiluminescent, fluorescent, electrochemical labels and combinations thereof. In an exemplary embodiment of this aspect, the detectable label is a fluorescent compound. In an exemplary embodiment, the detectable label is selected from the group consisting of fluorescein, rhodamine, bodipy, cyanine, Alexa, Naphthofluorescein, Oregon Green, coumarin, dansyl, Texas Red, pyrene, Cascade Blue, and Alexa 350 and derivatives thereof. In certain embodiments, fluorescent proteins may be used. For example, green fluorescent proteins (GFPs) of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium* (Ward et al., 1982, Photochem. Photobiol. 35:803-808; Levine et al., 1982, Comp. Biochem. Physiol. 72B:77-85).

An exemplary fluorescent protein is green fluorescent protein (GFP) or a modified GFP. Wild-type GFP has long been used in the art. Starting from green fluorescent protein, many modified versions have been derived with altered or enhanced spectral properties as compared with wild-type GFP. See, e.g., U.S. Pat. No. 5,625,048; International Patent Publication WO 97/28261; International Patent Publication WO 96/23810. Useful are the modified GFPs W1B and TOPAZ, available commercially from Aurora Biosciences Corp., San Diego, Calif. W1B contains the following changes from the wild-type GFP sequence: F64L, S65T, Y66W7 N1461, M153T, and V163A (see Table 1, page 519, of Tsien, 1998, Ann. Rev. Biochem. 67:509-544). TOPAZ contains the following changes from the wild-type GFP sequence: S65G, V68L, S72A, and T203Y (see Table 1, page 519, of Tsien, 1998, Ann. Rev. Biochem. 67:509-544). Wild-type nucleotide and amino acid sequences of GFP are shown in FIG. 1 and SEQ ID NO: 1 of International Patent Publication WO 97/28261; in FIG. 1 of Tsien, 1998, Ann. Rev. Biochem. 67:509544; and in Prasher et al., 1992, Gene 111:229. Of particular interest in using fluorescent proteins in FRET-based screening assays are variants of the *A. Victoria* GFP known as Cyan FP (CFP, Donor (D)) and Yellow FP (YFP, Acceptor (A)). As an example, the YFP variant can be made as a fusion protein with, for example, a CKAP4 polypeptide. Vectors for the expression of GFP variants as fusions (Clontech) as well as flurophore-labeled compounds (Molecular Probes) are known in the art. When expressing GFPs in mammalian cells, it may be advantageous to construct versions of the GFPs having altered codons that conform to those—20 codons preferred by mammalian cells (Zolotukhin et al., J. Virol. 1996, 70:4646-46754; Yang et al., 1996, Nucl. Acids Res. 24:4592-4593). Another way of improving GFP expression in mammalian cells is to provide an optimal ribosome binding site by the use of an additional codon immediately after the starting methionine (Crarneli et al., 1996, Nature Biotechnology 14:315-319).

Kits of the Invention

The present invention also provides kits to facilitate and/or standardize use of compositions provided by the present invention, as well as facilitate the methods of the present invention. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., polypeptides or polynucleotides) as well as other components. In addition, kits of the present invention can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid.

In some embodiments, for example, kits of the present invention can provide a fluorescent protein of the invention, a polynucleotide vector (e.g., a plasmid) encoding a fluorescent protein of the invention, bacterial cell strains suitable for propagating the vector, and reagents for purification of expressed fusion proteins.

A kit can contain one or more compositions of the invention, for example, one or a plurality of fluorescent protein variants, which can be a portion of a fusion protein, or one or a plurality of polynucleotides that encode the polypeptides. The fluorescent protein variant can be a mutated fluorescent protein having a reduced propensity to oligomerize, such as a non-oligomerizing monomer, or can be a tandem dimer fluorescent protein and, where the kit comprises a plurality of fluorescent protein variants, the plurality can be a plurality of the mutated fluorescent protein variants, or of the tandem dimer fluorescent proteins, or a combination thereof.

A kit of the invention also can contain one or a plurality of recombinant nucleic acid molecules, which encode, in part, fluorescent protein variants, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions of the invention that are contained in the kit.

Such kits can be particularly useful where they provide a plurality of different fluorescent protein variants because the artisan can conveniently select one or more proteins having the fluorescent properties desired for a particular application. Similarly, a kit containing a plurality of polynucleotides encoding different fluorescent protein variants provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest or, if desired, for operatively linking two or more the polynucleotides encoding the fluorescent protein variants to each other.

Antibodies and Antibody Compositions

Additionally, the present invention includes a purified antibody produced in response to immunization with CKAP4, APF and/or DHHC2, as well as compositions comprising this purified antibody. Antibodies refer to single chain, two-chain, and multi-chain proteins and glycoproteins belonging to the classes of polyclonal, monoclonal, chimeric, and hetero immunoglobulins; it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes. A humanized antibody is an antibody derived from a non-human antibody, typically murine, that retains or substantially retains the antigen-binding properties of the parent antibody but which is less immunogenic in humans, U.S. Pat. No. 5,530,101, incorporated herein by reference in its entirety.

An antibody composition of the present invention is typically produced by immunizing a laboratory mammal with an inoculum of the present invention and to thereby induce in the mammal antibody molecules having the appropriate polypeptide immunospecificity. The polyclonal antibody molecules are then collected from the mammal and isolated to the extent desired by well known techniques such as, for example, by immunoaffinity chromatography. The antibody composition so produced can be used in, inter alia, the diagnostic methods and systems of the present invention to detect CKAP4, APF and/or DHHC2 in a sample.

Monoclonal antibody compositions are also contemplated by the present invention. A monoclonal antibody composition contains, within detectable limits, only one species of antibody combining site capable of effectively binding CKAP4, APF and/or DHHC2. Thus, a monoclonal antibody composition of the present invention typically displays a single binding affinity for CKAP4, APF and/or DHHC2 even though it may contain antibodies capable of binding proteins other than CKAP4, APF and/or DHHC2. Suitable antibodies in monoclonal form, typically whole antibodies, can also be prepared using hybridoma technology described by Niman et al., Proc. Natl. Sci., U.S.A., 80:4949-4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

The antibody compositions produced by the above method can be used, for example, in diagnostic and therapeutic modalities wherein formation of an CKAP4, APF and/or DHHC2-containing immunoreaction product is desired.

The invention also provides the use of an antibody specific for an APF polypeptide for the treatment of a CKAP4-related disease or disorder. The invention also provides the use of an antibody specific for a CKAP4 polypeptide for the treatment of an APF-related disease or disorder.

Antibodies may be raised which bind to an APF polypeptide, a CKAP4 polypeptide, and/or a DHCC2 polypeptide. Antibodies may be raised which bind to both an APF polypeptide and a CKAP4 polypeptide. Antibodies may be raised against APF fusion proteins such as Met-APF. Typically, the antibody "specifically binds" or "is specific for" an APF polypeptide, a CKAP4 polypeptide, and/or a DHCC2 polypeptide. The antibody may bind to a glycosylation site on an APF polypeptide, a CKAP4 polypeptide, and/or a DHCC2 polypeptide. An antibody, or other compound, "specifically binds" to a polypeptide or is "specific for" a polypeptide when it binds with preferential affinity to the protein for which it is specific compared to other polypeptides, such as chemokine or G-protein receptor. A variety of protocols for competitive binding or immunoradiometric assays to determine the specific binding capability of an antibody are well known in the art (see for example Maddox et al., J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments which bind a polypeptide. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising an antibody in a host animal against the whole polypeptide or a fragment thereof, for example an antigenic epitope thereof, herein after the "immunogen". The fragment may be any of the fragments mentioned herein (typically at least 10 or at least 15 amino acids long) and comprise a polymorphism (such as any of the polymorphisms mentioned herein).

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) Nature 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

ELISA

The present invention also contemplates the direct measurements of protein expression, such as for example, reporter expression, levels in assays. These include the direct measurement of protein expression using methods such as ELISA, radioimmunoassay, gel electrophoresis or western blotting, and immunohistochemistry.

ELISA techniques are well-known in the art (see, e.g., Kenney, et al., J. Immunol. 138:4236 (1987), which is incorporated herein by reference; and Harlow, supra). The ELISA protocol involves coating the wells of microtiter (ELISA) plates with a monoclonal or polyclonal antibody directed to the protein of interest, e.g., an anti-TNF antibody, at a concentration of between about 0.5-15 µg/ml. The antibody solution is allowed to incubate in the wells for about 12-24 hours at 4.degree. C. in a humid atmosphere. The unbound antibody is washed away, and the open sites are blocked with an inert protein, such as bovine serum albumin (BSA) in PBS, which is allowed to incubate in the wells for 1-3 hours. The blocking solution is discarded and about 50 μl of the sample keratinocyte supernatant, obtained from the cell pellet of keratinocytes after centrifugation as described above, is added to the ELISA wells. For quantitation the sample solution is serially diluted in PBS buffer. After an incubation period, typically one to five hours at 37° C., preferably one to two hours, more preferably one hour, or about 12 hours at 4° C., the plates are again washed and the second antibody directed to the protein, e.g., a polyclonal rabbit anti-TNF antibody, is applied. After an incubation period, typically one to five hours, or for example one to two hours, or for example one hour, the plates are again washed. A biotin-labeled third antibody, directed against the second antibody, is added (e.g., goat anti-rabbit) and incubated for about 0.5-1 hour at 37° C. After washing the unbound material, horseradish peroxidase-labeled streptavidin is added and incubated for 0.5-1 hour at 37° C. Because the protein is situated between two layers of antibodies, this type of assay is often called a sandwich ELISA. Subsequent steps using an o-phenylene diamine (OPD) substrate (e.g. 1 mg/mL OPD/0.3% H2O2/0.1 M citrate buffer) permit color development, with the intensity of color varying according to the amount of TNF specifically bound. Alternatively, the second enzyme may be biotinylated to eliminate the need for a third antibody. Other methods of assay will be apparent to those of skill in the art. The ELISAs for human and murine TNF are quite sensitive, reliably detecting protein concentrations of less than 50 pg/mL.

Radioimmunoassay

Radioimmunoassay may also be used to quantitate the production of proteins in a manner similar to that just described for quantitation by ELISA. Generally, a first protein specific antibody is attached to a substrate using standard techniques, such as those described in Harlow or Sambrook, et al., MOLECULAR CLONING: A LABORATORY MANUAL (Cold Spring Harbor 1989), which is incorporated herein by reference. The bound antibody is then exposed to the supernatant taken from keratinocytes cultured with a putative skin anti-inflammatory substance. A second antibody, carrying a radioactive label such as $_{125}$I-modified tyrosine is added to the bound protein and allowed to incubate as described above. Typically the labelled antibody has a specific activity of about 5×106 cpm/μg. The unbound labelled material is washed away and the remaining label quantitated, using standard techniques, e.g., a scintillation counter.

Gel Electrophoresis and Western Blotting

As an alternative, the presence of proteins can be assessed by Western blot analysis (see, e.g., Didierjean, et al., J. Invest. Dermatol. 92:809 (1989), which is incorporated herein by reference). In addition, Western blot analysis can be used to analyze samples that cannot be accurately tested in the ELISAs and the WEHI assay (below) due to high protein concentration or the presence of various detergents or solubilizing agents.

Generally, this procedure involves electrophoresing the cell supernatant samples on reducing or non-reducing SDS-polyacrylamide gels using standard techniques such as those described in Sambrook. The separated protein in the gel is electrophoretically blotted onto a nitrocellulose membrane, nylon membrane or some other suitable support, again using common techniques. This membrane is first blocked with an inert protein, then incubated with a solution containing an antibody to the protein of interest, such as one of the antibodies described above, to bind to the immobilized protein. In an exemplary embodiment the first antibody is a monoclonal antibody which has been raised against the denatured protein or a high-titer polyclonal antiserum. The bound protein-antibody complex is subsequently incubated with a second labelled antibody specific for the first antibody to form a protein-antibody-antibody complex. For example, the second labelled antibody may be labelled with a colorimetric label, e.g., biotin or horseradish peroxidase, or the antibody may be radiolabelled, e.g., with $^{125}$I, $^{35}$S or $^{32}$P. The bound antibody-protein complex is then assayed using the method appropriate for the label as described above. Of course, one of skill in the art will recognize that the protein may be purified and identified merely by separation on a suitable gel, such as sodium dodecylsulfate (SDS) gel if the amount of protein in the sample is sufficiently large.

Immunohistochemistry

Similar to Western blotting, immunohistochemistry provides information of a qualitative and quantitative nature. The strength of this procedure is that it allows visualization and localization of the distribution of a specific protein among various cell types or within different regions of a tissue (see, e.g., Griffiths, et al., Br. J. Dermatol. 124:519 (1991), which is incorporated herein by reference). In performing this procedure, tissue samples are flash frozen in an embedding compound, e.g., Tissue-Tek OCT (available commercially from Miles, Inc., Elkhart, Ind.), and stored at −70° C. until used. The tissue is then cut into sections, typically 6 □m sections, and placed on microscope slides. The sequence of steps that follow are quite similar to the procedure involved in the development of a Western blot. After fixing the tissue in acetone, the slides are incubated with serum, typically goat serum, to block nonspecific binding sites. The samples are subsequently incubated with a specific antibody directed against the protein of interest. After thorough washing, a second, labelled antibody, e.g., a biotinylated antibody, is added and the amount of bound label is quantitated using standard techniques. For example, when a biotinylated antibody is used, avidin conjugated with biotinylated horse radish peroxidase is added, followed by incubation with a chromogenic peroxidase substrate, to initiate a colorimetric reaction. The sample is then counterstained with hematoxylin. The presence of chromogen, the color of which will depend on the particular substrate being used, is indicative of the presence of the protein of interest. Care must by taken, however, to ensure that the staining pattern is specific. A control antibody is used for comparison with the anti-protein antibody. Untreated control tissue or cells are also compared to tissues or cells that have been subjected to an inflammatory stimulus.

Diagnostic Assays

It is envisioned that an in vitro diagnostic test strip based on the principles of ligand-receptor affinity and immunochromatography will be used to rapidly and accurately identify APF in the urine of patients. The name most commonly used to describe this type of "dipstick" assay format is "lateral flow".

Most lateral flow test strips such as these are modeled after existing immunoassay formats which are typically "sandwich" assays in which molecules of interest are analyzed by competitive or inhibition assays. Many variations are possible, but they all have in common the formation of a complex between a particle that is free in the sample stream and a capture reagent that is bound to a membrane at the test line.

While formation of an immunocomplex at the test line is most commonly used as the result indicator, it is theoretically possible to achieve a result using any ligand recognition system where a detector particle becomes bridged to a capture reagent on the membrane. The EC50 for APF is very low nanomolar, indicating an affinity for the receptor, CKAP4 that is equivalent to that which occurs in antigen antibody interactions. Given this high affinity, CKAP4 or a portion thereof may be used as the capture reagent for APF in a manner analogous to anti-hCG antibodies being the capture reagent for hCG in a lateral flow, dipstick-style pregnancy test.

Various types of detector reagents can be used for the visualization of a signal. The most commonly used materials in commercially available tests are latex beads and colloidal gold particles. Other possibilities include enzyme conjugates, other colloidal metals, dye sacs, fluorescent particles, and magnetic particles.

Based on current technology, it is envisioned that a lateral flow, dipstick-style APF detection system can be used simply as a "Yes/No" indicator or to quantify the abundance of APF in urine. It is envisioned that a lateral flow, dipstick-style detection system for APF will be utilized as an over-the-counter and as a point-of-care (physician's office or hospital) options for patients who suspect they may have IC.

The presence, level, expression, or activity of, for example, an APF polypeptide, a CKAP4 polypeptide, and/or a DHCC2 polypeptide can be evaluated in a variety of ways well known in the art, such as immunoassay, e.g., immunoprecipitation, Western blot analysis (immunoblotting), ELISA, fluorescence-activated cell sorting (FACS), and bead-based detection assays, such as the Luminex® detection technology provided by the MultiAnalyte Profiling Kit (Luminex Corporation, Austin, Tex.). Typically, the level of protein and/or activity, e.g., an APF polypeptide, a CKAP4 polypeptide, and/or a DHCC2 polypeptide or activity, in a subject sample is compared to the level and/or activity in a control, e.g., the level and/or activity in a tissue from a non-disease subject.

Various types of immunoassays are known in the art. One example of an immunoassay is a "sandwich" type assay, in which a target analyte(s) such as an APF polypeptide, a CKAP4 polypeptide, and/or a DHCC2 polypeptide is "sandwiched" between a labeled antibody and an antibody immobilized onto a solid support. The assay is read by observing the presence and amount of antigen-labeled antibody complex bound to the immobilized antibody. Another immunoassay useful in the methods and kits described herein is a "competition" type immunoassay, wherein an antibody bound to a solid surface is contacted with a sample (e.g., a fluid sample) containing both an unknown quantity of antigen analyte and with labeled antigen of the same type. The amount of labeled antigen bound on the solid surface is then determined to provide an indirect measure of the amount of antigen analyte in the sample. Such immunoassays are readily performed in a "dipstick" or other test device format (e.g., a flow-through or migratory dipstick or other test device design) for convenient use, e.g., home use or use by a health care provider. For example, numerous types of dipstick immunoassays assays are described in U.S. Pat. No. 5,656,448.

A test device, e.g., a "dipstick", refers to a substrate, preferably a substrate that is insoluble in aqueous solution, e.g., a fluid sample, onto which an agent described herein, e.g., an agent that detects a protein described herein, e.g., an antibody described herein, is immobilized. The agent can be applied as a layer on the substrate, or can also penetrate into the substrate. A test device can be a substrate, e.g., a membrane, e.g., a membrane strip, onto which an agent described herein is immobilized. A test device can include a housing for the substrate, e.g., a membrane, e.g., a membrane strip, onto which an agent described herein is immobilized. In one embodiment, the substrate is a substrate other than glass, and is preferably flexible.

In one embodiment, the substrate, e.g., the membrane, e.g., the membrane strip, is, e.g., between about 0.1 and 0.5 inches in width, e.g., between about 0.2 and 0.4, e.g., between about 0.25 and 0.3 inches in width, and is, e.g., between about 1 and 4 inches in length, e.g., between about 2 and 3 inches in length. In one embodiment, an agent described herein, e.g., an antibody described herein, covers an area of the substrate, e.g., the membrane, e.g., the membrane strip, that is greater than about 0.01 cm2, e.g., greater than about 0.1, 0.5, or 1 cm2.

In one embodiment, the test device includes a marker indicating how far to "dip" the substrate into a biological sample, e.g., a fluid sample.

In one embodiment, a method described herein employs a dipstick or other test device format to measure the presence, level, expression or activity of a protein described herein, e.g., an APF polypeptide, a CKAP4 polypeptide, and/or a DHCC2 polypeptide. A dipstick or other test device assay can, for example, provide a color indication of, or an increased risk for, interstitial cystitis based upon the levels of a protein described herein, such as an APF polypeptide, a CKAP4 polypeptide, and/or a DHCC2 polypeptide, in a sample, e.g., a fluid sample. In one scenario, the dipstick or other test device can react to produce one color if a level of a first protein is exceeded, a different color if a level of a second protein is exceeded, a third color if a level of a third protein is exceeded, and when three levels are exceeded, the three colors will combine to yield a separate color that is easily distinguishable from the others. A dipstick or other test device-based assay optionally includes an internal negative or positive control.

A dipstick or other test device-based assay could find use in a clinical setting by quickly and reliably serve as an indication of, or indicating a heightened risk for interstitial cystitis. This could save valuable time by allowing the physician to initiate treatment sooner, thereby minimizing the harmful effects of the disease.

In another embodiment, the method of the present invention may be utilized in combination with a densitometer or generally a device for measuring light intensity, transmittance, reflection or refraction, or for measuring the wavelength of light as a measure of assay result. Such a device can be used in a setting such as a doctor's office, a clinic or a hospital. The densitometer or other device can provide rapid measurement of the optical density of dipstick or other test device strips that have been contacted with a bodily fluid or tissue.

In a preferred embodiment, a change in color, density, or other parameter can be read by the naked eye.

In a preferred embodiment, the assay can be read without the addition of a reagent not already on the substrate.

Another possible approach to a diagnostic assay includes the use of electrochemical sensor strips, such as those used for home glucose testing, onto which a sample is placed, and which strips include reagents for initiating a reaction when wetted by the sample. The sensor strip is inserted into a meter that measures, e.g., diffusion-limited current of a reaction species indicative of the analyte of interest, such as an APF polypeptide, a CKAP4 polypeptide, and/or a DHCC2 polypeptide. The meter then yields a display indicative of the concentration of analyte in the sample.

Tom et al., U.S. Pat. No. 4,366,241, and Zuk, EP-A 0 143 574 describe migration type assays in which a membrane is impregnated with the reagents needed to perform the assay. An analyte detection zone is provided in which labeled analyte is bound and assay indicia are read.

Bernstein, U.S. Pat. No. 4,770,853, May et al., WO 88/08534, and Ching et al., EP-A 0 299 428 describe migration assay devices that incorporate within them reagents that have been attached to colored direct labels, thereby permitting visible detection of the assay results without addition of further substances.

Valkirs et al., U.S. Pat. No. 4,632,901, disclose a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane that acts as a reagent delivery system.

Baxter et al., EP-A 0 125 118, disclose a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products that either deposit as a precipitate onto the solid phase or produce a visible color change in the substrate solution.

Kali et al., EP-A 0 282 192, disclose a dipstick device for use in competition type assays.

Rounds in U.S. Pat. No. 4,786,589 describes a dipstick immunoassay device in which the antibodies have been labeled with formazan.

Detection Device and Kits

In another aspect, a kit is provided for detecting an APF polypeptide, a CKAP4 polypeptide, and/or a DHCC2 polypeptide in a fluid sample, e.g. urine. In some embodiments, the kit comprises a housing having a chamber consisting of one or more test wells disposed inside the housing and having an inlet above each well to allow the introduction of the fluid samples. Each test well may contain the detection reagents, such as, for example, antibodies, for, for example an APF polypeptide, a CKAP4 polypeptide, and/or a DHCC2 polypeptide.

The housing may be at least partially transparent, or may have windows provided therein, for observation of an indicator region that undergoes a color or fluorescence change. The kit may be designed to contain a dipstick, a lateral flow device, or migration-type device. Preferably, the instant device is a dipstick as described in the International Patent Application Publication WO/2002/033413. In other embodiments, the device is a lateral flow device of the type disclosed, for example, in U.S. Pat. Nos. 7,297,529; 7,344,893; and 7,090,803.

Typically, a lateral flow device may comprise a housing having an inlet for the sample and side walls defining a fluid lateral flow path extending from the inlet. By "lateral flow", it is meant liquid flow in which the dissolved or dispersed components of the sample are carried, suitably at substantially equal rates, and with relatively unimpaired flow, laterally through the carrier. Preferably, the fluid flow path contains one or more porous carrier materials that are hydrophilic, but preferably do not absorb water. Suitable examples include, but are not limited to, paper, cellulose, nitrocelloluse, pressed fibers, including glass fibers, sintered glass, ceramic or plastic materials, such as nylon, polyethylene or polyester. The porous carrier materials may be in fluid communication along substantially the whole fluid flow path so as to assist transfer of fluid along the path by capillary action. The porous carrier materials may function as solid substrates for attachment of reagents or indicator moieties. In some embodiment, the device may have a control substance that interacts with the sample of the fluid to improve the accuracy of the test.

The size and shape of the carrier are not critical and may vary. The carrier defines a lateral flow path and may be presented in the form of one or more elongated strips or columns. In certain embodiments, the porous carrier is one or more elongated strips of sheet material, or a plurality of sheets making up in combination an elongate strip. One or more reaction zones and detection zones would then normally be spaced apart along the long axis of the strip. However, in some embodiments the porous carrier could, for example be in other sheet forms, such as a disk. In these cases the reaction zones and detection zones would normally be arranged concentrically around the center of the sheet, with a sample application zone in the center of the sheet. In yet other embodiments, the carrier is formed of carrier beads, for example beads made from any of the materials described above. The beads may suitably be sized from about 1 micrometer to about 1 mm. The beads may be packed into the flow path inside the housing, or may be captured or supported on a suitable porous substrate such as a glass fiber pad.

It will be appreciated that the devices in the apparatus according to the present invention may be adapted to detect more than one marker. This can be done by the use of several different reagents in a single reaction zone, or suitably by the provision in a single device of a plurality of lateral flow paths each adapted for detecting a different analyte. In certain embodiments, the plurality of lateral flow paths are defined as separate fluid flow paths in the housing, for example the plurality of lateral flow paths may be radially distributed around a sample receiving port. In other embodiments, the plurality of fluid flow paths are physically separated by the housing. In yet other embodiments, multiple lateral flow paths (lanes) can be defined in a single lateral flow membrane by depositing lines of wax or similar hydrophobic material between the lanes.

An absorbent element may also be included in the instant devices. The absorbent element is a means for drawing the whole sample through the device by capillary attraction. Generally, the absorbent element will consist of a hydrophilic absorbent material such as a woven or nonwoven textile material, a filter paper or a glass fiber filter.

The device may further comprise at least one filtration element to remove impurities from the sample before the sample undergoes analysis. The filtration device may for example comprise a microporous filtration sheet for removal of cells and other particulate debris from the sample. The filtration device is typically provided upstream of the sample application zone of the fluid flow path, for example in the inlet of the housing or in the housing upstream of the inlet.

In certain embodiments, the instant devices may also include a control moiety in a control zone of the device, wherein the control moiety can interact with a component of the fluid sample to improve the accuracy of the device. Suitably, the control zone is adapted to reduce false positive or false negative results. A false negative result could arise for various reasons, including (1) the sample is too dilute, or (2) the sample was too small to start with. In order to address false negative mechanism, the control zone may further comprise a reference assay element for determining the total analyte content of the sample, that is to say for establishing that the total analyte content or the total protein content of the sample is higher than a predetermined minimum. It is possible to indicate the presence of protein by the use of tetrabromophenol blue, which changes from colorless to blue depending on the concentration of protein present.

In addition, the instant device may further comprise a sampling device for collecting a sample of a fluid. To that end, the instant device may include a connector for attaching a needle to the device and a plunger for extracting a sample of fluid from the body of the patient through the needle into the housing of the device. Additional elements of the instant device may include, but are not limited to, a color chart for interpreting the output of the diagnostic device, a wash liquid for carrying a sample of fluid through the device, and a pretreatment solution containing a reagent for pretreatment of the fluid sample.

In another embodiment, the kit includes a syringe for obtaining a sample of fluid wherein, the barrel of the syringe is coated with a mix of detection reagents and an appropriate carrier such that the detection occurs in the barrel once the sample of fluid is drawn or within the time necessary for the detection reagents to react with, e.g. an APF polypeptide, a CKAP4 polypeptide, and/or a DHCC2 polypeptide.

The invention also includes kits for detecting the presence of a protein described herein, e.g., an APF polypeptide, a CKAP4 polypeptide, and/or a DHCC2 polypeptide, in a biological sample. For example, the kit can include a compound or agent capable of detecting protein (e.g., an antibody) or mRNA (e.g., a nucleic acid probe) of a protein described herein in a biological sample; and a standard. The agent can be coupled to a detectable label, such as a colored, absorbent or fluorescent label. The kit can also include a positive and a negative control, e.g., a reagent that contains a protein described herein, e.g., an APF polypeptide, a CKAP4 polypeptide, and/or a DHCC2 polypeptide.

The compound or agent can be packaged in a suitable container. The kit can further comprise instructions for using the kit to evaluate a subject, e.g., for an APF polypeptide, a CKAP4 polypeptide, and/or a DHCC2 polypeptide.

Another embodiment of the present invention is a dipstick or other test device-based kit, suitable for home testing. Such a screening test would provide convenience, privacy and eliminate the necessity and cost of visiting a physician for a screening test, although the dipstick or other test device kit could also be used in a clinical setting. The dipstick or other test device kit could be similar to a home pregnancy kit, known to those of skill in the art, and could provide a color indication of, or an increased risk for, interstitial cystitis based upon the levels of a protein described herein, e.g., an APF polypeptide, a CKAP4 polypeptide, and/or a DHCC2 polypeptide, in the sample. Such a dipstick or other test device-based kit could be provided with a small plastic cup for collecting and retaining the sample and for conducting the test. In one scenario, the dipstick or other test device can react to produce one color if a level of a first protein, a different color if a level of a second protein is exceeded, and when both levels are exceeded, the two colors will combine to yield a third color that is easily distinguishable from the others.

In one embodiment, the kit includes at least 1, e.g., at least 2, 5, 10, 20, 30, or 50, test devices, e.g., dipsticks, e.g., membranes, e.g., membrane strips described herein. In one embodiment, the kit contains a container suitable for collecting a fluid sample.

A dipstick or other test device-based assay, similar to that described above, could find use in a clinical setting by quickly and reliably provide an indication of, or an increased risk for, interstitial cystitis. This could save valuable time by allowing the physician to initiate treatment sooner, thereby minimizing the harmful effects of the disease.

In another embodiment, the method of the present invention may be utilized in combination with a densitometer in a device for use in a setting such as a doctor's office, a clinic or a hospital. The densitometer can provide rapid measurement of the optical density of dipstick or other test device strips that have been contacted with a bodily fluid or tissue.

Other possible approaches include the use of electrochemical sensor strips, such as those used for home glucose testing, onto which a sample is placed, and which strips include reagents for initiating a reaction when wetted by the sample. The sensor strip is inserted into a meter that measures, e.g., diffusion-limited current of a reaction species indicative of the analyte of interest, e.g., an APF polypeptide, a CKAP4 polypeptide, and/or a DHCC2 polypeptide. The meter then yields a display indicative of the concentration of analyte in the sample.

The kit can also contain a device to obtain a tissue sample, such as a cotton swab or wooden swab.

Palmitoylation Assay

Palmitoylation can be measured according to any method known to those skilled in the art. For example, the incorporation of $^3$H-palmitate into acid-precipitable protein can be used to monitor palmitoylation. Trichloroacetic acid (TCA) precipitation, followed by scintillation counting as a means of measuring covalent protein modification, is well known to those of skill in the art.

In another approach, the fluorescence-based assay described by Varner et al. (2002) can be used. The assay described by Varner et al. uses a myristoylated peptide substrate, Myr-Gly-Cys, termed Myr-GCK, that mimics the palmitoylation substrate at the N-terminus of the non-receptor Src family kinases. The Myr-GCK substrate peptide and its synthesis are described by Creaser & Peterson, 2002, J. Am. Chem. Soc. 124: 2444-2445, which is incorporated herein by reference. The structure of the Myr-GCK substrate peptide, labeled with the NBD fluorophore NBD (7-nitrobenz-2-oxa-1,3-diazol-4-yl, available from Molecular Probes, Inc., Eugene, Oreg.) is as follows:

To perform the palmitoylation assay, Myr-GCK (10.mu.M) fluorescently labeled with NBD is incubated for 8 minutes at 37° C. with 50 μg of protein from a cellular membrane or pellet fraction containing palmitoyl acyltransferase (see below), in acylation buffer (50 mM citrate, 50 mM phosphate, 50 mM Tris, 50 mM CAPS at pH 7.2) in a total volume of 100 μl. Palmitoyl CoA (20 μM) is then added and the mixture is incubated at 37° C. for an additional 7.5 minutes. The assay is stopped by extraction in 1.2 ml of $CH_2Cl_2$:methanol:water (2:1:1). The organic fraction is dried under $N_2$, and then analyzed by HPLC as described below.

Dried assay extracts are dissolved in 25 ml of DMSO and resolved on a reverse-phase, wide pore butyl (5 μM, 300 Å, 4.6×0.250 mm) HPLC column using an acetonitrile gradient with a flow rate of 1 ml/min. Initially, the mobile phase is maintained as water/50% $CH_3CN$/0.1% TFA for 5 minutes, followed by a 5 minute linear gradient from 50% to 100% acetonitrile. The mobile phase is then maintained at 100% acetonitrile for 10 minutes, followed by a linear gradient from 100% to 50% acetonitrile over 5 minutes. NBD-label is detected by fluorescence at 531 nm upon excitation at 465 nm. The percentage of palmitoylated peptide in the sample is calculated by dividing the peak area corresponding to the palmitate-modified peptide by the total peak area corresponding to both palmitoylated and un-palmitoylated peptides.

Cell fractions containing palmitoyl acyltransferase for use in the palmitoylation assay described above are prepared according to the method of Smith et al. (1995, Mol Pharm 47, 24 1-247), essentially as follows: Cultured cells (e.g., HepG2 or MCF-7) are grown to about 70% confluence in 150 mm tissue culture dishes and collected by centrifugation. Cells are swollen with a buffer containing 10 mM HEPES (pH 7.4), 10 mM KCl, 1.5 mM $MgCl_2$, and 5 µM PMSF for 30 minutes on ice. The cells are disrupted by homogenization and centrifuged at 5,500 g for 10 minutes at 4° C. to remove nuclei and debris. (The nuclei and debris pellet can be assayed as the pellet fraction.) The supernatant from this spin is then ultracentrifuged at 100,000 g for 1 hour at 4° C. The pellet from this centrifugation is resuspended in 1000 of lysis buffer and collected as the membrane fraction. The supernatant is collected as the cytosolic fraction. Protein concentrations for each fraction are determined (e.g., using a fluorescamine assay, Bohlen et al., 1973, Arch Biochem Biophys 155, 213-220).

Methods of Diagnosis

The invention further provides methods of diagnosing a CKAP4-related disease or disorder or an APF-related disease or disorder in an individual, such as IC/PBS. A CKAP4- or APF-related disease or disorder is typically a disease or disorder is for example, IC/PBS.

In a diagnostic embodiment the invention, the method of diagnosis comprises contacting a sample isolated from an individual which comprises a CKAP4 peptide with an APF polypeptide under conditions which permit the binding of the APF polypeptide to the CKAP4 polypeptide. The activity of the CKAP4 polypeptide is then measured. The activity of this CKAP4 polypeptide is then compared with a standard and a difference in the activity relative to the standard indicative of the presence of a CKAP4-related disease or disorder in the individual. This standard refers to the equivalent measurement in an individual not affected by the CKAP4-relevant disease or disorder.

The methods of the diagnostic embodiment also comprise contacting a 5 sample isolated from an individual which comprises a APF polypeptide with a CKAP4 polypeptide under conditions which permit the binding of the APF polypeptide to the CKAP4 polypeptide. The activity of the CKAP4 polypeptide is then measured. The activity of this CKAP4 polypeptide is then compared with a standard and a difference in the activity relative to the standard indicative of the presence of a APF-related disease or disorder in the individual. This standard refers to the equivalent measurement in an individual not affected by the APF-relevant disease or disorder.

The conditions which permit the binding of a APF polypeptide to a CKAP4 polypeptide are, for example, the temperature, salt concentration, pH and protein concentration under which a APF polypeptide binds to a CKAP4 polypeptide. Exact binding conditions will vary depending on nature of the assay, for example, when the assay uses viable cells or only membrane fraction of cells. However, because CKAP4 is a cell surface receptor and APF polypeptides are secreted polypeptides that interact with the extracellular domain of CKAP4, conditions will generally include physiological salt concentration (approx 90 mM) pH about (7.0 to 8.0). Temperatures for binding may vary from 4° C. through to 37° C., but is preferably 4° C. The concentration of the APF polypeptide will also vary, but will for example be from about 0.1 pM to about 10 µM.

The methods of the diagnostic embodiments may be, for example, carried out in vitro on a sample from the individual. The sample typically comprises a body fluid and/or cells of the individual. The sample may be a blood, urine, saliva, skin, cheek cell or hair root sample. The sample is preferably a urine sample. The sample may be processed before the method is carried out, for example DNA extraction may be carried out, cells may be cultured or a membrane faction may be prepared from cells. The polynucleotide or protein in the sample may be cleaved either physically or chemically (e.g. using a suitable enzyme). In one embodiment the part of polynucleotide in the sample is copied (or amplified), e.g. by cloning or using a PCR based method prior to determining the presence of mutations or polymorphisms.

Diagnostic Use

In another embodiment of the present invention, measurement of CKAP4, APF and/or DHHC2, or proteins which are immunologically related to CKAP4, APF and/or DHHC2, can be used to detect and/or stage a disease or disorder in a subject. The measured amount may be compared to a baseline level. This baseline level can be the amount which is established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease, or from individuals not afflicted with the disease or condition.

The present invention also provides for the detection or diagnosis of disease or the monitoring of treatment by measuring the amounts of CKAP4, APF and/or DHHC2 transcript or peptide in a sample before and after treatment, and comparing the two measurements. The change in the levels of the markers relative to one another can be an improved prognostic indicator. A comparison of the amounts of a total marker with the amount of intra-cytoplasmic marker or membrane-bound marker is also envisioned.

The present invention provides a method for monitoring the effect of a therapeutic treatment on a subject who has undergone the therapeutic treatment. This method comprises measuring at suitable time intervals the amount of a soluble molecule or soluble fragment thereof, or the amount of CKAP4, APF and/or DHHC2 or fragment thereof. Any change or absence of change in the amount of the soluble molecule or in the amount of the CKAP4, APF and/or DHHC2 can be identified and correlated with the effect of the treatment on the subject. In a specific embodiment of the invention, soluble molecules immunologically related to CKAP4, APF and/or DHHC2 can be measured in the serum of patients by a sandwich enzyme immunoassay (for an example) in order to predict disease prognosis, for example, in viral infections, inflammation, autoimmune diseases, and tumors, or to monitor the effectiveness of treatments such as anti-viral administration.

FRET-Based Screening Methods

The physical proximity of the two fluorescent proteins results in increased fluorescence resonance energy transfer, which can be detected using fluorescent methods, including FRET microscopy, ratio imaging, or ratiometric fluorimetry. An instrument such as FLIPR™ can be set to alternate between reading signals at two different wavelengths with a cycling time of about one second, and is therefore extremely useful in measuring samples in high-throughput.

Fluorescence resonance energy transfer (FRET) is a non-radiative process whereby energy from a fluorescent donor molecule is transferred to an acceptor molecule without the involvement of a photon. Excitation of the donor molecule enhances the fluorescence emission of the longer-wavelength acceptor molecule (i.e., sensitized acceptor emission). The quantum yield of the donor fluorescence emission is concomitantly diminished. FRET has become a valuable tool for microscopy, because the efficiency of energy transfer has a strong inverse dependence on the distance between the donor and acceptor molecules. Thus, the appearance of FRET is a highly specific indicator of the proximity of the two molecules. This has led to the use of FRET efficiency as a "spectroscopic ruler" to measure molecular distances.

The recent availability of green fluorescent protein (GFP) mutants with shifted excitation and emission spectra has made it feasible to measure protein-protein interactions by using GFP tags as intracellular markers. GFP-tagged protein chimeras are expressed intracellularly and do not require any chemical treatment to become fluorescent. FRET can also occur between fusions of blue-emitting and green-emitting GFP variants.

As described above, a donor fluorescent protein label is capable of absorbing a photon and transferring energy to another fluorescent label. The acceptor fluorescent protein label is capable of absorbing energy and emitting a photon. If needed, the linker connects the binding domain, sequence or polypeptide either directly, or indirectly through an intermediary linkage, with one or both of the donor and acceptor fluorescent protein labels or the fluorescent label and, optionally, the quencher if a non-FRET assay is being performed. Regardless of the relative order of the binding domain, sequence or polypeptide or its binding partner and the donor and acceptor fluorescent protein labels on a polypeptide molecule, it is essential that sufficient distance be placed between the donor and acceptor or the fluorescent label and corresponding quencher by the linker and/or the binding domain, sequence, nucleic acid or polypeptide and corresponding binding partner to ensure that FRET does not occur unless the binding domain, sequence or polypeptide and its binding partner bind. It is desirable, as described in greater detail in WO97/28261, to select a donor fluorescent protein label with an emission spectrum that overlaps with the excitation spectrum of an acceptor fluorescent protein label. In some embodiments of the invention the overlap in emission and excitation spectra will facilitate FRET. A fluorescent protein of use in the invention includes, in addition to those with intrinsic fluorescent properties, proteins that fluoresce due to intramolecular rearrangements or the addition of cofactors that promote fluorescence.

For example, green fluorescent proteins (GFPs) of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium* (Ward et al., 1982, Photochem. Photobiol. 35:803-808; Levine et al., 1982, Comp. Biochem. Physiol. 72B:77-85). A variety of *Aequorea*-related GFPs having useful excitation and emission spectra have been engineered by modifying the amino acid sequence of a naturally-occurring GFP from *Aequorea Victoria* (Prasher et al., 1992, Gene 111:229-233; Heim et al., 1994, Proc. Natl. Acad. Sci. U.S.A. 91:12501-12504; PCTUS95/14692). As used herein, a fluorescent protein is an *Aequorea*-related fluorescent protein if any contiguous sequence of 150 amino acids of the fluorescent protein has at least 85% sequence identity with an amino acid sequence, either contiguous or non-contiguous, from the wild-type *Aequorea* green fluorescent protein (SwissProt Accession No. P42212). Similarly, the fluorescent protein may be related to *Renilla* or *Phialidium* wild-type fluorescent proteins using the same standards. *Aequorea*-related fluorescent proteins include, for example, wild-type (native) *Aequorea victoria* GFP, whose nucleotide and deduced amino acid sequences are presented in GenBank Accession Nos. L29345, M62654, M62653 and other *Aequorea*-related engineered versions of Green Fluorescent Protein, of which some are listed above. Several of these, i.e., P4, P4-3, W7 and W2 fluoresce at a distinctly shorter wavelength than wild type.

Recombinant nucleic acid molecules encoding single- or tandem fluorescent protein/polypeptide comprising engineered binding domain, sequences or polypeptides or their binding partners useful in the invention may be expressed for in vivo assays of the activity of a modifying enzyme on the encoded products.

Similar assays using different ligands, different detection techniques, etc. are readily designed by one of skill in the art using the information provided in the art generally.

Isosteric Binding Molecule

There are a variety of techniques well known in the art for assessing compound modulation of APF binding to CKAP4. A wide variety of detectable labels can be used, and the assays can be conducted in heterogeneous or homogeneous formats. The assay can be conducted in a homogeneous format using fluorescence techniques, for example, where the fluorescence of a fluorescent label attached to the compound is altered by virtue of its binding to a peptide the size of the CKAP4, APF and/or DHHC2, or larger. The CKAP4 itself can be supplied in the context of the nonstructural protein or fragment thereof or can be supplied per se or as a fusion protein that contains a label, such as green fluorescent protein.

In an exemplary extracellular format, the effect of individual compounds or mixtures of compounds on the binding of the APF or a protein containing it with a CKAP4 containing membrane preparation can be evaluated. Techniques similar to those described above may be used—e.g., the CKAP4 and/or the membrane preparation may be labeled and the APF or protein containing it. The binding of the label APF to CKAP4 in the presence and absence of compound or mixtures of compounds can be determined. These assays can be conducted in homogeneous format by using fluorescence labeling, for example, of the CKAP4, APF and/or DHHC2.

A wide variety of such protocols is known in the art, and the essential feature is determination of the effect of the compound or a mixture of compounds on the binding of the APF or a protein containing it and the CKAP4 containing membrane preparation. Perhaps a particularly convenient embodiment of this method would involve a fusion between the CKAP4 and a fluorescent protein which could be produced very conveniently using recombinant techniques; assessment of the binding of APF to this fusion in the membrane preparation either in a heterogeneous or homogeneous format can then be performed.

An assay for binding of the APF or APF containing peptide to a CKAP4 containing microsomal membrane can be performed by treating a microsomal or cytoplasmic membrane preparation in vitro with a peptide containing the APF and distributing the contents of the reaction mixture in a sedimentation gradient. The bound APF can be detected in the appropriate gradient fraction using polyacrylamide gel electrophoresis. The bound APF and/or CKAP4 may be labeled for example, with a radioisotope or a coupled fluorescent label such as green fluorescent protein used in a fusion. This assay can be used to screen for compounds or protocols that disrupt binding to the microsomal membrane by conducting the assay in the presence and absence of the protocols or compounds and comparing the results.

In addition to the above-described methods that can be conducted extracellularly, the effect of various protocols and compounds or mixtures of compounds on the behavior in terms of binding to CKAP4 containing cytoplasmic membranes of the APF or APF containing peptide can be determined in a variety of intracellular assays. Any eukaryotic cells may be used, but typically and most conveniently, mammalian cells or yeast cells are used in these assays.

Intracellular assays can be performed by generating desired peptide constructs intracellularly from recombinant expression systems. Alternatively, the assays can be conducted by first preparing the labeled CKAP4, APF and/or DHHC2 or protein containing said CKAP4, APF and/or DHHC2 and introducing the derivatized CKAP4, APF and/or DHHC2 into the cells using cell-penetrating peptides. The compounds to be tested may be introduced in the same manner. Such cell-penetrating peptides are described, for example, in a review article by Lindgrin, M., et al., in TiPS (2000) 21:99-103, the contents of which are incorporated herein by reference to describe an exemplary list of such cell-penetrating peptides. These peptides can be coupled to any substance to facilitate the entry of said substance into a eukaryotic cell.

In the most direct forms of such assays, the change in intracellular distribution of the labeled APF and/or CKAP4 either supplied per se or in the context of a larger protein can be determined. A wide variety of labels can be used; perhaps the most convenient is a fusion with a fluorescent protein, or simple coupling of the CKAP4 or the protein containing it to a detectable fluorescent label. The location of the labeled CKAP4 or protein containing it can then be observed by a variety of methods including direct observation and histological techniques. Thus, in one example, the effect of a candidate compound or protocol directly on the ability of the APF to bind to CKAP4 containing cellular membranes can be assessed by coupling the CKAP4 to a reporter which is detectable; most convenient are labels which are fusion proteins formed with the CKAP4, such as a fluorescent protein. The intracellular locations of the reporter in the presence and absence of the candidate protocol compound can then be compared. Compounds or protocols that are able to disrupt the binding of the APF with the CKAP4 in the membrane can readily be identified when their presence results in less label associated with cell membranes.

If histological techniques are used, the label can be less direct; for example, the CKAP4 might be fused to a protein that can be detected with a labeled antibody or may be fused to an enzyme that can be detected in the presence of a substrate. Once the cells are fixed histologically, the supplementary reagents can be added for detection.

Test compounds that appear to interrupt the ability of the APF to bind CKAP4 in the cellular membranes, or which are shown to disrupt the normal binding pattern of the APF to CKAP4 can be confirmed as anti-IC agents.

When intracellular formats are used, in addition to testing compounds and mixtures of compounds, as noted above, it is possible to test the effect of protocols which involve various regimes of treatment, including, in addition to providing compounds, various antisense techniques, and various forms of environmental stress such as pH changes, temperature changes, mechanical disturbances and the like.

In addition to the foregoing, somewhat more sophisticated methods to assess the impact of compounds and protocols on the intracellular location of substances containing the APF and/or CKAP4 proteins can be employed. For example, in addition to causing the protein to fail to associate with CKAP4 containing cytoplasmic membranes, directs this protein to the nucleus. Therefore, the assay methods can include features in the substance containing the CKAP4 that act as nuclear localization signals (NLS), many of which are well known in the art. Under these conditions the label can constitute a functionality which exerts its effect in the nucleus, and the disruption of binding of the APF to CKAP4 containing cytoplasmic membrane can be detected by a reporter function associated with the APF to CKAP4 binding which exerts its effects in the nucleus. Such effects would be, for example, enhancement or repression of the expression of a detectable protein; this would involve including transactivators, transcription factors, or repressors, and the NLS. Of course, the nuclear localization signal—derived constructs can also be detected in the nucleus directly, using a direct detectable label of the sort described above—e.g., GFP, a partner in an antibody/antigen interaction, or an enzymatic activity, or a radiolabel.

Alternative proteins whose expression can be detected are those, such as GFP, that are detectable per se or may be detectable by virtue of their effects on cellular growth, such as his3, leu2, β-galactosidase, β-glucoronidase, SV40T antigen, chloramphenicol acetyl transferase (CAT), hygromycin B phosphotransferase, SEAP or cell surface antigens such as CD4. In addition to transactivators, transcription factors which enhance expression include derivatives of lexa, cI, or gal4 DNA binding domains fused to activation domains of B42, VP16 and the like.

By conducting the foregoing assays, compounds and/or protocols are identified which will be effective in treating IC. By "treating" is meant both therapeutic and prophylactic treatment, and refers to a desirable effect on viral load, or symptomology, or any desirable outcome which mitigates the negative consequences of the typical progress of IC infection. The term "treat" is not to be construed to imply absolute cure or absolute prevention. Any helpful amelioration or repression of the infection is sufficient to meet this definition.

Compounds thus identified can be administered in conventional ways using standard pharmaceutical formulations such as those set forth in Remington's Pharmaceutical Sciences, latest edition, Mack Publishing Co., Easton, Pa., incorporated herein by reference. (See also, References 23-33.) Various enteral or parenteral routes of administration may be used, including administering by injection, such as intravenous, intramuscular, subcutaneous and the like, or by oral administration or by suppository. In addition, sustained release compositions can also be used.

The terms "an effective amount," "an anti-IC effective amount," or a "pharmaceutically effective amount" of a peptide of the present invention as applied to such molecules refers to an amount of a peptide, or combination of two or more peptides as disclosed herein, effective in reducing or ameliorating conditions, symptoms, or disorders associated with IC or associated pathogenesis in patients.

Effective amounts of compounds for the treatment or prevention of IC, delivery vehicles containing compounds or constructs encoding the same, agonists, and treatment protocols, can be determined by conventional means. For example, the medical practitioner can commence treatment with a low dose of one or more peptides in a subject or patient in need thereof, and then increase the dosage, or systematically vary the dosage regimen, monitor the effects thereof on the patient or subject, and adjust the dosage or treatment regimen to maximize the desired therapeutic effect. Further discussion of optimization of dosage and treatment regimens can be found in Benet et al., in Goodman & Gilman's The Pharmacological Basis of Therapeutics, Ninth Edition, Hardman et al., Eds., McGraw-Hill, New York, (1996), Chapter 1, pp. 3-27, and L. A. Bauer, in Pharmacotherapy, A Pathophysiologic Approach, Fourth Edition, DiPiro et al., Eds., Appleton & Lange, Stamford, Conn., (1999), Chapter 3, pp. 21-43, and the references cited therein, to which the reader is referred.

The dosage levels and mode of administration will be dependent on the nature of the compound identified and the particular situation of the subject. Optimization of routes of administration, dosage levels, and adjustment of protocols, including monitoring systems to assess effectiveness of the treatment are routine matters well within ordinary skill. Protocols which are identified using the intracellular assays set forth above must, of course, be modified in the context of treatment of subjects, and this, too, falls within the skill of the practitioner.

Typically, the compounds that are identified by the methods of the invention will be "small molecules"—i.e., synthetic organic structures typical of pharmaceuticals. Examples of such "small molecules" are found, for example, in the Physicians' Desk Reference (with respect to approved drugs), the Merck Index, and the U.S. Pharmacopoeia. However, such compounds may also include peptides, peptidomimetics, nucleic acids, peptide nucleic acids, carbohydrates, lipids, and the like.

In addition to compounds identified by means of the foregoing assays, protocols and substances useful in treating IC can be formulated and utilized a priori. For example, the APF, the CKAP4 protein, or peptides thereof protein, or functional fragment thereof can readily be used in treatment by virtue of its ability to bind CKAP4 or to compete with the APF binding to CKAP4.

Thus, formulations of the CKAP4, APF and/or DHHC2 protein, or peptides thereof protein, or functional fragment thereof can be used directly to treat IC infection. Typically, these formulations will contain peptides of less than 60 amino acids, in another embodiment less than 50 amino acids, in another embodiment less than 30 amino acids, and, in yet another embodiment less than 25 amino acids in another embodiment, not be less than 4 amino acids. The peptides may be as short as 10-15 amino acids, 6-9 amino acids or 4-6 amino acids, so long as functionality in terms of competitive binding, or inhibition of binding, is retained. Methods to synthesize such peptides are, of course, well known, both direct and recombinant methods may be used. Thus, a peptide useful in the method of the invention will typically contain from about 4 to 60 amino acids.

The peptides useful in the methods of the invention can also be generated in the subject to be treated by virtue of administering expression systems for those peptides consisting entirely of gene-encoded amino acids. These expression systems may be introduced as naked DNA, as expression vectors suitable for transfection of mammalian cells, or for example using adenoviral or retroviral or other suitable viral vectors.

As described above, however, these competitor peptides need not be the native sequences per se and need not even be peptides per se, but may contain isosteric linkages or other polymeric features that result in similar charge/shape features as compared to the native helices.

Peptides, or compounds with similar charge/shape features and having the activity of the peptides described herein, can be identified by phage display using wild-type or mutant APF and wild-type or mutant CKAP4 peptides as selectors.

The compositions or agents of the invention may comprise, consist essentially of, or consist of the peptide sequences disclosed herein. The phrase "consists essentially of or consisting essentially of" or the like, when applied to anti-CKAP4, APF and/or DHHC2 encompassed by the present invention refers to peptide sequences like those disclosed herein, but which contain additional amino acids (or analogs or derivatives thereof as discussed above). Such additional amino acids, etc., however, do not materially affect the basic and novel characteristic(s) of these peptides in modulating, attenuating, or inhibiting IC infection, replication, and/or pathogenesis, including the specific quantitative effects of these peptides, compared to those of the corresponding peptides disclosed herein.

siNA

This invention comprises compounds, compositions, and methods useful for modulating CKAP4 and/or APF gene or promoter expression or activity using short interfering nucleic acid (siNA) molecules. This invention also comprises compounds, compositions, and methods useful for modulating the expression and activity of other genes involved in pathways of, for example, CKAP4, APF, and/or DHHC2 gene, or promoter expression and/or activity by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression or activity of, for example, CKAP4, APF, and/or DHHC2 gene, or promoter, or the activity or expression of other components of the pathway.

A siNA of the invention can be unmodified or chemically-modified. A siNA of the instant invention can be chemically synthesized, expressed from a vector or enzymatically synthesized. The instant invention also features various chemically-modified synthetic short interfering nucleic acid (siNA) molecules capable of modulating CKAP4 and/or APF gene or promoter expression or activity in cells by RNA interference (RNAi). The use of chemically-modified siNA improves various properties of native siNA molecules through increased resistance to nuclease degradation in vivo and/or through improved cellular uptake. Further, contrary to earlier published studies, siNA having multiple chemical modifications retains its RNAi activity. The siNA molecules of the instant invention provide useful reagents and methods for a variety of therapeutic, diagnostic, target validation, genomic discovery, genetic engineering, and pharmacogenomic applications.

In one embodiment, the invention features a double-stranded short interfering nucleic acid (siNA) molecule that modulates, for example, CKAP4, APF, and/or DHHC2 gene, or promoter expression and/or activity, wherein said siNA molecule comprises about 19 to about 21 base pairs.

In one embodiment, the invention features a siNA molecule that modulates, for example, CKAP4, APF, and/or DHHC2 gene, or promoter expression and/or activity, for example, wherein the CKAP4, APF, and/or DHHC2 gene or promoter comprises CKAP4, APF, and/or DHHC2 encoding sequence. In one embodiment, the invention features a siNA molecule that modulates expression of a CKAP4, APF, and/or DHHC2 gene or CKAP4, APF, and/or DHHC2 promoter, for example, wherein the CKAP4, APF, and/or DHHC2 gene or promoter comprises CKAP4, APF, and/or DHHC2 non-coding sequence or regulatory elements involved in CKAP4, APF, and/or DHHC2 gene or promoter expression.

In one embodiment, the invention features a siNA molecule having RNAi activity against, for example, CKAP4, APF, and/or DHHC2, wherein the siNA molecule comprises a sequence complementary to any RNA having CKAP4, APF, and/or DHHC2 encoding sequence. In another embodiment, the invention features a siNA molecule having RNAi activity against CKAP4, APF, and/or DHHC2 RNA, wherein the siNA molecule comprises a sequence complementary to an RNA having other CKAP4, APF, and/or DHHC2 encoding sequence, for example other mutant CKAP4, APF, and/or DHHC2 gene or promoters.

In one embodiment of the invention a siNA molecule comprises an antisense strand comprising a nucleotide sequence that is complementary to a nucleotide sequence or a portion thereof encoding, for example, an CKAP4, APF, and/or DHHC2 protein. The siNA further comprises a sense strand, wherein said sense strand comprises a nucleotide sequence of an CKAP4, APF, and/or DHHC2 gene or promoter or a portion thereof.

In another embodiment, a siNA molecule comprises an antisense region comprising a nucleotide sequence that is complementary to a nucleotide sequence encoding an CKAP4, APF, and/or DHHC2 protein or a portion thereof. The siNA molecule further comprises a sense region, wherein said sense region comprises a nucleotide sequence of an CKAP4, APF, and/or DHHC2 gene or promoter or a portion thereof.

In one embodiment, a siNA molecule of the invention has RNAi activity that modulates expression of RNA encoded by, for example, an CKAP4, APF, and/or DHHC2 gene. Because CKAP4, APF, and/or DHHC2 gene can share some degree of sequence homology with each other, siNA molecules can be designed to target a class of CKAP4, APF, and/or DHHC2 gene or alternately specific CKAP4, APF, and/or DHHC2 gene (e.g., polymorphic variants) by selecting sequences that are either shared amongst different CKAP4, APF, and/or DHHC2 targets or alternatively that are unique for a specific CKAP4, APF, and/or DHHC2 target. Therefore, in one embodiment, the siNA molecule can be designed to target conserved regions of, for example, CKAP4, APF, and/or DHHC2 RNA sequences having homology among several CKAP4, APF, and/or DHHC2 gene or promoter variants so as to target a class of CKAP4, APF, and/or DHHC2 gene with one siNA molecule. Accordingly, in one embodiment, the siNA molecule of the invention modulates the expression of, for example, one or both CKAP4, APF, and/or DHHC2 alleles in a subject. In another embodiment, the siNA molecule can be designed to target a sequence that is unique to a specific CKAP4, APF, and/or DHHC2 RNA sequence (e.g., a single CKAP4, APF, and/or DHHC2 allele or CKAP4, APF, and/or DHHC2 SNP) due to the high degree of specificity that the siNA molecule requires to mediate RNAi activity.

In one embodiment, nucleic acid molecules of the invention that act as mediators of the RNA interference gene silencing response are double-stranded nucleic acid molecules. In another embodiment, the siNA molecules of the invention consist of duplexes containing about 19 base pairs between oligonucleotides comprising about 19 to about 25 (e.g., about 18, 19, 20, 21, 22, 23, 24, 25 or 26) nucleotides. In yet another embodiment, siNA molecules of the invention comprise duplexes with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

In one embodiment, the invention features one or more chemically-modified siNA constructs having specificity, for example, for CKAP4, APF, and/or DHHC2 expressing nucleic acid molecules, such as RNA encoding a CKAP4, APF, and/or DHHC2 protein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy a basic residue incorporation. These chemical modifications, when used in various siNA constructs, are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C.

The invention will be illustrated in more detail with reference to the following Examples, but it should be understood that the present invention is not deemed to be limited thereto.

EXAMPLES

Example 1

The fluorescent reporter CKAP4-YFP was composed of the following DNA elements: CKAP4 was cloned by reverse transcription from a HeLa cell cDNA library (see FIG. 1). The 5' primer incorporated a kpnI site and the 3' primer an XhoI site in order to facilitate cloning. YFP was amplified by PCR from a plasmid containing the coding sequence for YFP. To aid in cloning the 5' primer for YFP included an XhoI site and the 3' primer an EcoRI site. The XhoI endonuclease sites, one at the 3' end of CKAP4 and the other at the 5' end of YFP resulted in an in-frame fusion of CKAP4 to YFP. Both of these cDNA fragments were ligated into pcDNA3 that was linearized with KpnI and EcoRI. Translation of the mRNA generated from this expression construct began at the start codon of CKAP4 and ended at the stop codon of YPF.

HeLa cells (ATCC# CCL-2), (SCHERER W F, SYVERTON J T, GEY G O. Studies on the propagation in vitro of poliomyelitis viruses. IV. Viral multiplication in a stable strain of human malignant epithelial cells (strain HeLa) derived from an epidermoid carcinoma of the cervix. J Exp Med. 1953 May; 97(5):695-710) a human cervical adenocarcinoma cell line with epithelial cell-like characteristics were obtained from the American Type Culture Collection (American Type Culture Collection (ATCC) (P.O. Box 1549 Manassas, Va. 20108 USA). The cells were maintained in culture and subcultured according to the following protocol: ATCC complete growth medium: Dulbecco's minimal essential medium (DMEM). To make the complete growth medium, add the following components to the base medium: fetal bovine serum to a final concentration of 10%. Atmosphere: air, 95%; carbon dioxide (CO2), 5% Temperature: 37.0° C. Subculturing Protocol:

1. Remove and discard culture medium.
2. Briefly rinse the cell layer with 0.25% (w/v) Trypsin-0.53 mM EDTA solution to remove all traces of serum which contains trypsin inhibitor.
3. Add 2.0 to 3.0 ml of Trypsin-EDTA solution to flask and observe cells under an inverted microscope until cell layer is dispersed (usually within 5 to 15 minutes). Note: To avoid clumping do not agitate the cells by hitting or shaking the flask while waiting for the cells to detach. Cells that are difficult to detach may be placed at 37° C. to facilitate dispersal.
4. Add 6.0 to 8.0 ml of complete growth medium and aspirate cells by gently pipetting.
5. Add appropriate aliquots of the cell suspension to new culture vessels.
6. Incubate cultures at 37° C.

Example 2

A Subcultivation Ratio

A subcultivation ratio of 1:2 to 1:6 was used. Generation of cell lines that stably express the APF reporter CKAP4:YFP. HeLa cells stably expressing CKAP4:YFP will be generated by two standard methods. In the first method, HeLa cells will be transfected with a mammalian expression plasmid, pcDNA3CKAP4:YFP using the FuGene6 reagent. This plasmid also encodes resistance to geneticin and will be maintained with 0.4 mg/ml geneticin. The second method will use lentiviral infection at a multiplicity of infection equal to one integrant per cell-host genome. The cDNA expressing the reporter will be cloned into pLenti6.3 TOPO (Invitrogen) or a similar vector. Clonal cell lines stably expressing the APF reporter CKAP4:YFP will be selected by exposure of infected cells to culture medium containing 20 micrograms/mL blasticidin. Stable transfectants generated from each method will be chosen based on similarity to endogenous CKAP4 distribution, sorted by FACS (fluorescence activated cell sorter) to obtain a homogeneous population of cells expressing CKAP4:YFP, and maintained using standard cell culture techniques. A preliminary evaluation using microscopic, visual examination of the expression will be done to select clones that express the reporter in a manner that resembles the endogenous pattern of CKAP4 expression. Particular care will be taken to choose clones that do not expressively high or low quantities of the reporter. Once clones have been selected for appropriate expression by visual inspection, they will be characterized further by measuring their positive response to saturating concentration of synthetic APF (defined here as 20 nM or greater). The source of synthetic APF is from Peptides International (Louisville, Ky.). The positive response is defined as the rate and degree of translocation of the APF reporter CKAP4:YFP. Clonal cell lines that respond appropriately (defined here as: the translocation of the reporter CKAP4:YFP into the nucleus in one hour, to a degree sufficient to be statistically greater (defined here as two standard deviations greater than the mean of control or more) than controls. Clonal lines that pass the positive-response test will be characterized further by assessing their response to varying doses of synthetic APF ranging from 0, beginning at 10 fM and up to 100 nM in 10-fold incremental increases in the dose of synthetic APF. Clona cell lines that respond to the variable dose in a fashion that fits well to a sigmoidal curve will be deemed "APF-reporter clonal cell lines".

Example 3

Characterization of Nuclear Translocation Assay Using Synthetic APF

To determine the dynamic range of this assay, we will first measure the degree of CKAP4:YFP nuclear translocation in response to varying concentrations of synthetic APF (Peptides International) ranging from 10 fM to 100 nM (control=no APF) using the reporter cell line described above. If the lowest concentration of APF stimulates translocation of CKAP4:YFP, it will be reduced further until no response is seen. This will allow us to define the lower end of sensitivity of the assay. For each APF concentration, the abundance of CKAP4:YFP in the nucleus will be measured using morphometry and high-content screening algorithms (e.g., MS Elements, Nikon; CytoShop 2.0, Vala Sciences, respectively) that can measure the abundance of a targeted fluorophore at almost any desired location in the cell (e.g., plasma membrane, nucleus, nucleolus) (Morelock et al, 2005; Mikic et al, 2006). The abundance of CKAP4:YFP fluorescence in the nucleus will be quantitated by taking two separate images of the cells. The first image will be of DRAQ5 (a far-red, nucleic acid binding fluorophore that avoids emission overlap with YFP) staining in the nucleus; the second of CKAP4:YFP fluorescence. An algorithm will then quantify the amount of CKAP4:YFP fluorescence that is coincident with the nuclear stain, and subsequent, built-in statistical analyses will be used to determine the variability among cells to a single treatment. Statistical analyses of the differences between the mean values for populations of cells treated with different concentrations will be determined by 2-way ANOVA analyses. The algorithm to quantify nuclear translocation is among the oldest, most robust morphometric, high-content screening algorithms in existence. Using these programs, large numbers of cells (100s to thousands in each field of view for each condition) can be measured to determine mean values for the nuclear translocation with a high degree of statistical confidence. These measurements will provide a dose response curve from which the EC50 for synthetic APF-induced CKAP4:YFP translocation will be determined as well as the sensitivity of the assay. Our preliminary data indicated that CKAP4:YFP translocation occurred within two hours of APF treatment; therefore, for determining the dose-dependent response, we will make initial morphometric measurements 15 min, 30 min, 60 min, 90 min, 2 hr, 4 hr, and 6 hr after APF application on fixed cells. This time course can then be adjusted (to focus in on a window for maximal signal to noise ratio) and the dose-dependent response remeasured after we make a more thorough determination of the rate of CKAP4: YFP translocation as described below.

The rate of CKAP4:YFP translocation will be assessed by time-lapse imaging during exposure of HeLa cells to a saturating dose of APF (as determined in the dose response experiments). CKAP4:YFP nuclear abundance will be measured as described above and plotted over time. The rate (t½) of CKAP4:YFP nuclear translocation and time to plateau will be determined by fitting the data to an appropriate curve using Microcal Origin 6.0. Knowing the rate of translocation following exposure of cells to a saturating dose of APF will allow us to define the upper end of the dynamic range of the translocation metric. The difference between these two measures, the dose-response (dynamic range) as well as the time course of the translocation, will allow us to determine whether the assay yields an acceptable Z-score (Zhang et al, 1999). This coefficient takes into account the signal dynamic range and the data variation associated with the signal measurements; therefore, it assesses the overall quality or robustness of the assay and, ultimately, its usefulness as a diagnostic assay for IC. The Z-score is the standard by which virtually all high-throughput and high-content assays are measured. In addition, determining the time dependence of the dose-dependent response of CKAP4:YFP nuclear translocation will provide the parameters necessary to develop a "fixed-endpoint assay". In this format, APF is applied to the reporter cells in culture for a predetermined amount of time at which point the cells will be fixed, the nuclei stained, and the amount of CKAP4:YFP fluorescence in the nucleus measured as described above. This assay format is easily standardized and therefore has the most potential for widespread, commercial use.

Validation of CKAP4:YFP Nuclear Translocation Assay Using Patient Urine: To validate this assay for further development as a clinical diagnostic test for IC, we will determine its ability to report APF activity in urine of women clinically diagnosed with IC (according to NIDDK criteria). Adult women comprise 90% of patients diagnosed with this disease; therefore, recruitment of female patients for this initial feasibility study will be more straightforward to achieve. Urine from asymptomatic women and from women diagnosed with acute bacterial cystitis will be included as controls. Urine will be collected at Mercy Hospital from women with IC at least 3 months after the most recent known bacterial urinary tract infection and one month after the last antibiotic use. Specimens will be obtained from women during routine office visits to Advanced Gynecological Associates at Mercy Hospital for management of IC. Asymptomatic controls will be female volunteers with no history of IC or other urologic disease and will be required to have no symptoms of urinary tract infection or antibiotic use for at least 1 month. Urine will also be collected at the time of diagnosis from female patients with acute bacterial cystitis (diagnosis based on the presence of [more than 103 bacteria/mL with a single type of bacterium isolated] plus pyuria in combination with appropriate symptoms). All participants will be at least 18 years old and enrolled in accordance with guidelines of the Scranton Temple Residency Program Instructional Review Board. Participants will also be required to read and sign an informed consent form. We aim to recruit a minimum of 50 patients from each category, as similar numbers of patients have been used to successfully determine the validity of cellular proliferation as a diagnostic assay for IC (Keay et al, 1998). Urine will be collected by the clean catch method in which each IC patient or control wipes the labial area with 10% povidone iodine solution and then collects midstream urine into a sterile container. Specimens will be kept at 4° C. and then transported to our laboratory for removal of cellular debris by low speed centrifugation at 4° C. Each sample will be aliquoted under sterile conditions and stored at −80° C. until ready for use in the protocol listed below. Importantly, the same urine samples will be tested for APF activity using a cellular proliferation assay (3H-thymidine incorporation measured by the method of Keay et al, 1996) in order to validate the effectiveness of the CKAP4:YFP reporter system against the current bioassay for APF detection in patient urine.

1. The day before the assay is performed, CKAP:YFP HeLa cells will be seeded in 35 mm imaging dishes at a density of 50,000 cells/dish in normal DMEM and incubated overnight at 37° C. and 5% $CO_2$ (resulting in approximately 60% confluence the next day).
2. The following day, the medium will be replaced with serum-free DMEM, and the cells inspected under a microscope to ensure that they look healthy and uncontaminated, and that there is no uneven distribution of cells around the edge of the plate.
3. 4-6 hours later, urine specimens from patients with IC or controls will be adjusted to pH 7.2 and 300 mOsm, filtered through a 0.2-μm pore filter, diluted 1:2 in DMEM (with only Glutamax and antibiotic/antimycotic solution) and applied to the cells.
4. Cell plates will be incubated for a predetermined amount of time (determined in section 1.2) at 37° C. and 5% $CO_2$.
5. Cell medium will be removed and the cells will be fixed for 10 min at room temperature in 4% formaldehyde in phosphate buffer [pH=7.0].
6. Cells will be washed 4 times with phosphate buffered saline (PBS) and then the cell nuclei will be stained by adding 500 μl 1 μM DRAQ5 (Biostatus) in PBS containing 1 mM $MgSO_4$.
7. The abundance of CKAP4:YFP in the nuclei will be measured as described above. The concentration of APF in the patient's urine will be determined by comparing the degree of translocation to the dose-response curve generated in experiments described above.

Example 4

Statistical Analysis

The mean and standard deviation of the APF concentration measured in the urine from each patient population (IC, bacterial cystitis, and asymptomatic) will be determined. These values will be subjected to a two-way ANOVA analysis to determine whether or not they are significantly different from each other. Importantly, similar numbers of patients have been used to successfully determine the validity of cellular proliferation as a diagnostic assay for IC (Keay et al, 1998). The variability that exists among the members of a single population, in particular the IC patient population may provide information that allows us to further correlate disease severity or length of time since diagnosis to APF concentration. To examine such a relationship, patients in all categories will be binned according to the amount of APF that is present in their urine. These categories will then be analyzed with respect to clinically relevant factors including patient age, severity of IC, and length of time since diagnosis (or when symptoms first appeared) and their conditional likelihood measured. Ultimately, these analyses are intended to provide 1) an indication of whether to move forward with a larger-scale clinical trial aimed at determining the utility of this assay as a diagnostic test for IC in men and women and 2) a first glimpse at the relationship between the clinical pathology and symptomology of IC and APF concentration in patient urine.

DNA Constructs—A vector construct containing wild-type CKAP4 (WT CKAP4) fused in-frame to the N-terminus of the V5 and 6×His epitope tags was generated by PCR using CKAP4 specific primers and cDNA from HeLa cells. A palmitoylation-incompetent form of CKAP4 (CKAP4 C100S) was created using site-directed mutagenesis (Stratagene, La Jolla, Calif.) to alter the cysteine at position 100 to serine. DHHC2 was cloned in-frame to the C-terminus of mCFP to generate an N-terminal CFP fusion protein. All constructs were verified by DNA sequencing.

Cell Culture and Transfections—HeLa (ATCC #CCL-2; American Type Culture Collection, Manassa, Va.) cells were maintained in Dulbecco's modified Eagle's medium (DMEM) containing 10% fetal bovine serum (FBS), 100 U/ml penicillin, 100 µg/ml streptomycin, and 1 µg/ml fungizone (all from Invitrogen). Cells were transfected using FuGENE6 reagent (Roche, Basel, Switzerland) according to the manufacturer's instructions. To obtain stable clones, cells were diluted into 96-well plates (100 cells/well) 24 hours post-transfection and selected in the presence of 0.4 mg/ml Geneticin (G418) (Invitrogen, Carlsbad, Calif.).

Normal primary bladder (NB) epithelial cells were isolated from patients as previously described (Keay et al., 1996; Keay et al., 2000; Keay et al., 2004a; Conrads et al., 2006). Cells were propagated in DMEM-F12 (Media-Tech, Manassas, Va.) with 10% heat inactivated FBS, 1% antibiotic/antimycotic solution, 1% L-glutamine, 0.25 U/ml insulin (Sigma, St. Louis, Mo.), and 5 ng/ml human epidermal growth factor (R & D Systems, Minneapolis, Minn.) at 37° C. in a 5% CO2 atmosphere, and characterized by binding of AE-1/AE-3 pan-cytokeratin antibodies (Signet, Emeryville, Calif.) as previously described (Keay t al., 1996; Keay et al., 2004b).

siRNA—Double-stranded siRNA (ON-TARGETplus™) targeting ZDHHC2 and nonsense siRNA (ONTARGETplus™ Control siRNA) were purchased from Dharmacon (Lafayette, Colo.). HeLa cells were trypsinized for 5 minutes at 37° C., centrifuged in DMEM growth medium, and the cell pellet was resuspended in serum-free medium at a density of 1×10⁶ cells/ml. 200 µl of the cell suspension was then transferred to a sterile 2 mm cuvette with 14 □□g siRNA and electroporated at 160 V/500 µF capacitance using a BioRad Gene Pulser Xcell. The cells were immediately transferred to 96-well plates for thymidine incorporation assay or to LabTek multiwell glass slides (Nalge Nunc, Rochester, N.Y.) for immunocytochemistry. To determine the effectiveness of siRNA-mediated knockdown we used quantitative real-time PCR to measure the abundance of ZDHHC2 mRNA at times 0, 12, 24, 48, 72 and 96 hours following transfection of the siRNA. These experiments were run in triplicate.

3H-Thymidine Incorporation—Cell proliferation was measured by 3H-thymidine incorporation into the DNA of HeLa or NB epithelial cells. Briefly, synthetic APF or inactive control peptide (NeoMPS, San Diego, Calif.) was resuspended in acetonitrile/distilled water (1:1), diluted in serum-free DMEM, and applied to HeLa or NB cells; cell controls received acetonitrile/distilled water diluted in serum-free DMEM alone. Cells were then incubated at 37° C. in a 5% CO2 atmosphere for 48 hours. The cell contents were harvested and methanol-fixed onto glass fiber filter paper, and the amount of radioactivity incorporated determined. Significant inhibition of 3H-thymidine incorporation was defined as a mean decrease in counts per minute of greater than 2 standard deviations from the mean of control cells for each plate.

Immunocytochemistry—HeLa cells stably transfected with WT CKAP4 or CKAP4 C100S were seeded at a density of 2×10⁴ cells/well in 8-well LabTek chamber slides (Nalge Nunc) and grown to semiconfluence in DMEM medium containing 10% FBS, 100 U/ml penicillin, 100 µg/ml streptomycin, 1 µg/ml fungizone, and 0.4 mg/ml G418 (all from Invitrogen). Cells were fixed for 20 minutes with 3% paraformaldehyde in PBS, permeabilized with 0.1% Triton X-100 in PBS, and blocked in PBS/5% NGS (normal goat serum). Cells transfected with DHHC2 siRNA and treated with synthetic APF (Peptides International, Louisville, Ky.) were fixed using ethanol/acetone (1:1) for 15 minutes at room temperature and washed three times with 1×PBS prior to blocking in PBS/5% NGS. The following primary antibodies were used: mouse mAb G1/296 against CKAP4 ("anti-CLIMP-63", diluted 1:100, Alexis Biochemicals, San Diego, Calif.), rabbit pAb against calreticulin (diluted 1:1000, Abcam, Cambridge, Mass.), and fluorescein isothiocyanate (FITC)-conjugated mouse mAb against the V5 epitope (diluted 1:500, Invitrogen). Secondary antibodies were FITC-labeled goat anti-rabbit or goat anti-mouse (diluted 1:1000, Invitrogen) and tetramethyl rhodamine isothiocyanate (TRITC)-labeled goat anti-mouse (diluted 1:1000, Jackson ImmunoResearch Laboratories, West Grove, Pa.). Slides were mounted in SlowFade Antifade reagent (Invitrogen) and imaged using a Nikon TE2000 epifluorescence microscope.

Quantitative Real-Time PCR (qRT-PCR)—Total RNA was extracted from synthetic APF, inactive control peptide-treated, or control untreated NB epithelial cells using the RNeasy Plus Mini Kit (Qiagen, Valencia, Calif.) according to the manufacturer's protocol. RNA was assessed by visualization of the 28S/18S ribosomal RNA ratio on a 1% agarose gel, and total RNA concentration determined by measuring the absorbance of each sample at 260 nm and 280 nm using a Gene Quant RNA/DNA Calculator (GE Healthcare, Piscataway, N.J.). Quantitative RT-PCR for gene expression was performed using Quantitect Primers (Qiagen), SYBR Green RT-PCR kit reagents (Qiagen), and a Roche System II Light-Cycler (software version 3.5). Samples were tested in triplicate runs, and specific mRNA levels quantified and compared to mRNA levels for β-actin using real-time PCR analysis software from Applied Biosystems (Foster City, Calif.).

Western Blot Analysis—Cells were lysed in ice-cold RIPA buffer containing protease inhibitors (Pierce, Rockford, Ill.), sonicated, and centrifuged for 15 minutes at 4° C. The supernatant protein concentration was measured using a Folin reagent-based protein assay kit (BioRad, Hercules, Calif.). Proteins were separated by electrophoresis using 4-12% NuPAGE Novex Bis-Tris polyacrylamide gels in MOPS running buffer (Invitrogen) and then transferred to nitrocellulose. Membranes were blocked for 2 hours at room temperature in TBST buffer (Tris-buffered saline, pH 7.4, with 0.1% Tween 20) containing 5% nonfat milk and incubated with specific antibodies against vimentin (diluted 1:2000; BD Pharmingen, San Jose, Calif.) or ZO-1 (diluted 1:125; Zymed Laboratories, San Francisco, Calif.) overnight at 4° C. The membranes were subsequently washed with TBST, incubated for 1 hour at room temperature in HRPconjugated goat anti-mouse (diluted 1:40000; Santa Cruz Biotechnology, Santa Cruz, Calif.) or goat antirabbit (diluted 1:10000; Pierce) secondary antibodies, and developed by enhanced chemiluminescence (Pierce). To assess equal loading of protein, the membranes were stripped and reprobed for β-actin (diluted 1:5000; Sigma). The membranes were exposed to film (BioMax AR, Kodak, Rochester, N.Y.) and the resulting images scanned at 300 dpi. The protein bands of interest were quantified using ImageJ and the integrated signal densities normalized first to β-actin (the loading control) and subsequently expressed in terms of the fractional abundance relative to untreated control cells.

Immunoprecipitation—HeLa cells were transfected with mCFP:DHHC2 or mock-transfected using FuGENE6 reagent (Roche) according to the manufacturer's instructions. Forty-eight hours later, cells were washed in PBS, lysed in 500 μL ice-cold lysis buffer (25 mM HEPES, 150 mM NaCl, 5 mM MgCl2, 1% NP-40, and protease inhibitor cocktail), and incubated on ice for 90 minutes with vortexing. After normalizing for equal protein concentration, lysates were immunoprecipitated with a mAb against GFP (JL-8 BD Biosciences, San Jose, Calif.; also recognizes the GFP spectral mutant, CFP) overnight at 4° C. with rocking. Protein G Sepharose 4B (Invitrogen) was added the following day, and the samples were incubated for an additional 18 hours at 4° C. with rocking. Proteins in the immunoprecipitation complex were washed four times in ice-cold lysis buffer and then heated in SDS sample buffer before separation by SDS-PAGE and transfer to nitrocellulose. Western blot analysis was performed as described above using a mAb against CKAP4 (G1/296, diluted 1:1000; Alexis Biochemicals).

Wound-healing Migration Assay—HeLa cells stably transfected with CKAP4 WT, CKAP4 C100S, or parental controls were seeded at a density of 4×10$^4$ cells/well in six-well plates coated with fibronectin. Once the cells reached confluency, the culture medium was replaced with medium containing AraC (5 μg/ml; Sigma) to block further cell division and permit measurement of migration in the absence of proliferation. The scratch wound was made using a p200 pipette tip eight hours after the addition of AraC. migration was monitored Over a 24 hour period starting at the time the scratch wound was made and at three-hour intervals thereafter using a Nikon Eclipse TE2000-U microscope under 20× magnification and phase contrast. The percent of the wound remaining open±SEM was measured at the indicated time points and calculated using Image J, with the 0 hour time point being set to 100%. The percentage of surface not covered by the cells was plotted versus time, and the data were fit to a monoexponential decay curve using Microcal Origin 6.0 to determine the rate at which the cells migrated to fill the exposed area. The distance between the two migrating front lines of cells was measured using the micrometer tool in NIS Elements (Nikon, Melville, N.Y.), and the rate of migration was determined and expressed as μM/hr.

Example 5

Expression Analyses of CKAP4 in a Broad Array of Tissues and Disease States, FIG. 18

GeneNote/GNF Normal/GNF Cancer Expression array images Experimental tissue vectors: Duplicate measurements were obtained for twelve normal human tissues (out of 28 tissues shown) hybridized against Affymetrix GeneChips HG-U95A-E (GeneNote data) and for 22 normal human tissues hybridized against HG-U133A (GNF Symatlas data **). The intensity values (shown on the y-axis) were first averaged between duplicates, then probeset values were averaged per gene, global median-normalized and scaled to have the same median of about 70 (half-way between GeneNOte and GNF medians). Available at GNF Symatlas, HG-U133A expression data for 18 NCI60 cancer cell lines was processed and added to the display (a single measurement taken; normalized according to the GNF Symatlas normal data). The correspondence between cell lines and tissues is shown. Normalized intensities are drawn on a root scale, which is an intermediate between log and linear scales. The Affymetrix MASS algorithm was used for array processing.

**Reference: Su A I, Wiltshire T, Batalov S, Lapp H, Ching K A, Block D, Zhang J, Soden R, Hayakawa M, Kreiman G, Cooke M P, Walker J R, Hogenesch J B (2004) A gene atlas of the mouse and human protein-encoding transcriptomes. Proc Natl Acad Sci USA. 2004 Apr. 20; 101(16):6062-7.

UniGene—electronic Northern Normal/eNorthern Cancer. Electronic Northern: For the shown set of non-fetal normal and cancer human tissues, NCBI's Unigene dataset (Hs.data) is mined for information about the number of unique clones per gene per tissue. Clones are assigned to particular tissues by applying data-mining heuristics to Unigene's library information file (Hs.lib.info). Electronic expression results were calculated by dividing the number of clones per gene by the number of clones per tissue. They were then normalized by multiplying by 1M, and the obtained normalized counts are presented on the same root scale as the experimental tissue vectors.

CGAP:SAGE Normal/SAGE Cancer

Serial Analysis of Gene Expression: For the same set of normal and cancer human tissues, CGAP datasets Hs.frequencies and Hs.libraries are mined for information about the number of SAGE tags per tissue. Tags are reassigned to a Unigene cluster and after that to a particular gene by mining Hs.best_gene, Hs.best_tag and Hs_GeneData. The expression level of a particular gene in a particular tissue was calculated as the number of appearances of the corresponding tag divided by the total number of tags in libraries derived from that tissue. These fractions were then normalized by multiplying by 1.2M and the obtained normalized counts are presented on the same root scale as that used for the electronic Northern pictures. Please note: Currently, only associations with minimal ambiguity participate in the analysis.

Example 6

A Prophetic Example. Use of Dose-Response Curve generated with Synthetic APF

It is envisioned that CKAP4 nuclear translocation can be used to determine the concentration of APF in the urine of patients with IC. For the assay to be useful in this capacity first it will be necessary to determine the dynamic range of this assay by measuring the degree of CKAP4:YFP nuclear translocation in response to varying concentrations of synthetic APF ranging from 10 fM to 100 nM (control=no APF) using the reporter cell line described above or endogenously expressed CKAP4. If the lowest concentration of APF stimulates translocation of CKAP4:YFP, it will be reduced further until no response is seen. This will provide the lower end of sensitivity of the assay. For each APF concentration, the abundance of CKAP4:YFP in the nucleus can be measured using morphometry and high-content screening algorithms available on the ArrayScanÒ VTI HCS Reader (e.g., vHCS Discovery ToolBox Software) that can measure the abundance of a targeted fluorophore at almost any desired location in the cell (e.g., plasma membrane, nucleus, nucleolus) (Morelock et al, 2005; Mikic et al, 2006). The abundance of CKAP4: YFP fluorescence or endogenous CKAP4 in the nucleus will be quantitated from two independent images of the same cells. The first image will be of DRAQ5 (a far-red, nucleic acid-binding fluorophore that avoids emission overlap with YFP) staining in the nucleus (or a similar fluorescent, DNA-labeling compound); the second of CKAP4:YFP fluorescence or immunolabeled, endogenous CKAP4. An algorithm will quantify the amount of CKAP4:YFP fluorescence or endogenous CKAP4 that is coincident with the nuclear stain, and subsequent, built-in statistical analyses will determine the variability among cells to a single treatment. Statistical analyses of the differences between the mean values for populations of cells treated with different concentrations will be determined by 2-way ANOVA analyses with age and treatment groups as the covariates. The algorithm to quantify nuclear translocation is among the oldest, most robust morphometric, high-content screening algorithms. Using these programs, large numbers of cells (100s to thousands in each field of view for each condition) can be measured to determine mean values for the nuclear translocation with a high degree of statistical confidence. These measurements will provide a dose response curve from which the EC50 for synthetic APF-induced CKAP4:YFP or endogenous CKAP4 translocation will be known. The measurements will be made at a fixed timepoint as determined by multiple trials to determine the timepoint of maximum translocation. This fixed endpoint will be the standard time for all subsequent assays using patient urine.

The degree of CKAP4:YFP or endogenous CKAP4 translocation that is induced by the application of patient urine (IC patient or otherwise) will be compared to the dose response curve obtained using synthetic APF. This standard method will provide a determination of the concentration of APF in the patient urine. Correlating the APF concentration measured with this assay to the clinical state of the patient will provide valuable insight into the onset, progression and pathogenesis of IC especially when multiple measurements are made from individuals over time.

While the invention has been described in detail and with reference to specific examples thereof, it will be apparent to one skilled in the art that various changes and modifications can be made therein without departing from the spirit and scope thereof.

---

What is claimed is:

1. A method of screening for interstitial cystitis in a patient, said method comprising the steps of:
   (a) obtaining a fluid sample from a patient;
   (b) applying the sample to a detector device, wherein the detector device is a dipstick device,
   wherein the detector device comprises at least one detection reagent,
   wherein the detection reagent is a fragment of CKAP4 which comprises a polyhistidine tag at the end of said fragment of CKAP4, and wherein the detection reagent specifically binds antiproliferative factor (APF), further wherein the detection reagent is detectably labeled,
   wherein the binding of APF to the detection reagent provides detection of a threshold level of APF in the sample in the form of a visual indication that provides correlation with the presence of interstitial cystitis, and
   wherein the threshold level is above about 10 fMolar; and,
   (c) visualizing the dipstick device to ascertain a positive screen for interstitial cystitis.

2. The method of claim 1, wherein the fluid sample is urine.

3. The method of claim 1, wherein the detection reagent is produced in a bacterial expression system.

4. The method of claim 1, wherein the detector device visual display comprises a "Yes/No" indicator.

* * * * *